(12) United States Patent
Christ et al.

(10) Patent No.: US 7,968,568 B2
(45) Date of Patent: Jun. 28, 2011

(54) SUBSTITUTED PIPERIDINE DERIVATIVES AS SST5 MODULATORS

(75) Inventors: Andreas D. Christ, Arlesheim (CH); Rainer E. Martin, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/621,542

(22) Filed: Nov. 19, 2009

(65) Prior Publication Data

US 2010/0069413 A1    Mar. 18, 2010

Related U.S. Application Data

(62) Division of application No. 11/821,458, filed on Jun. 21, 2007, now Pat. No. 7,674,804.

(30) Foreign Application Priority Data

Jun. 29, 2006   (EP) ..................... 06116346

(51) Int. Cl.
*A61K 31/445* (2006.01)
(52) U.S. Cl. .............. 514/322; 544/293; 546/244
(58) Field of Classification Search .......... 514/322; 544/293; 546/244
See application file for complete search history.

(56) References Cited

U.S. PATENT DOCUMENTS

| 2006/0052599 A1 | 3/2006 | Ishibashi et al. |
| 2007/0167459 A1* | 7/2007 | Habashita et al. ......... 514/258.1 |

FOREIGN PATENT DOCUMENTS

WO   WO 01/44191 A   6/2001

* cited by examiner

*Primary Examiner* — James O Wilson
*Assistant Examiner* — Douglas M Willis
(74) *Attorney, Agent, or Firm* — George W. Johnston; Dennis P. Tramaloni; Samuel H. MeGerditchian

(57) ABSTRACT

This invention is concerned with compounds of the formula

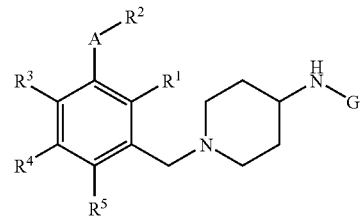

I wherein A, $R^1$ to $R^5$ and G are as defined in the description and claims, and pharmaceutically acceptable salts thereof. The invention further relates to pharmaceutical compositions containing such compounds, to a process for their preparation and to their use for the treatment and/or prevention of diseases which are associated with the modulation of SST receptors subtype 5.

18 Claims, No Drawings

SUBSTITUTED PIPERIDINE DERIVATIVES AS SST5 MODULATORS

PRIORITY TO RELATED APPLICATION(S)

This application is a divisional of U.S. application Ser. No. 11/821,458 filed Jun. 21, 2007, now allowed, which claims the benefit of European Patent Application No. 06116346.5, filed Jun. 29, 2006, which is hereby incorporated by reference in its entirety.

FIELD OF THE INVENTION

The present invention is concerned with novel pyrimidine, quinazoline and purine derivatives, their manufacture, pharmaceutical compositions containing them and their use as medicaments. The active compounds of the present invention are useful in the prevention and/or treatment of diabetes mellitus and other disorders.

In a preferred embodiment, the present invention is concerned with compounds of the formula I

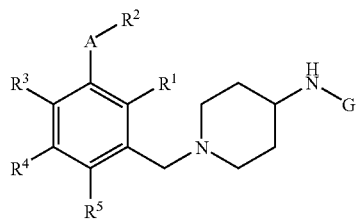

and pharmaceutically acceptable salts thereof.

The compounds of formula I possess pharmaceutical activity, in particular they are modulators of somatostatin receptor activity. More particularly, the compounds are antagonists of the somatostatin receptor subtype 5 (SSTR5).

All documents cited or relied upon below are expressly incorporated herein by reference.

BACKGROUND OF THE INVENTION

Diabetes mellitus is a systemic disease characterized by metabolic disorders involving insulin, carbohydrates, fats and proteins, and disorders in the structure and function of blood vessels. The primary symptom of acute diabetes is hyperglycemia, often accompanied by glucosuria, the presence in urine of large amounts of glucose, and polyuria, the excretion of large volumes of urine. Additional symptoms arise in chronic diabetes, including degeneration of the walls of blood vessels. Although many different human organs are affected by these vascular changes, the eyes and kidneys appear to be the most susceptible. As such, long-standing diabetes mellitus, even when treated with insulin, is a leading cause of blindness.

There are three recognized types of diabetes mellitus. Type I diabetes or insulin dependent diabetes mellitus (IDDM) is typically of juvenile onset; ketosis develops early in life with much more severe symptoms and has a near-certain prospect of later vascular involvement. Control of Type I diabetes is difficult and requires exogenous insulin administration. Type II diabetes or non-insulin dependent diabetes mellitus (NIDDM) is ketosis-resistant, generally develops later in life, is milder and has a more gradual onset. Gestational diabetes is related to type II diabetes and associated with an increased risk of later development of that disease. Type III diabetes is malnutrition-related diabetes.

NIDDM is a condition that poses a major threat to the health of the citizens of the western world. NIDDM accounts for over 85% of diabetes incidence worldwide and about 160 million people are suffering from NIDDM. The incidence is expected to increase considerably within the next decades, especially in developing countries. NIDDM is associated with morbidity and premature mortality resulting from serious complications, e.g., cardiovascular disease (G. C. Weir and J. L. Leahy, Pathogenesis of non-insulin dependent (Type II) diabetes mellitus, in *Joslin's Diabetes Mellitus* (Eds. C. R. Kahn and G. C. Weir), 13th Edition, 1994, Lea & Febiger, Malvern, Pa., pp. 240-264). NIDDM is characterized by both fasting and post-prandial hyperglycemia resulting from abnormalities in insulin secretion and insulin action (G. C. Weir et al., vide supra).

The hyperglycemia in patients suffering from NIDDM can usually be initially treated by dieting, but eventually most NIDDM patients have to take oral antidiabetic agents and/or insulin injections to normalize their blood glucose levels. The introduction of orally effective hypoglycemic agents was an important development in the treatment of hyperglycemia by lowering blood glucose levels. Currently, the most widely used oral antidiabetic agents are the sulfonylureas, which act by increasing the secretion of insulin from the pancreas (H. E. Lebovitz, Oral antidiabetic agents, in *Joslin's Diabetes Mellitus* (Eds. C. R. Kahn and G. C. Weir), 13th Edition, 1994, Lea & Febiger, Malvern, Pa., pp. 508-529), the biguanides (e.g., metformin) which act on the liver and periphery by unknown mechanisms (C. J. Bailey, M. R. C. Path and R. C. Turner *N. Engl. J. Med.* 1996, 334, 574-579) and the thiazolidinediones (e.g., rosiglitazone/Avandia®), which enhance the effects of insulin at peripheral target sites (G. L. Plosker and D. Faulds *Drugs* 1999, 57, 409-438). These existing therapies which comprise a wide variety of biguanide, sulfonylurea and thiazolidinedione derivatives have been used clinically as hypoglycemic agents. However, all three classes of compound have side effects. The biguanides, for example metformin, are unspecific and in certain cases have been associated with lactic acidosis, and need to be given over a longer period of time, i.e. they are not suitable for acute administration (C. J. Bailey et al., vide supra). The sulfonylureas, though having good hypoglycemic activity, require great care during use because they frequently cause serious hypoglycemia and are most effective over a period of circa ten years. The thiazolidinediones may cause weight gain following chronic administration (G. L. Plosker and D. Faulds, vide supra) and troglitazone has been associated with the occurrence of serious hepatic dysfunction.

Thus, there is a significant and rising need for antidiabetic drugs that have novel mechanisms of action, thereby avoiding side effects produced by known therapies. The hormone somatostatin (SST) is primarily produced in the intestinal tract and in the pancreas. In addition it acts as a neurotransmitter. The hormone is involved through its receptors in the regulation of several other hormones and in immunoregulation. In particular, SST suppresses the secretion of insulin by pancreatic β cells and the secretion of glucagon-like peptide 1 (GLP-1) by L cells. GLP-1 in turn is one of the most potent stimulators of insulin production and secretion and is a trophic factor for β cells. β and L cells express SST receptor subtype 5 (SSTR5) and agonizing this receptor suppresses insulin and GLP-1 secretion in humans and in animal models (e.g., Y. Zambre, Z. Ling, M.-C. Chen, X. Hou, C.-W. Woon, M. Culler, J. E. Taylor, D. H. Coy, C. van Schravendijk, F.

Schuit, D. G. Pipeleers and D. L. Eizirik *Biochem. Pharmacol.* 1999, 57, 1159-1164; S. P. Fagan, A. Azizzadeh, S. Moldovan, M. K. Ray, T. E. Adrian, X. Ding, D. H. Coy and F. C. Brunicardi *Surgery* 1998, 124, 254-258; M. Norman, S. Moldovan, V. Seghers, X.-P. Wang, F. J. DeMayo and F. C. Brunicardi *Ann. Surg.* 2002, 235, 767-774; T. A. Tirone, M. A. Norman, S. Moldovan, F. J. DeMayo, X.-P. Wang and F. C. Brunicardi *Pancreas* 2003, 26, e67-73; M. Z. Strowski, M. Köhler, H. Y. Chen, M. E. Trumbauer, Z. Li, D. Szalkowski, S. Gopal-Truter, J. K. Fisher, J. M. Schaeffer, A. D. Blake, B. B. Zhang and H. A. Wilkinson *Mol. Endocrinol.* 2003, 17, 93-106).

Consequently, antagonizing the effect of SST would lead to higher plasma insulin concentrations. In patients suffering from impaired glucose tolerance and NIDDM, a higher plasma insulin concentration would moderate the dangerous hyperglycemia and accordingly reduce the risk of tissue damage. If such SSTR5 antagonists are sufficiently selective over the other four SST receptors, little influence is expected on secretion of other hormones. Particularly, selectivity over SST receptor subtype 2 avoids influences on glucagon secretion (K. Cejvan, D. H. Coy and S. Efendic *Diabetes* 2003, 52, 1176-1181; M. Z. Strowski, R. M. Parmar, A. D. Blake and J. M. Schaeffer *Endocrinology* 2000, 141, 111-117). Advantageous over established therapies is the dual mechanism of action to increase insulin secretion: directly on pancreatic β cells and indirectly through GLP-1 release from L cells. Additionally, SSTR5 knockout mice demonstrated higher insulin sensitivity than littermates (M. Z. Strowski, M. Köhler et al., vide supra). Therefore, SSTR5 antagonists could have the potential to beneficially influence insulin resistance in patients with NIDDM. In summary, SSTR5 antagonists are expected to beneficially influence NIDDM, the underlying impaired fasting glucose and impaired glucose tolerance, as well as complications of long-standing, insufficiently controlled diabetes mellitus.

GLP-1 is known as an endogenous regulator of gastrointestinal motility and of food intake reducing appetite as shown in laboratory animals, healthy volunteers and patients with NIDDM (E. Näslund, B. Barkeling, N. King, M. Gutniak, J. E. Blundell, J. J. Holst, S. Rössner and P. M. Hellström *Int. J. Obes.* 1999, 23, 304-311; J.-P. Gutzwiller, B. Göke, J. Drewe, P. Hildebrand, S. Ketterer, D. Handschin, R. Winterhalder, D. Conen and C. Beglinger *Gut* 1999, 44, 81-88; J.-P. Gutzwiller, J. Drewe, B. Göke, H. Schmidt, B. Rohrer, J. Lareida and C. Beglinger *Am. J. Physiol.* 1999, 276, R1541-1544; M. D. Turton, D. O'Shea, I. Gunn, S. A. Beak, C. M. Edwards, K. Meeran, S. J. Choi, G. M. Taylor, M. M. Heath, P. D. Lambert, J. P. Wilding, D. M. Smith, M. A. Ghatei, J. Herbert and S. R. Bloom *Nature* 1996, 379, 69-72; A. Flint, A. Raben, A. Astrup and J. J. Holst *J. Clin. Invest.* 1998, 101, 515-520; M. B. Toft-Nielsen, S. Madsbad and J. J. Holst *Diabetes Care* 1999, 22, 1137-1143; P. K. Cheikani, A. C. Haver and R. D. Reidelberger *Am. J. Physiol.* 2005, 288, R1695-R1706; T. Miki, K. Minami, H. Shinozaki, K. Matsumura, A. Saraya, H. Ikeda, Y. Yamada, J. J. Hoist and S. Seino *Diabetes* 2005, 54, 1056-1063); thus, elevated GLP-1 will also counteract obesity, a typical condition associated with and leading to NIDDM.

GLP-1 is co-secreted with GLP-2 that is, consequently, also regulated by SST through SSTR5 (L. Hansen, B. Hartmann, T. Bisgaard, H. Mineo, P. N. Jørgensen and J. J. Hoist *Am. J. Phys.* 2000, 278, E1010-1018). GLP-2 is eterotrophic and beneficial in patients with malabsorption of certain origins, such as short bowel syndrome (D. G. Burrin, B. Stoll and X. Guan *Domest. Anim. Endocrinol.* 2003, 24, 103-122; K. V. Haderslev, P. B. Jeppesen, B. Hartmann, J. Thulesen, H. A. Sorensen, J. Graff, B. S. Hansen, F. Tofteng, S. S. Poulsen, J. L. Madsen, J. J. Hoist, M. Staun and P. B. Mortensen *Scand. J. Gastroenterol.* 2002, 37, 392-398; P. B. Jeppesen *J. Nutr.* 2003, 133, 3721-3724).

Moreover, there is increasing evidence for a role of SST on immune cells and expression of SSTR5 on activated T lymphocytes (T. Talme, J. Ivanoff, M. Hägglund, R. J. J. van Neerven, A. Ivanoff and K. G. Sundqvist *Clin. Exp. Immunol.* 2001, 125, 71-79; D. Ferone, P. M. van Hagen, C. Semino, V. A. Dalm, A. Barreca, A. Colao, S. W. J. Lamberts, F. Minuto and L. J. Hofland *Dig. Liver Dis.* 2004, 36, S68-77; C. E. Ghamrawy, C. Rabourdin-Combe and S. Krantic *Peptides* 1999, 20, 305-311). Consequently, SSTR5 antagonists could also prove valuable in treating diseases characterized by a disturbed immune system, such as inflammatory bowel disease.

SUMMARY OF THE INVENTION

In an embodiment of the present invention, provided is a compound of formula I:

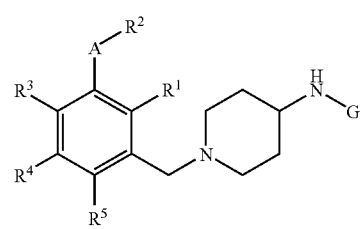

wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl, and benzyl;

$R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O—$C_{3-7}$-cycloalkyl, halogen, halogen-$C_{1-7}$-alkyl, —$NR^6R^7$, wherein $R^6$ and $R^7$ independently from each other are hydrogen or $C_{1-7}$-alkyl, —O—$SO_2$—$R^8$, wherein $R^8$ is $C_{1-7}$-alkyl, and pyrrolyl;

$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —O—C(CH$_3$)$_2$—CH=CH—;

$R^5$ is selected from the group consisting of hydrogen, halogen and $C_{1-7}$-alkoxy;

G is selected from the groups

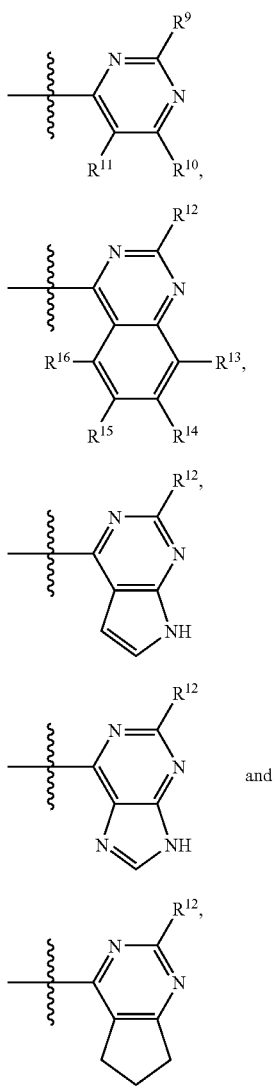

wherein
$R^9$ is selected from the group consisting of hydrogen, $C_{1-7}$-alkyl,
halogen, halogen-$C_{1-7}$-alkyl,
amino, phenyl,
—$OR^{17}$, wherein $R^{17}$ is hydrogen or $C_{1-7}$-alkyl, and
—$C(O)$—$OR^{18}$, wherein $R^{18}$ is hydrogen or $C_{1-7}$-alkyl;
$R^{10}$ is selected from the group consisting of hydrogen, $C_{1-7}$-alkyl, $C_{1-7}$-alkoxy,
halogen, halogen-$C_{1-7}$-alkyl,
—$C(O)$—$OR^{19}$, wherein $R^{19}$ is hydrogen or $C_{1-7}$-alkyl, and
—$NR^{20}R^{21}$, wherein $R^{20}$ is hydrogen or $C_{1-7}$-alkyl and $R^{21}$ is selected from the group consisting of hydrogen, $C_{1-7}$-alkyl and $C_{1-7}$-alkylcarbonyl,
or wherein $R^{20}$ and $R^{21}$ together with the nitrogen atom they are attached to form a 3-, 4-, 5-, 6- or 7-membered heterocyclic ring;
$R^{11}$ is selected from the group consisting of hydrogen, $C_{1-7}$-alkyl, $C_{1-7}$-alkoxy,
halogen, halogen-$C_{1-7}$-alkyl, amino,
—$(CH_2)_m$—$C(O)$—$OR^{22}$, wherein m is 0 or 1 and $R^{22}$ is hydrogen or $C_{1-7}$-alkyl,
phenyloxy, wherein phenyl is unsubstituted or substituted by one to three groups selected from the group consisting of $C_{1-7}$-alkyl, $C_{1-7}$-alkoxy, halogen and halogen-$C_{1-7}$-alkyl, and
—$(CH_2)_n$-phenyl, wherein n is 0 or 1 and phenyl is unsubstituted or substituted by one to three groups selected from the group consisting of $C_{1-7}$-alkyl, $C_{1-7}$-alkoxy, halogen and halogen-$C_{1-7}$-alkyl;
$R^{12}$ is selected from the group consisting of hydrogen, $C_{1-7}$-alkyl,
halogen, halogen-$C_{1-7}$-alkyl,
amino, phenyl,
—$OR^{23}$, wherein $R^{23}$ is hydrogen or $C_{1-7}$-alkyl, and
—$C(O)$—$OR^{24}$, wherein $R^{24}$ is hydrogen or $C_{1-7}$-alkyl;
$R^{13}$, $R^{14}$, $R^{15}$ and $R^{16}$ independently from each other are selected from the group consisting of hydrogen, $C_{1-7}$-alkyl, halogen, hydroxy, and $C_{1-7}$-alkoxy;
and pharmaceutically acceptable salts thereof.

In another embodiment of the present invention, provided is a process for the manufacture of a compound according to formula I, comprising the steps of: reacting a compound of the general formula $$G-X \qquad\qquad II$$

wherein G is as defined in claim 1 and X is halogen, with a compound of the formula

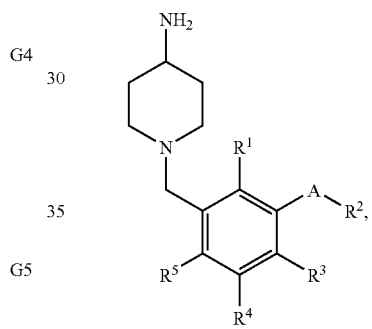

wherein A and $R^1$ to $R^5$ are as defined above,
to obtain a compound of the formula

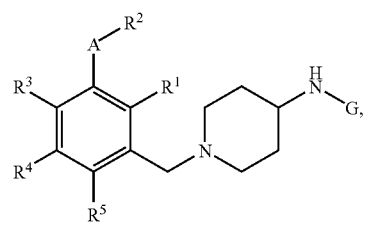

and, if desired, converting the compound of formula I into a pharmaceutically acceptable salt; or, alternatively, reacting a compound of the general formula

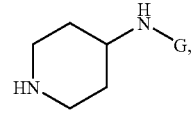

wherein G is as defined above, with an aldehyde of the formula

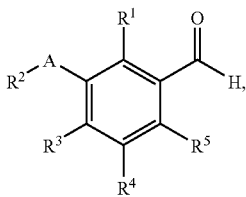

wherein A and $R^1$ to $R^5$ are as defined above, by employing a reducing agent to obtain a compound of the formula

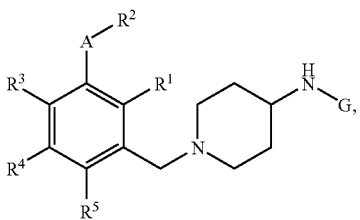

and, if desired, converting the compound of formula I into a pharmaceutically acceptable salt.

In a further embodiment of the present invention, provided is a pharmaceutical composition, comprising a therapeutically effective amount of a compound according to claim 1 as well as a pharmaceutically acceptable carrier and/or adjuvant.

In a still another embodiment of the present invention, provided is method for the treatment of diseases which are associated with the modulation of SST receptors subtype 5, comprising the step of administering a therapeutically effective amount of a compound according to claim 1 to a human being or animal in need thereof.

DETAILED DESCRIPTION

It is therefore an embodiment of the present invention to provide selective, directly acting SSTR5 antagonists. Such antagonists are useful as therapeutically active substances, particularly in the treatment and/or prevention of diseases which are associated with the modulation of SST receptors subtype 5.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 4 carbon atoms. Examples of straight-chain and branched $C_1$-$C_7$ alkyl groups are methyl, ethyl, propyl, isopropyl, butyl, isobutyl, tert-butyl, the isomeric pentyls, the isomeric hexyls and the isomeric heptyls, preferably methyl, ethyl, isopropyl, butyl and isobutyl, and most preferred the groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl (allyl).

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

The term "alkoxy" refers to the group R'—O—, wherein R' is alkyl. The term "lower alkoxy" or "$C_{1-7}$-alkoxy" refers to the group R'—O—, wherein R' is lower alkyl and the term "lower alkyl" has the previously given significance. Examples of lower alkoxy groups are e.g., methoxy, ethoxy, n-propoxy, isopropoxy, n-butoxy, iso-butoxy, sec-butoxy and tert-butoxy, preferably methoxy and ethoxy and most preferred the groups specifically exemplified herein.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by an alkoxy group as defined above. Among the preferred lower alkoxyalkyl groups are methoxymethyl, methoxyethyl and ethoxymethyl.

The term "lower alkoxyalkoxy" or "$C_{1-7}$-alkoxy-$C_{1-7}$-alkoxy" refers to lower alkoxy groups as defined above wherein at least one of the hydrogen atoms of the lower alkoxy group is replaced by an alkoxy group as defined above. Among the preferred lower alkoxyalkoxy groups are 2-methoxy-ethoxy and 3-methoxy-propoxy.

The term "halogen" refers to fluorine, chlorine, bromine and iodine, with fluorine, chlorine and bromine being preferred.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl, chloromethyl, 2-fluoroethyl and 2,2,2-trifluoroethyl, with trifluoromethyl, 2-fluoroethyl and 2,2,2-trifluoroethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy, chloromethoxy, 2-fluoroethoxy and 2,2,2-trifluoroethoxy, with trifluoromethoxy, 2-fluoroethoxy and 2,2,2-trifluoroethoxy being especially preferred.

The term "lower hydroxyalkoxy" or hydroxy-$C_{1-7}$-alkoxy" refers to lower alkoxy groups as defined above wherein at least one of the hydrogen atoms of the lower alkoxy group is replaced by a hydroxy group. Examples of lower hydroxyalkoxy groups are hydroxymethoxy or hydroxyethoxy.

The term "lower alkylsulfonyl" or "$C_{1-7}$-alkylsulfonyl" refers to the group R'—C(O)—, wherein R' is lower alkyl as defined herein before. Examples of lower alkylcarbonyl groups are e.g. acetyl (methylcarbonyl) or ethylcarbonyl.

The term "form a 3-, 4-, 5-, 6- or 7-membered heterocyclic ring" refers to a N-heterocyclic ring selected from the group consisting of aziridinyl, azetidinyl, pyrrolidinyl, piperidinyl and azepanyl. A preferred heterocyclic ring is azetidinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the general formula I

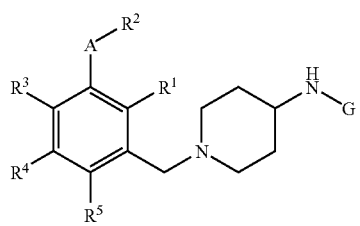

I wherein
A is —O— or —NH—;
$R^1$ is selected from the group consisting of hydrogen, $C_{1-7}$-alkoxy and halogen;
$R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl, and benzyl;
$R^3$ is selected from the group consisting of hydrogen, $C_{1-7}$-alkyl,
hydroxy, $C_{1-7}$-alkoxy, $C_{2-7}$-alkenyloxy,
hydroxy-$C_{1-7}$-alkoxy, $C_{1-7}$-alkoxy-$C_{1-7}$-alkoxy,
—O—$C_{3-7}$-cycloalkyl,
halogen, halogen-$C_{1-7}$-alkyl,
—$NR^6R^7$, wherein $R^6$ and $R^7$ independently from each other are hydrogen or $C_{1-7}$-alkyl,
—O—$SO_2$—$R^8$, wherein $R^8$ is $C_{1-7}$-alkyl,
and pyrrolyl;
$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;
or $R^3$ and $R^4$ are bonded to each other to form a ring together with the carbon atoms they are attached to and $R^3$ and $R^4$ together are —O—$C(CH_3)_2$—CH=CH—;
$R^5$ is selected from the group consisting of hydrogen, halogen and $C_{1-7}$-alkyl;
G is selected from the groups

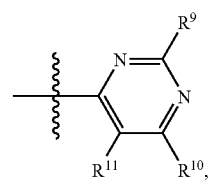

G1

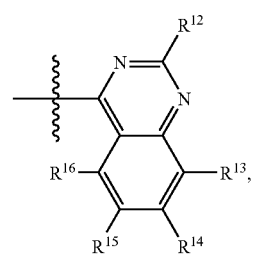

G2

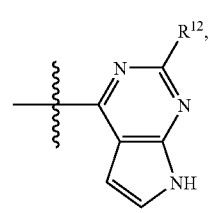

G3

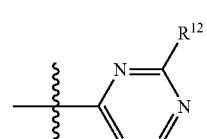

G4 and

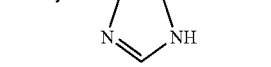

G5 wherein
R$^9$ is selected from the group consisting of hydrogen, C$_{1-7}$-alkyl,
halogen, halogen-C$_{1-7}$-alkyl,
amino, phenyl,
—OR$^{17}$, wherein R$^{17}$ is hydrogen or C$_{1-7}$-alkyl, and
—C(O)—OR$^{18}$, wherein R$^{18}$ is hydrogen or C$_{1-7}$-alkyl;
R$^{10}$ is selected from the group consisting of hydrogen, C$_{1-7}$-alkyl, C$_{1-7}$-alkoxy,
halogen, halogen-C$_{1-7}$-alkyl,
—C(O)—OR$^{19}$, wherein R$^{19}$ is hydrogen or C$_{1-7}$-alkyl, and
—NR$^{20}$R$^{21}$, wherein R$^{20}$ is hydrogen or C$_{1-7}$-alkyl and R$^{21}$ is selected from the group consisting of hydrogen, C$_{1-7}$-alkyl and C$_{1-7}$-alkylcarbonyl,
or wherein R$^{20}$ and R$^{21}$ together with the nitrogen atom they are attached to form a 3-, 4-, 5-, 6- or 7-membered heterocyclic ring;
R$^{11}$ is selected from the group consisting of hydrogen, C$_{1-7}$-alkyl, C$_{1-7}$-alkoxy,
halogen, halogen-C$_{1-7}$-alkyl, amino,
—(CH$_2$)$_m$—C(O)—OR$^{22}$, wherein m is 0 or 1 and R$^{22}$ is hydrogen or C$_{1-7}$-alkyl,
phenyloxy, wherein phenyl is unsubstituted or substituted by one to three groups selected from the group consisting of C$_{1-7}$-alkyl, C$_{1-7}$-alkoxy, halogen and halogen-C$_{1-7}$-alkyl, and
—(CH$_2$)$_n$-phenyl, wherein n is 0 or 1 and phenyl is unsubstituted or substituted by one to three groups selected from the group consisting of C$_{1-7}$-alkyl, C$_{1-7}$-alkoxy, halogen and halogen-C$_{1-7}$-alkyl;
R$^{12}$ is selected from the group consisting of hydrogen, C$_{1-7}$-alkyl,
halogen, halogen-C$_{1-7}$-alkyl,
amino, phenyl,
—OR$^{23}$, wherein R$^{23}$ is hydrogen or C$_{1-7}$-alkyl, and
—C(O)—OR$^{24}$, wherein R$^{24}$ is hydrogen or C$_{1-7}$-alkyl;
R$^{13}$, R$^{14}$, R$^{15}$ and R$^{16}$ independently from each other are selected from the group consisting of
hydrogen, C$_{1-7}$-alkyl, halogen, hydroxy, and C$_{1-7}$-alkoxy;
and pharmaceutically acceptable salts thereof.

Preferred compounds of formula I of the present invention are those, wherein A is O.

Also preferred are compounds of formula I, wherein A is NH.

Furthermore, compounds of formula I according to the present invention are preferred, wherein R$^1$ is hydrogen or halogen.

Also preferred are compounds of formula I according to the invention, wherein R$^2$ is selected from the group consisting of C$_{2-7}$-alkyl, C$_{2-7}$-alkenyl, halogen-C$_{1-7}$-alkyl and C$_{1-7}$-alkoxy-C$_{1-7}$-alkyl. Especially preferred are those compounds of formula I, wherein R$^2$ is selected from the group consisting of ethyl, propyl, isopropyl, allyl, 2-fluoroethyl, 2,2,2-trifluoroethyl, butyl and isobutyl, with those compounds, wherein R$^2$ is ethyl or isopropyl, being most preferred.

Further preferred compounds of formula I according to the present invention are those, wherein R$^3$ is selected from the group consisting of is selected from the group consisting of hydrogen, C$_{1-7}$-alkyl, hydroxy, C$_{1-7}$-alkoxy, halogen, —NR$^6$R$^7$, wherein R$^6$ and R$^7$ independently from each other are hydrogen or C$_{1-7}$-alkyl, —O—SO$_2$—R$^8$, wherein R$^8$ is C$_{1-7}$-alkyl, and pyrrolyl.

More preferred are those compounds of formula I, wherein R$^3$ is hydrogen or halogen, with those compounds, wherein R$^3$ is halogen, being especially preferred. Most preferably, R$^3$ is chloro.

Furthermore, compounds of formula I of the present invention are preferred, wherein R$^4$ is selected from the group consisting of hydrogen, hydroxy, C$_{1-7}$-alkoxy, nitro, C$_{1-7}$-alkoxy-C$_{1-7}$-alkoxy, and —O-benzyl.

Another group of preferred compounds of formula I according to the present invention are those, wherein R$^3$ and R$^4$ are bonded to each other to form a ring together with the carbon atoms they are attached to and R$^3$ and R$^4$ together are —O—C(CH$_3$)$_2$—CH=CH—.

These are compounds of the formulae Ia:

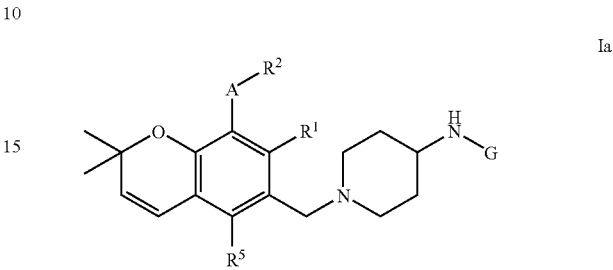

Ia

Furthermore, compounds of formula I according to the invention are preferred, wherein R$^5$ is hydrogen or halogen, with those compounds of formula I, wherein R$^5$ is hydrogen, being more preferred.

Especially preferred are compounds of formula I according to the present invention, wherein G is

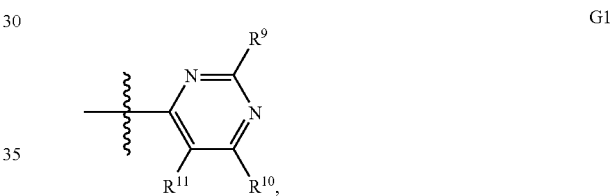

G1 and wherein
R$^9$ is selected from the group consisting of hydrogen, C$_{1-7}$-alkyl,
halogen, halogen-C$_{1-7}$-alkyl,
amino, phenyl,
—OR$^{17}$, wherein R$^{17}$ is hydrogen or C$_{1-7}$-alkyl, and
—C(O)—OR$^{18}$, wherein R$^{18}$ is hydrogen or C$_{1-7}$-alkyl;
R$^{10}$ is selected from the group consisting of hydrogen, C$_{1-7}$-alkyl, C$_{1-7}$-alkoxy,
halogen, halogen-C$_{1-7}$-alkyl,
—C(O)—OR$^{19}$, wherein R$^{19}$ is hydrogen or C$_{1-7}$-alkyl, and
—NR$^{20}$R$^{21}$, wherein R$^{20}$ is hydrogen or C$_{1-7}$-alkyl and R$^{21}$ is selected from the group consisting of hydrogen, C$_{1-7}$-alkyl and C$_{1-7}$-alkylcarbonyl,
or wherein R$^{20}$ and R$^{21}$ together with the nitrogen atom they are attached to form a 3-, 4-, 5-, 6- or 7-membered heterocyclic ring;
R$^{11}$ is selected from the group consisting of hydrogen, C$_{1-7}$-alkyl, C$_{1-7}$-alkoxy,
halogen, halogen-C$_{1-7}$-alkyl, amino,
—(CH$_2$)$_m$—C(O)—OR$^{22}$, wherein m is 0 or 1 and R$^{22}$ is hydrogen or C$_{1-7}$-alkyl,
phenyloxy, wherein phenyl is unsubstituted or substituted by one to three groups selected from the group consisting of C$_{1-7}$-alkyl, C$_{1-7}$-alkoxy, halogen and halogen-C$_{1-7}$-alkyl, and
—(CH$_2$)$_n$-phenyl, wherein n is 0 or 1 and phenyl is unsubstituted or substituted by one to three groups selected from the group consisting of C$_{1-7}$-alkyl, C$_{1-7}$-alkoxy, halogen and halogen-C$_{1-7}$-alkyl.

Within this group, those compounds of formula I are preferred, wherein $R^9$ is hydrogen or halogen.

In addition, those compounds of formula I are preferred, wherein $R^{10}$ is selected from the group consisting of hydrogen, $C_{1-7}$-alkyl, $C_{1-7}$-alkoxy, halogen and —C(O)—$OR^{19}$, wherein $R^{19}$ is hydrogen or $C_{1-7}$-alkyl.

Furthermore, compounds of formula I are preferred, wherein $R^{11}$ is selected from the group consisting of hydrogen, $C_{1-7}$-alkyl, $C_{1-7}$-alkoxy, halogen and phenyloxy, wherein phenyl is unsubstituted or substituted by one to three groups selected from $C_{1-7}$-alkyl and $C_{1-7}$-alkoxy.

Another group of preferred compounds of formula I according to the invention are those, wherein G is

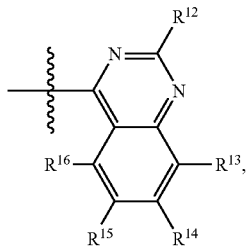

G2 and wherein $R^{12}$ is selected from the group consisting of hydrogen, $C_{1-7}$-alkyl, halogen, halogen-$C_{1-7}$-alkyl, amino, phenyl, —$OR^{23}$, wherein $R^{23}$ is hydrogen or $C_{1-7}$-alkyl, and —C(O)—$OR^{24}$, wherein $R^{24}$ is hydrogen or $C_{1-7}$-alkyl; and $R^{13}$, $R^{14}$, $R^{15}$ and $R^{16}$ independently from each other are selected from the group consisting of hydrogen, $C_{1-7}$-alkyl, halogen, hydroxy, and $C_{1-7}$-alkoxy.

Within this group, those compounds are preferred, wherein $R^{12}$ is halogen, more preferably $R^{11}$ is chloro.

A further group of preferred compounds of formula I according to the invention are those, wherein G is selected from the group consisting of

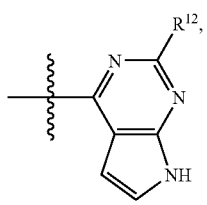

G3

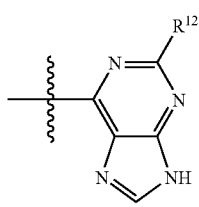

G4 and

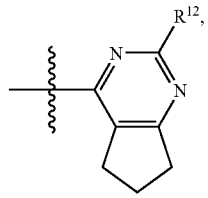

G5 and wherein $R^{12}$ is selected from the group consisting of hydrogen, $C_{1-7}$-alkyl, halogen, halogen-$C_{1-7}$-alkyl, amino, phenyl, —$OR^{23}$, wherein $R^{23}$ is hydrogen or $C_{1-7}$-alkyl, and —C(O)—$OR^{24}$, wherein $R^{24}$ is hydrogen or $C_{1-7}$-alkyl.

Also within this group, those compounds are preferred, wherein $R^{12}$ is halogen, more preferably $R^{12}$ is chloro.

Examples of preferred compounds of formula I are the following:

(2-chloro-pyrimidin-4-yl)-[1-(3-ethoxy-4-methoxy-benzyl)-piperidin-4-yl]-amine, 2-chloro-N-[1-(3-ethoxy-4-methoxy-benzyl)-piperidin-4-yl]-N'-isopropyl-pyrimidine-4,6-diamine, (2-chloro-5-methyl-pyrimidin-4-yl)-[1-(3-ethoxy-4-methoxy-benzyl)-piperidin-4-yl]-amine, N-{2-chloro-6-[1-(3-ethoxy-4-methoxy-benzyl)-piperidin-4-ylamino]-pyrimidin-4-yl}-acetamide, $N^4$-[1-(3-ethoxy-4-methoxy-benzyl)-piperidin-4-yl]-6-methyl-pyrimidine-2,4-diamine, (2,7-dichloro-quinazolin-4-yl)-[1-(3-ethoxy-4-methoxy-benzyl)-piperidin-4-yl]-amine,

[1-(3-ethoxy-4-methoxy-benzyl)-piperidin-4-yl]-(2-phenyl-quinazolin-4-yl)-amine, (2-chloro-5-fluoro-pyrimidin-4-yl)-[1-(3-ethoxy-4-methoxy-benzyl)-piperidin-4-yl]-amine, (2,6-dichloro-pyrimidin-4-yl)-[1-(3-ethoxy-4-methoxy-benzyl)-piperidin-4-yl]-amine,

[1-(3-ethoxy-4-methoxy-benzyl)-piperidin-4-yl]-(2,5,6-trichloro-pyrimidin-4-yl)-amine, 6-chloro-$N^4$-[1-(3-ethoxy-4-methoxy-benzyl)-piperidin-4-yl]-pyrimidine-2,4-diamine, 6-chloro-$N^4$-[1-(3-ethoxy-4-methoxy-benzyl)-piperidin-4-yl]-pyrimidine-4,5-diamine, (6-azetidin-1-yl-2-chloro-pyrimidin-4-yl)-[1-(3-ethoxy-4-methoxy-benzyl)-piperidin-4-yl]-amine, (7-chloro-quinazolin-4-yl)-[1-(3-ethoxy-4-methoxy-benzyl)-piperidin-4-yl]-amine, (2,7-dichloro-6-fluoro-quinazolin-4-yl)-[1-(3-ethoxy-4-methoxy-benzyl)-piperidin-4-yl]-amine, (2-chloro-6,7-dimethoxy-quinazolin-4-yl)-[1-(3-ethoxy-4-methoxy-benzyl)-piperidin-4-yl]-amine,

[1-(4-chloro-3-ethoxy-benzyl)-piperidin-4-yl]-(2-chloro-5-methyl-pyrimidin-4-yl)-amine,

[1-(4-chloro-3-ethoxy-benzyl)-piperidin-4-yl]-(2-chloro-pyrimidin-4-yl)-amine,

[1-(4-chloro-3-ethoxy-benzyl)-piperidin-4-yl]-(2-chloro-5-fluoro-pyrimidin-4-yl)-amine, 6-chloro-$N^4$-[1-(4-chloro-3-ethoxy-benzyl)-piperidin-4-yl]-pyrimidine-4,5-diamine, N-{2-chloro-6-[1-(4-chloro-3-ethoxy-benzyl)-piperidin-4-ylamino]-pyrimidin-4-yl}-acetamide,

[1-(4-chloro-3-ethoxy-benzyl)-piperidin-4-yl]-[2-chloro-5-(2-ethyl-4,5-dimethoxy-benzyl)-pyrimidin-4-yl]-amine,

[1-(4-chloro-3-ethoxy-benzyl)-piperidin-4-yl]-(7-chloro-quinazolin-4-yl)-amine,
$N^6$-[1-(4-chloro-3-ethoxy-benzyl)-piperidin-4-yl]-9H-purine-2,6-diamine,
6-chloro-$N^4$-[1-(3,5-diisopropoxy-benzyl)-piperidin-4-yl]-pyrimidine-4,5-diamine,
(6-chloro-5-phenoxy-pyrimidin-4-yl)-[1-(3,5-diisopropoxy-benzyl)-piperidin-4-yl]-amine,
(6-chloro-5-o-tolyloxy-pyrimidin-4-yl)-[1-(3,5-diisopropoxy-benzyl)-piperidin-4-yl]-amine,
[6-chloro-5-(2-methoxy-phenoxy)-pyrimidin-4-yl]-[1-(3,5-diisopropoxy-benzyl)-piperidin-4-yl]-amine,
[6-chloro-5-(2-ethoxy-phenoxy)-pyrimidin-4-yl]-[1-(3,5-diisopropoxy-benzyl)-piperidin-4-yl]-amine,
[6-chloro-5-(4-methoxy-phenoxy)-pyrimidin-4-yl]-[1-(3,5-diisopropoxy-benzyl)-piperidin-4-yl]-amine,
[6-chloro-5-(2-methoxy-benzyl)-pyrimidin-4-yl]-[1-(3,5-diisopropoxy-benzyl)-piperidin-4-yl]-amine,
[6-chloro-5-(2-trifluoromethyl-benzyl)-pyrimidin-4-yl]-[1-(3,5-diisopropoxy-benzyl)-piperidin-4-yl]-amine,
[1-(3,5-diisopropoxy-benzyl)-piperidin-4-yl]-(7H-pyrrolo[2,3-d]pyrimidin-4-yl)-amine,
(2-chloro-pyrimidin-4-yl)-[1-(3-ethoxy-4-methyl-benzyl)-piperidin-4-yl]-amine,
(2-chloro-pyrimidin-4-yl)-[1-(3-ethoxy-4-fluoro-benzyl)-piperidin-4-yl]-amine,
[1-(4-chloro-3-ethoxy-benzyl)-piperidin-4-yl]-(2-chloro-pyrimidin-4-yl)-amine,
4-[4-(2-chloro-pyrimidin-4-ylamino)-piperidin-1-ylmethyl]-2-ethoxy-phenol,
(2-chloro-pyrimidin-4-yl)-[1-(3-ethoxy-4-isopropoxy-benzyl)-piperidin-4-yl]-amine,
(2-chloro-pyrimidin-4-yl)-{1-[3-ethoxy-4-(1-ethyl-propoxy)-benzyl]-piperidin-4-yl}-amine,
[1-(3-butoxy-4-methoxy-benzyl)-piperidin-4-yl]-(2-chloro-pyrimidin-4-yl)-amine,
(2-chloro-pyrimidin-4-yl)-[1-(3,5-diethoxy-benzyl)-piperidin-4-yl]-amine,
3-[4-(2-chloro-pyrimidin-4-ylamino)-piperidin-1-ylmethyl]-5-isopropoxy-phenol,
(2-chloro-pyrimidin-4-yl)-[1-(3,5-diisopropoxy-benzyl)-piperidin-4-yl]-amine,
(2-chloro-pyrimidin-4-yl)-[1-(3-ethoxy-4-iodo-5-methoxymethoxy-benzyl)-piperidin-4-yl]-amine,
[1-(2-chloro-3,5-diethoxy-benzyl)-piperidin-4-yl]-(2-chloro-pyrimidin-4-yl)-amine,
(2-chloro-6-methyl-pyrimidin-4-yl)-[1-(3-ethoxy-4-methyl-benzyl)-piperidin-4-yl]-amine,
(2-chloro-6-methyl-pyrimidin-4-yl)-[1-(3-ethoxy-4-fluoro-benzyl)-piperidin-4-yl]-amine,
[1-(4-chloro-3-ethoxy-benzyl)-piperidin-4-yl]-(2-chloro-6-methyl-pyrimidin-4-yl)-amine,
(2-chloro-6-methyl-pyrimidin-4-yl)-[1-(3,4-diethoxy-benzyl)-piperidin-4-yl]-amine,
(2-chloro-6-methyl-pyrimidin-4-yl)-[1-(3-ethoxy-4-isopropoxy-benzyl)-piperidin-4-yl]-amine,
(2-chloro-6-methyl-pyrimidin-4-yl)-[1-(4-methoxy-3-propoxy-benzyl)-piperidin-4-yl]-amine,
(2-chloro-6-methyl-pyrimidin-4-yl)-{1-[3-(2-fluoro-ethoxy)-4-methoxy-benzyl]-piperidin-4-yl}-amine,
(2-chloro-6-methyl-pyrimidin-4-yl)-{1-[4-methoxy-3-(2,2,2-trifluoro-ethoxy)-benzyl]-piperidin-4-yl}-amine,
[1-(3-allyloxy-4-methoxy-benzyl)-piperidin-4-yl]-(2-chloro-6-methyl-pyrimidin-4-yl)-amine,
[1-(3-butoxy-4-methoxy-benzyl)-piperidin-4-yl]-(2-chloro-6-methyl-pyrimidin-4-yl)-amine,
(2-chloro-6-methyl-pyrimidin-4-yl)-[1-(3-isobutoxy-4-methoxy-benzyl)-piperidin-4-yl]-amine,
(2-chloro-6-methyl-pyrimidin-4-yl)-[1-(8-ethoxy-2,2-dimethyl-2H-chromen-6-ylmethyl)-piperidin-4-yl]-amine,
(2-chloro-6-methyl-pyrimidin-4-yl)-[1-(3,5-diethoxy-benzyl)-piperidin-4-yl]-amine,
(2-chloro-6-methyl-pyrimidin-4-yl)-[1-(3,5-diisopropoxy-benzyl)-piperidin-4-yl]-amine,
[1-(4-chloro-3,5-diethoxy-benzyl)-piperidin-4-yl]-(2-chloro-6-methyl-pyrimidin-4-yl)-amine,
[1-(4-bromo-3,5-diethoxy-benzyl)-piperidin-4-yl]-(2-chloro-6-methyl-pyrimidin-4-yl)-amine,
(2-chloro-6-methyl-pyrimidin-4-yl)-[1-(3,5-diethoxy-4-pyrrol-1-yl-benzyl)-piperidin-4-yl]-amine,
(2,6-dichloro-pyrimidin-4-yl)-[1-(3-ethoxy-4-methyl-benzyl)-piperidin-4-yl]-amine,
(2,6-dichloro-pyrimidin-4-yl)-[1-(3-ethoxy-4-fluoro-benzyl)-piperidin-4-yl]-amine,
[1-(4-chloro-3-ethoxy-benzyl)-piperidin-4-yl]-(2,6-dichloro-pyrimidin-4-yl)-amine,
4-[4-(2,6-dichloro-pyrimidin-4-ylamino)-piperidin-1-ylmethyl]-2-ethoxy-phenol,
(2,6-dichloro-pyrimidin-4-yl)-[1-(3-ethoxy-4-methoxy-benzyl)-piperidin-4-yl]-amine,
(2,6-dichloro-pyrimidin-4-yl)-[1-(3-ethoxy-4-isopropoxy-benzyl)-piperidin-4-yl]-amine,
(2,6-dichloro-pyrimidin-4-yl)-{1-[3-ethoxy-4-(1-ethyl-propoxy)-benzyl]-piperidin-4-yl}-amine,
(2,6-dichloro-pyrimidin-4-yl)-{1-[3-(2-fluoro-ethoxy)-4-methoxy-benzyl]-piperidin-4-yl}-amine,
[1-(3-allyloxy-4-methoxy-benzyl)-piperidin-4-yl]-(2,6-dichloro-pyrimidin-4-yl)-amine,
[1-(3-butoxy-4-methoxy-benzyl)-piperidin-4-yl]-(2,6-dichloro-pyrimidin-4-yl)-amine,
(2,6-dichloro-pyrimidin-4-yl)-[1-(3-isobutoxy-4-methoxy-benzyl)-piperidin-4-yl]-amine,
(2,6-dichloro-pyrimidin-4-yl)-[1-(8-ethoxy-2,2-dimethyl-2H-chromen-6-ylmethyl)-piperidin-4-yl]-amine,
(2,6-dichloro-pyrimidin-4-yl)-[1-(3,5-diethoxy-benzyl)-piperidin-4-yl]-amine,
3-[4-(2,6-dichloro-pyrimidin-4-ylamino)-piperidin-1-ylmethyl]-5-isopropoxy-phenol,
(2,6-dichloro-pyrimidin-4-yl)-[1-(3,5-diisopropoxy-benzyl)-piperidin-4-yl]-amine,
(2,6-dichloro-pyrimidin-4-yl)-[1-(3,5-diethoxy-4-fluoro-benzyl)-piperidin-4-yl]-amine,
[1-(4-chloro-3,5-diethoxy-benzyl)-piperidin-4-yl]-(2,6-dichloro-pyrimidin-4-yl)-amine,
[1-(4-bromo-3,5-diethoxy-benzyl)-piperidin-4-yl]-(2,6-dichloro-pyrimidin-4-yl)-amine,
(2,6-dichloro-pyrimidin-4-yl)-[1-(3,5-diethoxy-4-pyrrol-1-yl-benzyl)-piperidin-4-yl]-amine,
4-[1-(3-ethoxy-4-methyl-benzyl)-piperidin-4-ylamino]-6-methoxy-pyrimidin-2-ol,
4-[1-(3-ethoxy-4-fluoro-benzyl)-piperidin-4-ylamino]-6-methoxy-pyrimidin-2-ol,
4-[1-(4-chloro-3-ethoxy-benzyl)-piperidin-4-ylamino]-6-methoxy-pyrimidin-2-ol,
4-[1-(3-ethoxy-4-hydroxy-benzyl)-piperidin-4-ylamino]-6-methoxy-pyrimidin-2-ol,
4-[1-(3-ethoxy-4-methoxy-benzyl)-piperidin-4-ylamino]-6-methoxy-pyrimidin-2-ol,
4-[1-(3-ethoxy-4-isopropoxy-benzyl)-piperidin-4-ylamino]-6-methoxy-pyrimidin-2-ol,
4-methoxy-6-[1-(4-methoxy-3-propoxy-benzyl)-piperidin-4-ylamino]-pyrimidin-2-ol, 4-[1-[3-(2-fluoro-ethoxy)-4-methoxy-benzyl]-piperidin-4-ylamino]-6-methoxy-pyrimidin-2-ol,
4-[1-(3-allyloxy-4-methoxy-benzyl)-piperidin-4-ylamino]-6-methoxy-pyrimidin-2-ol,
4-[1-(3-butoxy-4-methoxy-benzyl)-piperidin-4-ylamino]-6-methoxy-pyrimidin-2-ol,
4-[1-(3-isobutoxy-4-methoxy-benzyl)-piperidin-4-ylamino]-6-methoxy-pyrimidin-2-ol,
4-[1-(8-ethoxy-2,2-dimethyl-2H-chromen-6-ylmethyl)-piperidin-4-ylamino]-6-methoxy-pyrimidin-2-ol,
4-[1-(3,5-diethoxy-benzyl)-piperidin-4-ylamino]-6-methoxy-pyrimidin-2-ol,
4-[1-(3,5-diisopropoxy-benzyl)-piperidin-4-ylamino]-6-methoxy-pyrimidin-2-ol,
4-[1-(3,5-diethoxy-4-fluoro-benzyl)-piperidin-4-ylamino]-6-methoxy-pyrimidin-2-ol,
4-[1-(4-chloro-3,5-diethoxy-benzyl)-piperidin-4-ylamino]-6-methoxy-pyrimidin-2-ol,
4-[1-(3,5-diethoxy-4-pyrrol-1-yl-benzyl)-piperidin-4-ylamino]-6-methoxy-pyrimidin-2-ol,
2-chloro-6-[1-(3-ethoxy-4-methyl-benzyl)-piperidin-4-ylamino]-pyrimidine-4-carboxylic acid methyl ester,
2-chloro-6-[1-(3-ethoxy-4-fluoro-benzyl)-piperidin-4-ylamino]-pyrimidine-4-carboxylic acid methyl ester,
2-chloro-6-[1-(4-chloro-3-ethoxy-benzyl)-piperidin-4-ylamino]-pyrimidine-4-carboxylic acid methyl ester,
2-chloro-6-[1-(3-ethoxy-4-methoxy-benzyl)-piperidin-4-ylamino]-pyrimidine-4-carboxylic acid methyl ester,
2-chloro-6-[1-(3-ethoxy-4-isopropoxy-benzyl)-piperidin-4-ylamino]-pyrimidine-4-carboxylic acid methyl ester,
2-chloro-6-{1-[3-(2-fluoro-ethoxy)-4-methoxy-benzyl]-piperidin-4-ylamino}-pyrimidine-4-carboxylic acid methyl ester,
6-[1-(3-allyloxy-4-methoxy-benzyl)-piperidin-4-ylamino]-2-chloro-pyrimidine-4-carboxylic acid methyl ester,
6-[1-(3-butoxy-4-methoxy-benzyl)-piperidin-4-ylamino]-2-chloro-pyrimidine-4-carboxylic acid methyl ester,
2-chloro-6-[1-(3-isobutoxy-4-methoxy-benzyl)-piperidin-4-ylamino]-pyrimidine-4-carboxylic acid methyl ester,
2-chloro-6-[1-(8-ethoxy-2,2-dimethyl-2H-chromen-6-ylmethyl)-piperidin-4-ylamino]-pyrimidine-4-carboxylic acid methyl ester,
2-chloro-6-[1-(3,5-diethoxy-benzyl)-piperidin-4-ylamino]-pyrimidine-4-carboxylic acid methyl ester,
2-chloro-6-[1-(3-hydroxy-5-isopropoxy-benzyl)-piperidin-4-ylamino]-pyrimidine-4-carboxylic acid methyl ester,
2-chloro-6-[1-(3,5-diisopropoxy-benzyl)-piperidin-4-ylamino]-pyrimidine-4-carboxylic acid methyl ester,
2-chloro-6-[1-(3,5-diethoxy-4-fluoro-benzyl)-piperidin-4-ylamino]-pyrimidine-4-carboxylic acid methyl ester,
6-[1-(4-bromo-3,5-diethoxy-benzyl)-piperidin-4-ylamino]-2-chloro-pyrimidine-4-carboxylic acid methyl ester,
2-chloro-6-[1-(3-ethoxy-4-iodo-5-methoxymethoxy-benzyl)-piperidin-4-ylamino]-pyrimidine-4-carboxylic acid methyl ester,
2-chloro-6-[1-(3,5-diethoxy-4-pyrrol-1-yl-benzyl)-piperidin-4-ylamino]-pyrimidine-4-carboxylic acid methyl ester,
2-chloro-6-[1-(2-chloro-3,5-diethoxy-benzyl)-piperidin-4-ylamino]-pyrimidine-4-carboxylic acid methyl ester,
2-chloro-6-[1-(3-ethoxy-4-methoxy-5-nitro-benzyl)-piperidin-4-ylamino]-pyrimidine-4-carboxylic acid methyl ester,
2-chloro-6-[1-(3-ethylamino-4-methoxy-benzyl)-piperidin-4-ylamino]-pyrimidine-4-carboxylic acid methyl ester,
N-{2-chloro-6-[1-(4-chloro-3-ethoxy-benzyl)-piperidin-4-ylamino]-pyrimidin-4-yl}-acetamide,
(2-chloro-5-fluoro-pyrimidin-4-yl)-[1-(3-ethoxy-4-methyl-benzyl)-piperidin-4-yl]-amine,
(2-chloro-5-fluoro-pyrimidin-4-yl)-[1-(3-ethoxy-4-fluoro-benzyl)-piperidin-4-yl]-amine,
[1-(4-chloro-3-ethoxy-benzyl)-piperidin-4-yl]-(2-chloro-5-fluoro-pyrimidin-4-yl)-amine,
(2-chloro-5-fluoro-pyrimidin-4-yl)-[1-(3-ethoxy-4-methoxy-benzyl)-piperidin-4-yl]-amine,
(2-chloro-5-fluoro-pyrimidin-4-yl)-[1-(3,4-diethoxy-benzyl)-piperidin-4-yl]-amine,
(2-chloro-5-fluoro-pyrimidin-4-yl)-[1-(3-ethoxy-4-isopropoxy-benzyl)-piperidin-4-yl]-amine,
(2-chloro-5-fluoro-pyrimidin-4-yl)-[1-(4-methoxy-3-propoxy-benzyl)-piperidin-4-yl]-amine,
(2-chloro-5-fluoro-pyrimidin-4-yl)-{1-[3-(2-fluoro-ethoxy)-4-methoxy-benzyl]-piperidin-4-yl}-amine,
(2-chloro-5-fluoro-pyrimidin-4-yl)-{1-[4-methoxy-3-(2,2,2-trifluoro-ethoxy)-benzyl]-piperidin-4-yl}-amine,
[1-(3-allyloxy-4-methoxy-benzyl)-piperidin-4-yl]-(2-chloro-5-fluoro-pyrimidin-4-yl)-amine,
[1-(3-butoxy-4-methoxy-benzyl)-piperidin-4-yl]-(2-chloro-5-fluoro-pyrimidin-4-yl)-amine,
(2-chloro-5-fluoro-pyrimidin-4-yl)-[1-(3-isobutoxy-4-methoxy-benzyl)-piperidin-4-yl]-amine,
(2-chloro-5-fluoro-pyrimidin-4-yl)-[1-(3,5-diethoxy-benzyl)-piperidin-4-yl]-amine,
(2-chloro-5-fluoro-pyrimidin-4-yl)-[1-(3,5-diisopropoxy-benzyl)-piperidin-4-yl]-amine,
(2-chloro-5-fluoro-pyrimidin-4-yl)-[1-(3,5-diethoxy-4-fluoro-benzyl)-piperidin-4-yl]-amine,
[1-(4-chloro-3,5-diethoxy-benzyl)-piperidin-4-yl]-(2-chloro-5-fluoro-pyrimidin-4-yl)-amine,
[1-(4-bromo-3,5-diethoxy-benzyl)-piperidin-4-yl]-(2-chloro-5-fluoro-pyrimidin-4-yl)-amine,
(2-chloro-5-fluoro-pyrimidin-4-yl)-[1-(3,5-diethoxy-4-pyrrol-1-yl-benzyl)-piperidin-4-yl]-amine,
[1-(2-chloro-3,5-diethoxy-benzyl)-piperidin-4-yl]-(2-chloro-5-fluoro-pyrimidin-4-yl)-amine,
(2-chloro-5-methoxy-pyrimidin-4-yl)-[1-(3-ethoxy-4-methyl-benzyl)-piperidin-4-yl]-amine,
(2-chloro-5-methoxy-pyrimidin-4-yl)-[1-(3-ethoxy-4-fluoro-benzyl)-piperidin-4-yl]-amine,
[1-(4-chloro-3-ethoxy-benzyl)-piperidin-4-yl]-(2-chloro-5-methoxy-pyrimidin-4-yl)-amine,
4-[4-(2-chloro-5-methoxy-pyrimidin-4-ylamino)-piperidin-1-ylmethyl]-2-ethoxy-phenol,
(2-chloro-5-methoxy-pyrimidin-4-yl)-[1-(3-ethoxy-4-methoxy-benzyl)-piperidin-4-yl]-amine,
(2-chloro-5-methoxy-pyrimidin-4-yl)-[1-(3-ethoxy-4-isopropoxy-benzyl)-piperidin-4-yl]-amine,
(2-chloro-5-methoxy-pyrimidin-4-yl)-{1-[3-ethoxy-4-(1-ethyl-propoxy)-benzyl]-piperidin-4-yl}-amine,
(2-chloro-5-methoxy-pyrimidin-4-yl)-[1-[3-(2-fluoro-ethoxy)-4-methoxy-benzyl]-piperidin-4-yl]-amine,
[1-(3-allyloxy-4-methoxy-benzyl)-piperidin-4-yl]-(2-chloro-5-methoxy-pyrimidin-4-yl)-amine,
[1-(3-butoxy-4-methoxy-benzyl)-piperidin-4-yl]-(2-chloro-5-methoxy-pyrimidin-4-yl)-amine,
(2-chloro-5-methoxy-pyrimidin-4-yl)-[1-(8-ethoxy-2,2-dimethyl-2H-chromen-6-ylmethyl)-piperidin-4-yl]-amine,
(2-chloro-5-methoxy-pyrimidin-4-yl)-[1-(3,5-diethoxy-benzyl)-piperidin-4-yl]-amine,
(2-chloro-5-methoxy-pyrimidin-4-yl)-[1-(3,5-diisopropoxy-benzyl)-piperidin-4-yl]-amine,
3-[4-(2-chloro-5-methoxy-pyrimidin-4-ylamino)-piperidin-1-ylmethyl]-5-isopropoxy-phenol, (2-chloro-5-methoxy-pyrimidin-4-yl)-[1-(3,5-diethoxy-4-fluoro-benzyl)-piperidin-4-yl]-amine,
[1-(4-chloro-3,5-diethoxy-benzyl)-piperidin-4-yl]-(2-chloro-5-methoxy-pyrimidin-4-yl)-amine,
[1-(4-bromo-3,5-diethoxy-benzyl)-piperidin-4-yl]-(2-chloro-5-methoxy-pyrimidin-4-yl)-amine,
[1-(4-amino-3,5-diethoxy-benzyl)-piperidin-4-yl]-(2-chloro-5-methoxy-pyrimidin-4-yl)-amine,
(2-chloro-5-methoxy-pyrimidin-4-yl)-[1-(3,5-diethoxy-4-pyrrol-1-yl-benzyl)-piperidin-4-yl]-amine,
[1-(2-chloro-3,5-diethoxy-benzyl)-piperidin-4-yl]-(2-chloro-5-methoxy-pyrimidin-4-yl)-amine,
(2-chloro-6,7-dihydro-5H-cyclopentapyrimidin-4-yl)-[1-(3-ethoxy-4-fluoro-benzyl)-piperidin-4-yl]-amine,
(2-chloro-6,7-dihydro-5H-cyclopentapyrimidin-4-yl)-[1-(4-chloro-3-ethoxy-benzyl)-piperidin-4-yl]-amine,
4-[4-(2-chloro-6,7-dihydro-5H-cyclopentapyrimidin-4-ylamino)-piperidin-1-ylmethyl]-2-ethoxy-phenol,
(2-chloro-6,7-dihydro-5H-cyclopentapyrimidin-4-yl)-[1-(3-ethoxy-4-methoxy-benzyl)-piperidin-4-yl]-amine,
(2-chloro-6,7-dihydro-5H-cyclopentapyrimidin-4-yl)-[1-(3-ethoxy-4-isopropoxy-benzyl)-piperidin-4-yl]-amine,
(2-chloro-6,7-dihydro-5H-cyclopentapyrimidin-4-yl)-{1-[3-ethoxy-4-(1-ethyl-propoxy)-benzyl]-piperidin-4-yl}-amine,
methanesulfonic acid 4-[4-(2-chloro-6,7-dihydro-5H-cyclopentapyrimidin-4-ylamino)-piperidin-1-ylmethyl]-2-ethoxy-phenyl ester,
(2-chloro-6,7-dihydro-5H-cyclopentapyrimidin-4-yl)-{1-[3-(2-fluoro-ethoxy)-4-methoxy-benzyl]-piperidin-4-yl}-amine,
[1-(3-allyloxy-4-methoxy-benzyl)-piperidin-4-yl]-(2-chloro-6,7-dihydro-5H-cyclopentapyrimidin-4-yl)-amine,
[1-(3-butoxy-4-methoxy-benzyl)-piperidin-4-yl]-(2-chloro-6,7-dihydro-5H-cyclopentapyrimidin-4-yl)-amine,
(2-chloro-6,7-dihydro-5H-cyclopentapyrimidin-4-yl)-[1-(8-ethoxy-2,2-dimethyl-2H-chromen-6-ylmethyl)-piperidin-4-yl]-amine,
(2-chloro-6,7-dihydro-5H-cyclopentapyrimidin-4-yl)-[1-(3,5-diethoxy-benzyl)-piperidin-4-yl]-amine,
3-[4-(2-chloro-6,7-dihydro-5H-cyclopentapyrimidin-4-ylamino)-piperidin-1-ylmethyl]-5-isopropoxy-phenol,
(2-chloro-6,7-dihydro-5H-cyclopentapyrimidin-4-yl)-[1-(3,5-diisopropoxy-benzyl)-piperidin-4-yl]-amine,
[1-(3-benzyloxy-5-ethoxy-benzyl)-piperidin-4-yl]-(2-chloro-6,7-dihydro-5H-cyclopentapyrimidin-4-yl)-amine,
(2-chloro-6,7-dihydro-5H-cyclopentapyrimidin-4-yl)-[1-(3,5-diethoxy-4-fluoro-benzyl)-piperidin-4-yl]-amine,
(2-chloro-6,7-dihydro-5H-cyclopentapyrimidin-4-yl)-[1-(3,5-diethoxy-4-pyrrol-1-yl-benzyl)-piperidin-4-yl]-amine,
[1-(2-chloro-3,5-diethoxy-benzyl)-piperidin-4-yl]-(2-chloro-6,7-dihydro-5H-cyclopentapyrimidin-4-yl)-amine,
{2,4-dichloro-6-[1-(3,5-diisopropoxy-benzyl)-piperidin-4-ylamino]-pyrimidin-5-yl}-acetic acid ethyl ester,
{2,4-dichloro-6-[1-(3,5-diethoxy-4-fluoro-benzyl)-piperidin-4-ylamino]-pyrimidin-5-yl}-acetic acid ethyl ester,
{2,4-dichloro-6-[1-(4-chloro-3,5-diethoxy-benzyl)-piperidin-4-ylamino]-pyrimidin-5-yl}-acetic acid ethyl ester,
{4-[1-(4-amino-3,5-diethoxy-benzyl)-piperidin-4-ylamino]-2,6-dichloro-pyrimidin-5-yl}-acetic acid ethyl ester,
{2,4-dichloro-6-[1-(3,5-diethoxy-4-pyrrol-1-yl-benzyl)-piperidin-4-ylamino]-pyrimidin-5-yl}-acetic acid ethyl ester,
[1-(3-ethoxy-4-methyl-benzyl)-piperidin-4-yl]-(2,5,6-trichloro-pyrimidin-4-yl)-amine,
[1-(4-chloro-3-ethoxy-benzyl)-piperidin-4-yl]-(2,5,6-trichloro-pyrimidin-4-yl)-amine,
[1-(3-ethoxy-4-methoxy-benzyl)-piperidin-4-yl]-(2,5,6-trichloro-pyrimidin-4-yl)-amine,
{1-[3-(2-fluoro-ethoxy)-4-methoxy-benzyl]-piperidin-4-yl}-(2,5,6-trichloro-pyrimidin-4-yl)-amine,
[1-(3-isobutoxy-4-methoxy-benzyl)-piperidin-4-yl]-(2,5,6-trichloro-pyrimidin-4-yl)-amine,
[1-(3,5-diisopropoxy-benzyl)-piperidin-4-yl]-(2,5,6-trichloro-pyrimidin-4-yl)-amine,
[1-(4-chloro-3,5-diethoxy-benzyl)-piperidin-4-yl]-(2,5,6-trichloro-pyrimidin-4-yl)-amine,
[1-(3,5-diethoxy-4-pyrrol-1-yl-benzyl)-piperidin-4-yl]-(2,5,6-trichloro-pyrimidin-4-yl)-amine,
(7-chloro-quinazolin-4-yl)-[1-(3-ethoxy-4-methyl-benzyl)-piperidin-4-yl]-amine,
(7-chloro-quinazolin-4-yl)-[1-(3-ethoxy-4-fluoro-benzyl)-piperidin-4-yl]-amine,
4-[4-(7-chloro-quinazolin-4-ylamino)-piperidin-1-ylmethyl]-2-ethoxy-phenol,
(7-chloro-quinazolin-4-yl)-[1-(3,5-diethoxy-benzyl)-piperidin-4-yl]-amine,
(7-chloro-quinazolin-4-yl)-[1-(3,5-diisopropoxy-benzyl)-piperidin-4-yl]-amine,
(7-chloro-quinazolin-4-yl)-[1-(3,5-diethoxy-4-fluoro-benzyl)-piperidin-4-yl]-amine,
[1-(4-chloro-3,5-diethoxy-benzyl)-piperidin-4-yl]-(7-chloro-quinazolin-4-yl)-amine,
[1-(4-amino-3,5-diethoxy-benzyl)-piperidin-4-yl]-(7-chloro-quinazolin-4-yl)-amine,
(7-chloro-quinazolin-4-yl)-[1-(3,5-diethoxy-4-pyrrol-1-yl-benzyl)-piperidin-4-yl]-amine,
(2-chloro-6,7-dimethoxy-quinazolin-4-yl)-[1-(3-ethoxy-4-fluoro-benzyl)-piperidin-4-yl]-amine,
(2-chloro-6,7-dimethoxy-quinazolin-4-yl)-[1-(4-chloro-3-ethoxy-benzyl)-piperidin-4-yl]-amine,
(2-chloro-6,7-dimethoxy-quinazolin-4-yl)-[1-(3,5-diisopropoxy-benzyl)-piperidin-4-yl]-amine,
(2-chloro-6,7-dimethoxy-quinazolin-4-yl)-[1-(3,5-diethoxy-4-fluoro-benzyl)-piperidin-4-yl]-amine,
(2-chloro-6,7-dimethoxy-quinazolin-4-yl)-[1-(3,5-diethoxy-4-pyrrol-1-yl-benzyl)-piperidin-4-yl]-amine,
[1-(3-ethoxy-4-methyl-benzyl)-piperidin-4-yl]-(9H-purin-6-yl)-amine,
[1-(4-chloro-3-ethoxy-benzyl)-piperidin-4-yl]-(9H-purin-6-yl)-amine,
2-ethoxy-4-[4-(9H-purin-6-ylamino)-piperidin-1-ylmethyl]-phenol,
[1-(3-ethoxy-4-methoxy-benzyl)-piperidin-4-yl]-(9H-purin-6-yl)-amine,
[1-(3-ethoxy-4-isopropoxy-benzyl)-piperidin-4-yl]-(9H-purin-6-yl)-amine,
[1-(4-methoxy-3-propoxy-benzyl)-piperidin-4-yl]-(9H-purin-6-yl)-amine,
{1-[3-(2-fluoro-ethoxy)-4-methoxy-benzyl]-piperidin-4-yl}-(9H-purin-6-yl)-amine,
[1-(3-butoxy-4-methoxy-benzyl)-piperidin-4-yl]-(9H-purin-6-yl)-amine,
[1-(3-isobutoxy-4-methoxy-benzyl)-piperidin-4-yl]-(9H-purin-6-yl)-amine,
[1-(8-ethoxy-2,2-dimethyl-2H-chromen-6-ylmethyl)-piperidin-4-yl]-(9H-purin-6-yl)-amine,
[1-(3,5-diisopropoxy-benzyl)-piperidin-4-yl]-(9H-purin-6-yl)-amine,
[1-(4-chloro-3,5-diethoxy-benzyl)-piperidin-4-yl]-(9H-purin-6-yl)-amine,

[1-(3,5-diethoxy-4-pyrrol-1-yl-benzyl)-piperidin-4-yl]-(9H-purin-6-yl)-amine,
6-[1-(4-chloro-3-ethoxy-benzyl)-piperidin-4-ylamino]-pyrimidine-2,4-dicarboxylic acid,
and pharmaceutically acceptable salts thereof.

Especially preferred are the following compounds of formula I of the present invention:
[1-(4-chloro-3-ethoxy-benzyl)-piperidin-4-yl]-(2-chloro-pyrimidin-4-yl)-amine,
[1-(4-chloro-3-ethoxy-benzyl)-piperidin-4-yl]-(7-chloro-quinazolin-4-yl)-amine,
(6-chloro-5-o-tolyloxy-pyrimidin-4-yl)-[1-(3,5-diisopropoxy-benzyl)-piperidin-4-yl]-amine,
[6-chloro-5-(2-methoxy-phenoxy)-pyrimidin-4-yl]-[1-(3,5-diisopropoxy-benzyl)-piperidin-4-yl]-amine,
(2-chloro-pyrimidin-4-yl)-[1-(3,5-diisopropoxy-benzyl)-piperidin-4-yl]-amine,
[1-(4-chloro-3-ethoxy-benzyl)-piperidin-4-yl]-(2-chloro-6-methyl-pyrimidin-4-yl)-amine,
(2-chloro-6-methyl-pyrimidin-4-yl)-[1-(3,5-diisopropoxy-benzyl)-piperidin-4-yl]-amine,
[1-(4-chloro-3,5-diethoxy-benzyl)-piperidin-4-yl]-(2,6-dichloro-pyrimidin-4-yl)-amine,
2-chloro-6-[1-(3,5-diisopropoxy-benzyl)-piperidin-4-ylamino]-pyrimidine-4-carboxylic acid methyl ester,
[1-(4-chloro-3,5-diethoxy-benzyl)-piperidin-4-yl]-(2-chloro-5-fluoro-pyrimidin-4-yl)-amine,
(2-chloro-5-methoxy-pyrimidin-4-yl)-[1-(3,5-diisopropoxy-benzyl)-piperidin-4-yl]-amine,
[1-(4-chloro-3,5-diethoxy-benzyl)-piperidin-4-yl]-(2-chloro-5-methoxy-pyrimidin-4-yl)-amine,
(2-chloro-6,7-dihydro-5H-cyclopentapyrimidin-4-yl)-[1-(3,5-diethoxy-4-fluoro-benzyl)-piperidin-4-yl]-amine,
(7-chloro-quinazolin-4-yl)-[1-(3,5-diisopropoxy-benzyl)-piperidin-4-yl]-amine,
and pharmaceutically acceptable salts thereof.

Furthermore, the pharmaceutically acceptable salts of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of the general formula

G-X    II wherein G is as defined herein before and X is halogen, with a compound of the formula

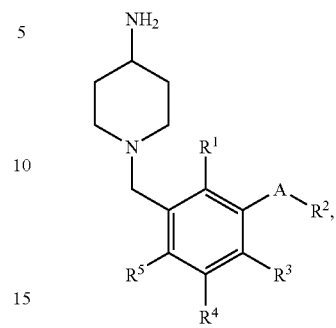

III wherein A and $R^1$ to $R^5$ are as defined herein before, to obtain a compound of the formula

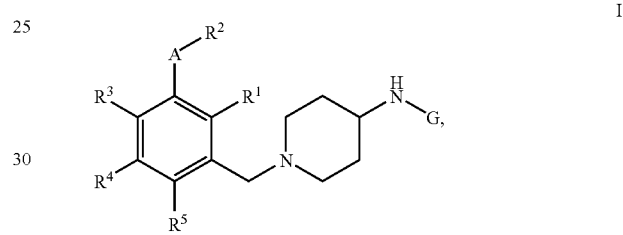

I and, if desired, converting the compound of formula I into a pharmaceutically acceptable salt; or, alternatively,
reacting a compound of the general formula

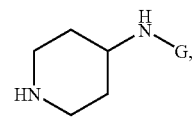

IV wherein G is as defined herein before,
with an aldehyde of the formula

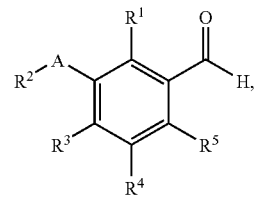

V wherein A and $R^1$ to $R^5$ are as defined herein before,
by employing a reducing agent to obtain a compound of the formula

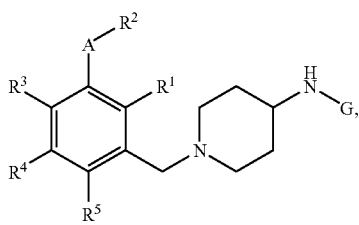

and, if desired, converting the compound of formula I into a pharmaceutically acceptable salt.

The invention further relates to compounds of formula I as defined above, when manufactured according to a process as defined above.

Suitable reducing agents are preferably selected from the group consisting of pyridine-$BH_3$ complex, $NaBH(OAc)_3$ and $NaCNBH_3$. The reaction can be carried out under acidic conditions by using an acid such as acetic acid or formic acid or an Lewis acid (e.g., $Ti(iPrO)_4$, $ZnCl_2$) or under basic conditions (no additive) in a suitable solvent such as dichloromethane, dichloroethane or ethanol (or mixtures thereof) at ambient or elevated temperatures using conventional heating or heating by microwave irradiation.

As described above, the compounds of formula I of the present invention can be used as medicaments for the treatment and/or prevention of diseases which are associated with the modulation of SST receptors subtype 5.

"Diseases which are associated with the modulation of SST receptors subtype 5" are such diseases as diabetes mellitus, particularly type II diabetes mellitus, impaired fasting glucose, impaired glucose tolerance, micro- and macrovascular diabetic complications, posttransplantation diabetes mellitus in patients having type I diabetes mellitus, gestational diabetes, obesity, inflammatory bowel diseases such as Crohn's disease or ulcerative colitis, malabsorption, autoimmune diseases such as rheumatoid arthritis, osteoarthritis, psoriasis and other skin disorder, and immunodeficiencies. Microvascular diabetic complications include diabetic nephropathy and diabetic retinopathy, whereas macrovascular diabetes-associated complications lead to an increased risk for myocardial infarction, stroke and limb amputations.

The use as medicament for the treatment and/or prevention of diabetes mellitus, particularly type II diabetes mellitus, impaired fasting glucose or impaired glucose tolerance is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of SST receptors subtype 5.

In another embodiment, the invention relates to a method for the treatment and/or prevention of diseases which are which are associated with the modulation of SST receptors subtype 5, which method comprises administering a compound of formula I to a human or animal. The method for the treatment and/or prevention of diabetes mellitus, particularly type II diabetes mellitus, impaired fasting glucose or impaired glucose tolerance, is most preferred.

The invention further relates to the use of compounds as defined above for the treatment and/or prevention of diseases which are associated with the modulation of SST receptors subtype 5.

In addition, the invention relates to the use of compounds as defined above for the preparation of medicaments for the treatment and/or prevention of diseases which are associated with the modulation of SST receptors subtype 5. Preferred examples of such diseases are diabetes mellitus, particularly type II diabetes mellitus, impaired fasting glucose or impaired glucose tolerance.

The compounds of formula I can be manufactured by the methods given below, by the methods given in the examples or by analogous methods. Appropriate reaction conditions for the individual reaction steps are standard reactions and are known to a person skilled in the art. Starting materials are either commercially available or can be prepared by methods analogous to the methods given below, by methods described in references cited in the text or in the examples, or by methods known in the art.

The synthesis of compounds with the general structure I, particularly compounds according to formula Ia to IId, are described in Schemes 1 to 11.

The synthesis of compounds of the general formula I, particularly compounds according to formula Ib can be accomplished according to Scheme 1.

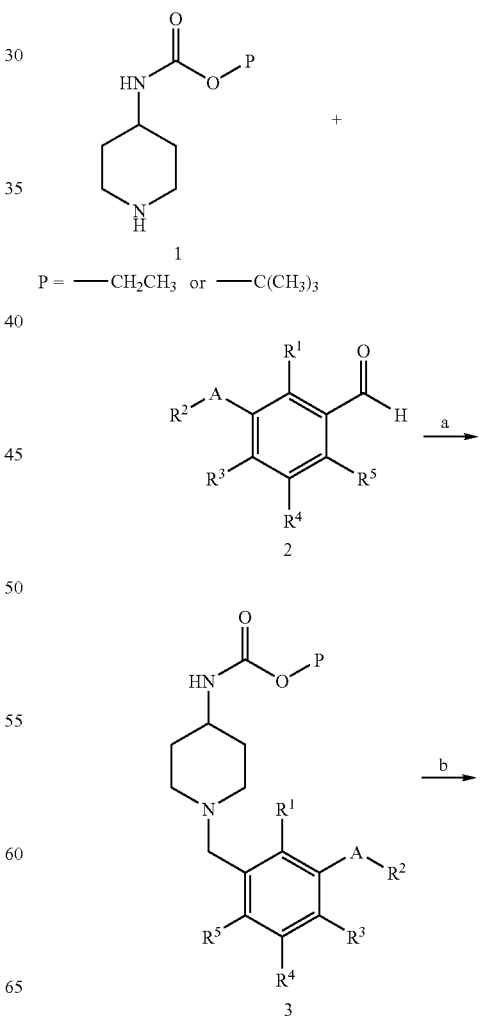

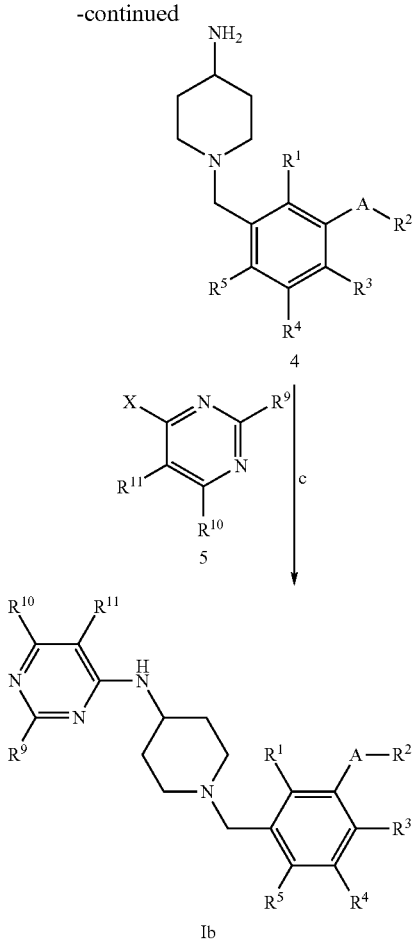

Reductive N-alkylation of suitably protected piperidines (for protecting groups see Protective Groups in Organic Synthesis, T. W. Greene, Wiley-Interscience 1999) of formula I with aldehydes 2 in the presence of a reducing agent such as pyridine-BH$_3$ complex, NaBH(OAc)$_3$ or NaCNBH$_3$ under acidic conditions (e.g., acetic acid, formic acid), by using a Lewis acid (e.g., Ti(iPrO)$_4$, ZnCl$_2$) or under buffered conditions, e.g., in the presence of acetic acid and a tertiary amine like N-ethyl-diisopropylamine or triethylamine in a suitable solvent such as dichloromethane, dichloroethane, ethanol or isopropanol (or mixtures thereof) at ambient or elevated temperatures using conventional heating or heating by microwave irradiation provide piperidines of general formula 3 (Scheme 1, step a). The piperidines of formula I may thereby used either as a salt, e.g., hydrochloride or hydrobromide salt, or as the corresponding free amine. The alkyloxycarbonyl protecting group present in compounds 3 can be removed, using e.g., 48% aqueous hydrogen bromide or 37% aqueous hydrochloric acid as reagent preferably at elevated temperatures to remove an ethyl carbamate or using trifluoroacetic acid or hydrochloric acid in a solvent like dichloromethane, dioxane or THF preferable at room temperature to remove a tert-butyloxycarbonyl (BOC)-protective group (see Protective Groups in Organic Synthesis, T. W. Greene, Wiley-Interscience 1999), yielding 4-amino piperidines of formula 4 (Scheme 1, step b).

Target compounds of formula I can be synthesized by nucleophilic replacement reaction of 4-amino piperidines of formula 4 and a variety of pyrimidines, quinazolines or purines of general structure 5 at room or elevated temperatures (Scheme 1, step c), whereby X is a suitable leaving group such as fluorine, chlorine, bromine or methyl sulfone. Thereby heating can be achieved conventionally or by microwave irradiation using a suitable microwave irradiation apparatus. Furthermore the reaction can be conducted in the presence of or without solvent (typically an aprotic polar solvent such as DMF (N,N-dimethylformamide), DMAc (dimethylacetamide), NMP (N-methylpyrrolidon), ethylene glycol, acetonitrile or THF) and in the presence of or without a tertiary amine base such as N-ethyl diisopropylamine, triethylamine or pyridine and in the presence with or without copper(I) bromide or copper(I) iodide. The starting materials and some of the intermediates of general structure 5 (e.g., 4-chloro-pyrimidines, 2,4-dichloro-pyrimidines, 4-chloro-quinazolines, 2,4-dichloro-quinazolines or 6-chloro-9H-purines) are known compounds and are commercially available or can be prepared by numerous methods using conventional reaction procedures generally known in the art. The 4-amino piperidines of formula 4 may thereby used either as a salt, e.g., hydrochloride or hydrobromide salt, or as the corresponding free amine. Alternatively the nucleophilic displacement reaction can be conducted under basic conditions by using K$_2$CO$_3$, KOH, NaOCH$_3$, KOtert-Bu or in particular by using NaH. If the coupling reaction is conducted with 2,4-dihalo-pyrimidines or 2,4-dihalo-quinazolines, preferentially with 2,4-dichloro-pyrimidines, regioisomeric coupling products might be obtained, which can be separated by conventional chromatographic methods. In cases where nucleophilic substitution leads to regioisomeric products the regiochemistry of target structures I was unambiguously established by means of nuclear magnetic resonance spectroscopy employing 1D-NOE difference, 2D-NOESY and/or $^{13}$C/$^1$HMBC experiments. In many cases $^1$H NMR spectra revealed the presence of tautomeric structures at room temperature (rt).

Alternatively target structures I can be achieved using Pd(0)-catalyzed amination reactions of 4-halo-pyrimidines, 2,4-dihalo-pyrimidines, 4-halo-quinazolines, 2,4-dihalo-quinazolines or 6-halo-9H-purines of formula 5 with 4-amino piperidines 4 (e.g., Buchwald-Hartwig coupling; see (a) J. P. Wolfe, S. Wagaw and S. L. Buchwald *J. Am. Chem. Soc.* 1996, 118, 7215-7216; (b) J. P. Wolfe and S. L. Buchwald *Tetrahedron Lett.* 1997, 38, 6359-6362; (c) J. P. Wolfe, S. Wagaw, J.-F. Marcoux and S. L. Buchwald *Acc. Chem. Res.* 1998, 31, 805-818; (d) B. H. Yang and S. L. Buchwald *J. Organomet. Chem.* 1999, 576, 125-146; (e) J. F. Hartwig *Angew. Chem. Int. Ed.* 1998, 37, 2046-2067). Thereby halo-substituted heterocyclic compounds 5 are reacted with amines 4 under an inert atmosphere such as argon or nitrogen in the presence of a palladium catalyst such as tris(dibenzylideneacetone)dipalladium(0) (Pd$_2$(dba)$_3$) or palladium(II) acetate (Pd(COOCH$_3$)$_2$), a phosphine ligand like triphenylphosphine, rac-2,2'-bis(diphenylphosphino)-1,1'-binaphthalene (rac-BINAP) or (R)-(−)-1-[(S)-2-(dicyclohexylphosphino)ferrocenyl]ethyldi-tert-butylphosphine (Josiphos; see Q. Shen, S. Shekhar, J. P. Stambuli and J. F. Hartwig *Angew. Chem. Int. Ed.* 2005, 44, 1371-1375) and a base such as Cs$_2$CO$_3$ or KOtert-Bu in a solvent like toluene, ethanol or water or mixtures thereof (Scheme 1, step c). Said C—N formation reaction may be conducted at room temperature or in order to enhance the rate of conversion at elevated temperatures, whereby heating might be achieved conventionally or by microwave irradiation (see also Palladium(0) Complexes in Organic Chemistry, in *Organometallics in Synthesis* (Ed. M. Schlosser), Chapter 4, 2$^{nd}$ Edition, 2002, John Wiley & Sons, Ltd, Chichester, UK).

Target structures of formula I can also be accomplished employing an inverted reaction sequence, namely by first coupling halo-substituted heterocycles 5 with alkyloxycarbonyl protected amine 6 (Scheme 2, step a). The protection group of piperidines 7 are then removed yielding the secondary amines 8 (Scheme 2, step b), which undergo reductive N-alkylation to target structures I (Scheme 2, step c). In contrast to the strategy outlined in Scheme 1, where the point of diversification is the heteroaryl moiety, this synthetic route is of particular interest if the variation of the benzyl moiety is aimed for in a rapid and parallel fashion.

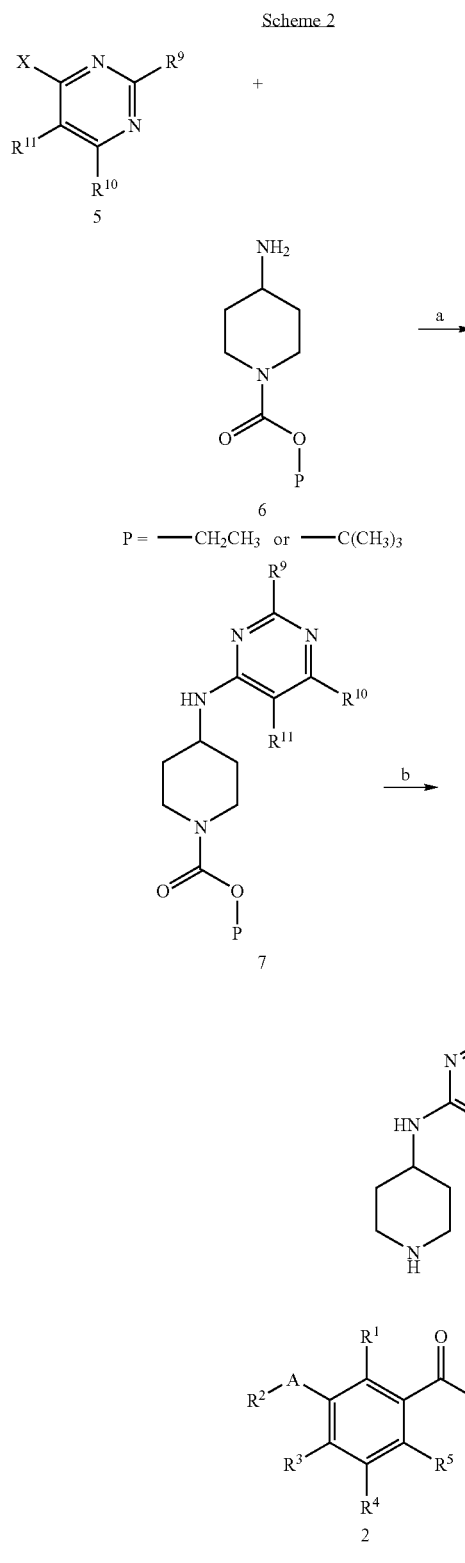

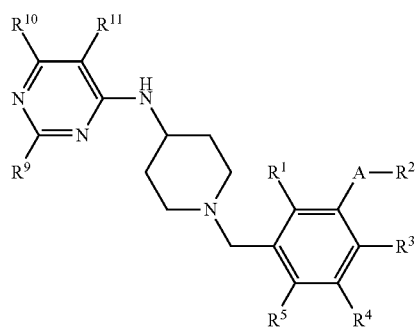

Target compounds of formula I might also be synthesized by direct alkylation of piperidines 8 with suitable halides, mesylates, tosylates or alcohols containing any other suitable leaving group of structure 9 in solvents such as N,N-dimethylformamide, dichloromethane, dichloroethane or acetone at ambient or elevated temperatures using conventional heating or heating by microwave irradiation with the addition of a suitable tertiary amine base (e.g., N-ethyl diisopropylamine, triethylamine) or an inorganic base (e.g., $Cs_2CO_3$, $K_2CO_3$) or by analogous alkylation reactions (Scheme 3, step a). Alternatively target structures of formula I might be accessible by Mitsunobu reaction (D. L. Hughes, The Mitsunobu Reaction, in *Organic Reactions, Volume* 42, 1992, John Wiley & Sons, New York; pp. 335-656) applying alcohols 10 activated by a mixture of triphenylphosphine and diethyl- or di-tert-butyl-azadicarboxylate (Scheme 3, step b).

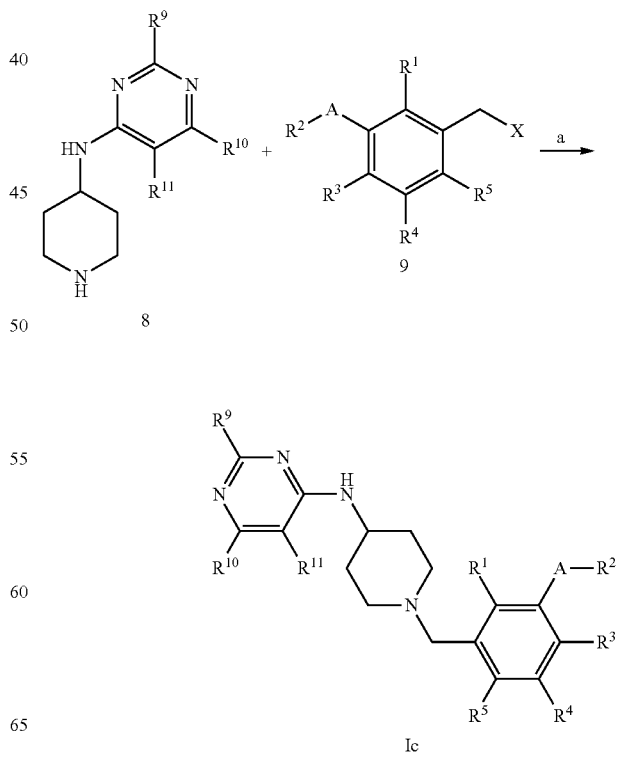

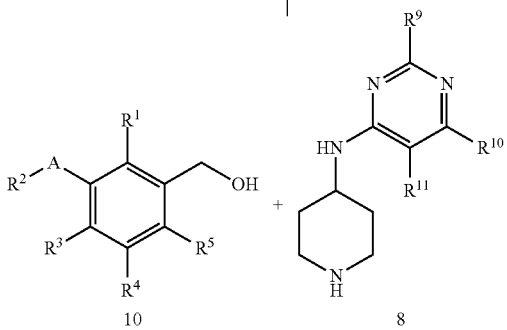

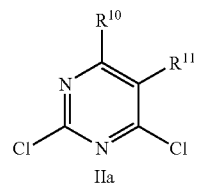

Synthesis of Pyrimidine and Quinazoline Intermediates

The starting materials of general formula IIa are either commercially available, known in the literature or can be obtained on application of classical methods of pyrimidine synthesis and subsequent functional group conversion such as by condensation of β-keto carboxylic acids 11 (malonic esters) with urea (12) as illustrated in step a of Scheme 4 (e.g., see Y.-Z. Kim, J.-C. Lim, J.-H. Yeo, C.-S. Bang, W.-S. Kim, S.-S. Kim, Y.-M. Woo, D.-H. Yang, H. Oh and K. Nahm *J. Med. Chem.* 1994, 37, 3828-3833). Halogenation of the pyrimidine intermediates 13 to provide compounds of general formula IIa can be accomplished in refluxing $POCl_3$ or $PCl_3/PCl_5$ (Scheme 4, step b; see also H. Krauch and W. Kunz, *Reaktionen der organischen Chemie*, 6., neubearbeitete Auflage, 1997, Hüthig GmbH, Heidelberg, Deutschland). The corresponding bromo derivatives of IIa are accessible when $POBr_3$ is used instead of $POCl_3$ as the halogenation agent. Furthermore, the halogenation step can be conducted in the presence or absence of catalytic amounts of N,N-dimethylaniline. All of these reactions are standard operations and can be carried out under conditions which are usual for such reactions and which are familiar to a person skilled in the art.

Alternatively, the preparation of target structures IIa can be achieved by condensation of β-keto carboxylic acids 11 (malonic esters) with guanidine (14) yielding 2-amino pyrimidines 15 (Traube synthesis; see A. R. Katritzky and T. I. Yousaf *Canad. J. Chem.* 1986, 64, 2087-2093; Scheme 5, step a). The 4-hydroxy group in pyrimidines 15 can then be converted to chloride employing standard halogenation conditions such as refluxing $POCl_3$ or $PCl_3/PCl_5$ (Scheme 5, step b). The 2-amino group in pyrimidines 16 can then be transformed to chloride employing standard Sandmeyer reaction conditions such as diazotization with sodium nitrite in the presence of hydrochloric acid at lower temperatures preferentially between –10° C. and 10° C. (Scheme 5, step c).

Scheme 5

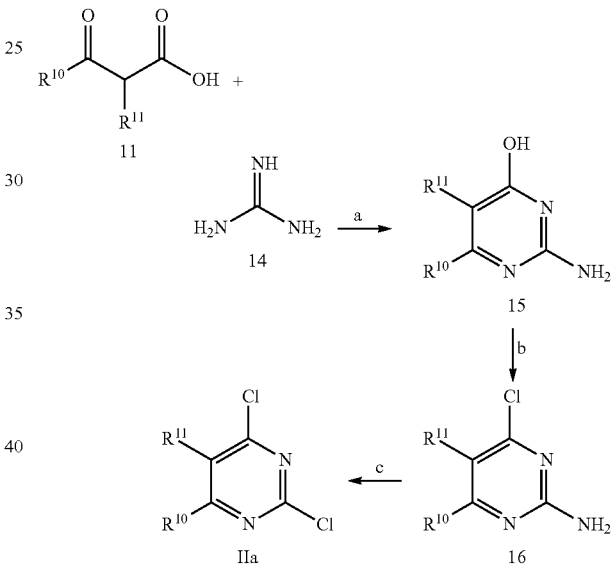

Scheme 4

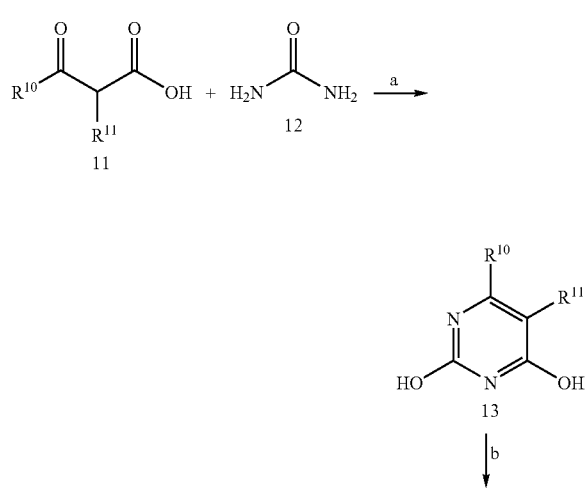

According to Scheme 6 target structures IIa can also be obtained by halogenation of uracils 17 with $POCl_3$ or $PCl_3/PCl_5$ (step a). This route is particularly amenable to pyrimidines with $R^1=R^2$=halogenes, such as fluoride or chloride.

Scheme 6

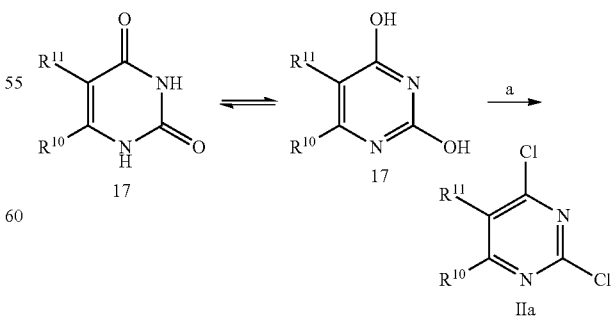

4,6-Dichloro-5-phenoxy-pyrimidine intermediates of general structure IIb can be obtained by the reaction sequence sketched hereinafter ($R^{21}$, $R^{22}$, $R^{23}$, $R^{24}$ and $R^{25}$ independently from each other are selected from the group consisting of hydrogen, $C_{1-7}$-alkyl and $C_{1-7}$-alkoxy). Alkylation of phenols 18 with 2-chloro-malonic acid diethyl ester (diethyl chloromalonate, 19) yields compounds 20 (Scheme 7, step a) which are condensed under basic conditions (e.g., sodium ethanolate) with formamidine acetate or homologous compounds 21 such as acetamidine acetate in a solvent like ethanol providing phenoxy pyrimidinedione derivatives 22 (Scheme 7, step b). Chlorination with $POCl_3$ or $PCl_3/PCl_5$ provides then compounds IIb (Scheme 7, step c).

nyl and the pyrimidine moiety can be achieved by a reaction sequence outlined in Scheme 8. Alkylation of benzylhalides 23 with malonic acid diethyl ester (24) provides compounds 25 (Scheme 8, step a), which alternatively can also be obtained by Knoevenagel condensation of benzaldehydes 26 with 24 (Scheme 8, step b). Conversion under basic conditions (e.g., sodium ethanolate) with formamidine acetate or homologous compounds 21 such as acetamidine acetate in a solvent like ethanol gives then access to the benzyl pyrimidinediones 27 (Scheme 8, step c). Chlorination of 27 with Scheme 7

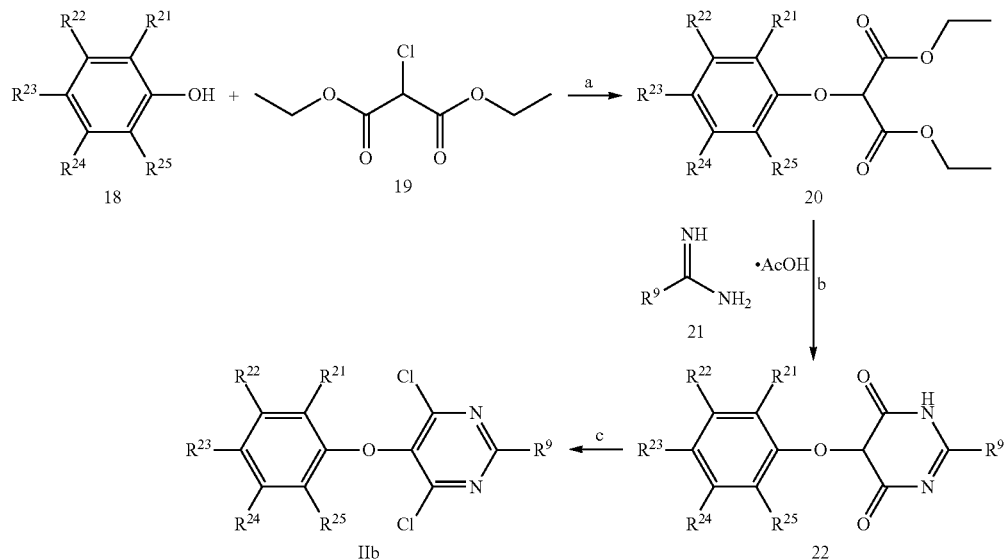

Synthesis of 5-benzyl-4,6-dichloro-pyrimidine intermediates IIc containing a carbon linker (Y=C) between the phenyl and the pyrimidine moiety can be achieved by a reaction sequence outlined in Scheme 8.

$POCl_3$ or $PCl_3/PCl_5$ provides then intermediates IIc (Scheme 8, step d).

Scheme 8

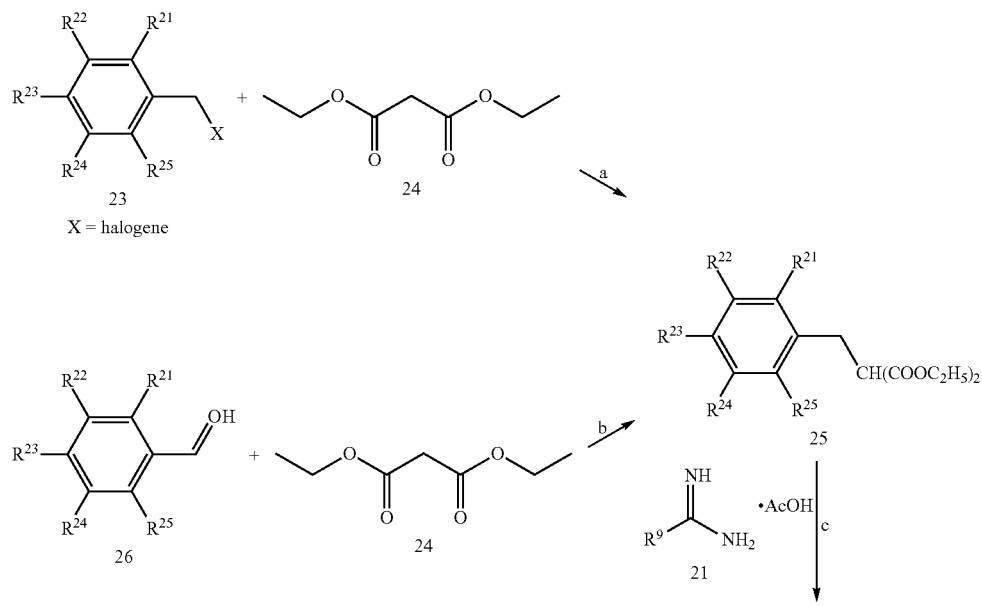

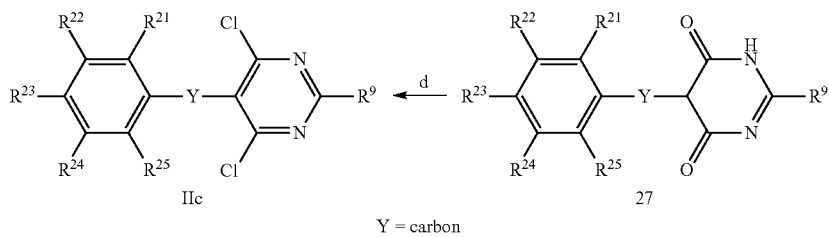

Y = carbon

There are myriads of references known in the art teaching methods useful for the preparation of pyrimidines. The reader is referred to (a) D. J. Brown, The Pyrimidines, in *The Chemistry of Heterocyclic Compounds* (Ed. A. Weissberger), Volume 16, 1962, Interscience Publishers, New York; (b) D. J. Brown, The Pyrimidines, in *The Chemistry of Heterocyclic Compounds* (Eds. A. Weissberger and E. C. Taylor), Volume 16, Supplement I, 1970, Interscience Publishers, New York; (c) D. J. Brown, R. F. Evans, W. B. Cowden and M. D. Fenn, The Pyrimidines, in *The Chemistry of Heterocyclic Compounds* (Eds. A. Weissberger and E. C. Taylor), Volume 16, Supplement II, 1985, Interscience Publishers, New York; (d) D. J. Brown, The Pyrimidines, in *The Chemistry of Heterocyclic Compounds* (Eds. A. Weissberger and E. C. Taylor), Volume 52, Supplement I, 1994, Interscience Publishers, New York; (e) L. A. Paquette, *Principles of Modern Heterocyclic Chemistry*, 1968, W. A. Benjamin, Inc., New York (uracil synthesis pp. 313-315; pyrimidine synthesis pp. 313-316); (f) *Comprehensive Organic Synthesis* (Eds. B. M. Trost and I. Fleming), 1992, Pergamon Press, Oxford, UK.

Further syntheses of pyrimidines of formula IIa-c are described in the examples.

The starting materials of general formula IId are either commercially available, known in the literature or can be obtained on application of classical methods of quinazoline synthesis. A classical route for the synthesis of quinazolines IId is outlined in Scheme 9. Condensation of anthranilic acids 28 and sodium or potassium cyanate in water and glacial acetic acid furnishes quinazoline-2,4-diols 29 (step a; see F. H. S. Curd, J. K. Landquist and F. L. Rose *J. Chem. Soc.* 1948, 1759-1766), which upon subsequent functional group conversion, e.g., treatment at elevated temperatures with phosphorus oxychloride in chloroform or neat and in the presence or absence of N,N-dimethylaniline as a catalyst, provide 2,4-dichloroquinazolines IId (step b). Alternatively, the cyclisation of anthranilic acids 28 to quinazoline-2,4-diols 29 can be achieved using urea preferably at elevated temperatures with or without solvent (see (a) E. H. Huntress and J. V. K. Gladding *J. Am. Chem. Soc.* 1942, 64, 2544-2649; (b) E. Cuny, F. W. Lichtenthaler and A. Moser *Tetrahedron Lett.* 1980, 21, 3029-3032).

Scheme 9

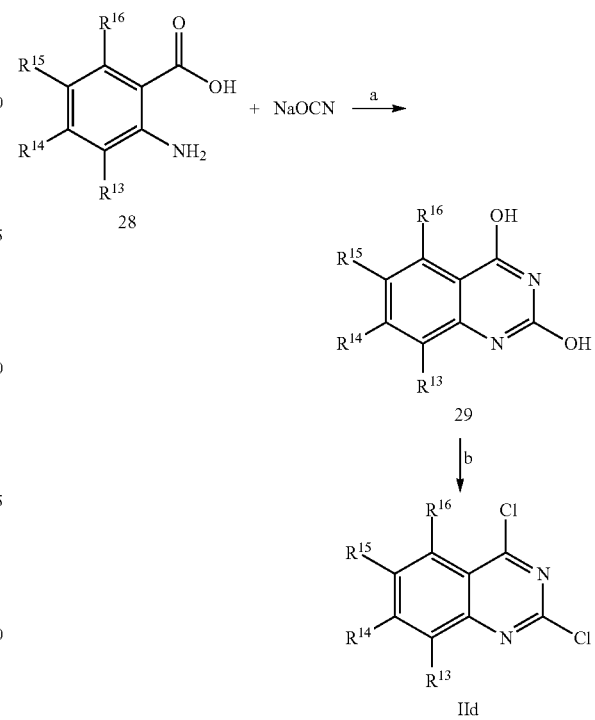

For the synthesis of 4-chloroquinazolines IIe anthranilic acids 28 are condensed preferentially neat with formamide at elevated temperatures using conventional heating or heating by microwave irradiation to yield directly quinazolin-4-ols 30 as outlined in Scheme 10 (step a; see (a) M. M. Endicott, E. Wick, M. L. Mercury and M. L. Sherrill *J. Am. Chem. Soc.* 1946, 68, 1299-1301; (b) C. C. Price, N. J. Leonard and D. Y. Curtin *J. Am. Chem. Soc.* 1946, 68, 1305-1306). Chlorination of 30 with $POCl_3$ or $PCl_3/PCl_5$ gives then straight access to the desired intermediates IIe (Scheme 10, step b).

Scheme 10

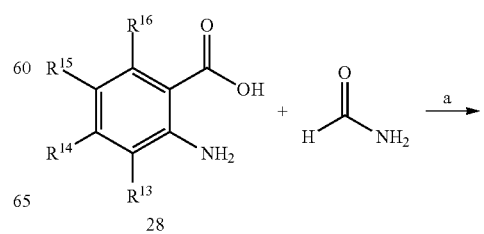

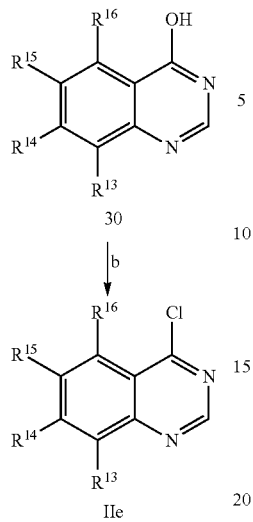

Most of the synthetic routes outlined in Scheme 4 to Scheme 10 are amenable to both solution and solid-phase synthesis (see J. T. Bork, J. W. Lee and Y.-T. Chang *QSAR Comb. Sci.* 2004, 23, 245-260).

The two halogen groups in pyrimidines and quinazolines IIa-d exhibit different chemical reactivity, with the chloride at the C2 position being inherently less reactive. This allows the sequential replacement of first the C4 and second the C2 chloride atom, e.g., by nucleophilic substitution reactions with amines or aliphatic or aromatic alcohols or by Pd(0)-catalyzed Suzuki, Buchwald-Hartwig or Stille-type coupling reactions, providing access to a large number of differently substituted intermediates of general structure IIa-d. The regiochemistry of target structures IIa-d was unambiguously established by means of nuclear magnetic resonance spectroscopy employing 1D-NOE difference, 2D-NOESY and/or $^{13}C/^{1}HMBC$ experiments.

Further syntheses of quinazolines of formula IId are described in the examples.

Synthesis of Aldehyde Intermediates

The requisite aldehyde partners are either commercially available or can be derived by alkylation with alkyl halides, alkyl mesylates, alkyl tosylates or alcohols containing any other suitable leaving group in a polar solvent such as DMF or acetone and a suitable base (e.g., $Cs_2CO_3$, $K_2CO_3$) at room temperature or elevated temperatures, by Mitsunobu reaction with alcohols activated by a mixture of triphenylphosphine and diethylazadicarboxylate, or by analogous alkylation of the phenolic carboxylic esters or acids of formula 31 (Scheme 10, step a). Reduction of the esters of formula 32 by a suitable reducing agent (e.g., diisobutylaluminium hydride at low temperature, with $LiAlH_4$ at elevated or ambient temperature) in a solvent such as THF provides the corresponding benzylalcohols of formula 33 (Scheme 11, step b). These can then be oxidized to the aldehydes of formula 34, preferably with activated $MnO_2$ as oxidant in dichloromethane (Scheme 11, step c).

Alternatively the introduction of the side-chain can be accomplished by direct alkylation (sequential for unsymmetrical compounds) of the phenolic benzaldehydes of formula 35 providing the desired compounds of formula 34 directly (Scheme 11, step d).

A further well-established route towards the synthesis of benzylaldehydes of formula 37 consists in the reduction of the corresponding benzonitriles of formula 36 by a suitable reducing agent such as diisobutylaluminium hydride at low temperature in a non-protic polar solvent (e.g., THF; Scheme 11, step e).

Scheme 11

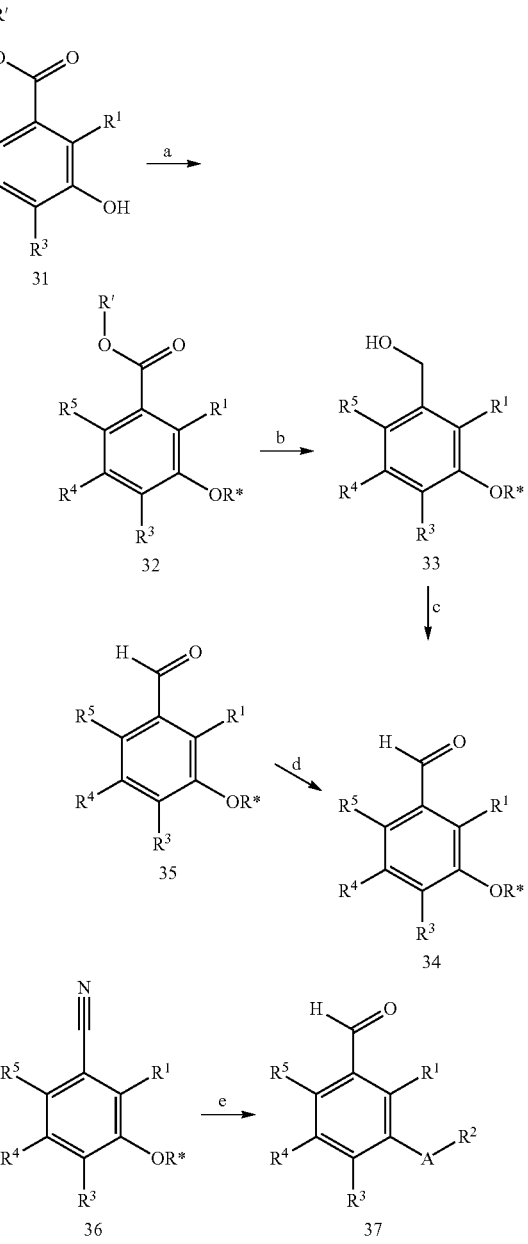

Additional syntheses of aldehydes of formula III are described in the examples.

As described hereinbefore, it has been found that the compounds of formula I possess pharmaceutical activity, in particular they are modulators of somatostatin receptor activity. More particularly, the compounds of the present invention have been found to be antagonists of the somatostatin receptor subtype 5 (SSTR5).

The following tests were carried out in order to determine the activity of the compounds of formula I.

A CHO cell line stably transfected with a plasmid encoding the human subtype 5 somatostatin receptor (GenBank accession number D16827) was obtained from Euroscreen. Cells were cultured and used for binding and functional assays.

Membranes of these cells were prepared by sonication in the presence of protease inhibitors and subsequent fractionating centrifugation. The protein concentration in the membrane preparation was determined using a commercial kit (BCA kit, Pierce, USA). Membranes were stored at −80° C. until use. After thawing, membranes were diluted in assay buffer (50 mM Tris-HCl at pH 7.4, 5 mM $MgCl_2$ and 0.20% BSA) and subjected to dounce homogenization.

For binding studies, 0.1 mL membrane suspension, corresponding to app. $6\times10^{-15}$ mol receptor, was incubated for 1 h at room temperature with 0.05 nM $^{125}$I-labeled tracer (11-Tyr somatostatin-14, Perkin-Elmer) and either test compounds in varying concentrations or, for the determination of non-specific binding, 0.001 mM non-labeled somatostatin-14. The incubation was stopped by filtration through GF/B glassfiber filters and washing with ice-cold wash buffer (50 mM Tris-HCl at pH 7.4). The bound radioactivity was measured after application of a scintillation cocktail (Microscint 40) and expressed as disintegrations per minute (dpm).

The receptor concentration was determined in a prior saturation experiment where a fixed, arbitrary amount of membranes was incubated with a concentration range of radiolabeled tracer. This allows estimating the total number of specific binding sites per amount of protein (i.e., $B_{max}$), typically between 1 and 5 pmol/mg.

The concentration of the test compound required to result in half maximal inhibition of binding of the radio-labeled tracer ($IC_{50}$) was estimated from a concentration-versus-dpm graph. The binding affinity ($K_i$) was calculated from the $IC_{50}$ by applying the Cheng-Prussoff equation for single binding sites.

For functional experiments, 50,000 cells were incubated in Krebs Ringer HEPES buffer (115 mM NaCl, 4.7 mM KCl, 2.56 mM $CaCl_2$, 1.2 mM $KH_2PO_4$, 1.2 mM $MgSO_4$, 20 mM $NaHCO_3$ and 16 mM HEPES, adjusted to pH 7.4) supplemented with 1 mM IBMX and 0.1% BSA, then stimulated with 0.004 mM forskolin. Simultaneously with forskolin, test compounds in varying concentrations were applied. Cells were then incubated for 20 min at 37° C. and 5% $CO_2$. Subsequently, cells were lysed and cAMP concentration measured using a fluorescence-based commercial kit according to the manufacturer (HitHunter cAMP, DiscoverX).

The concentration of the test compound to induce a half maximal effect (i.e., $EC_{50}$) as well as the efficacy as compared to 0.15 nM somatostatin-14 were determined from concentration-versus-fluorescence (arbitrary units) graphs. For the determination of potential antagonism, 0.15 nM somatostatin-14 was applied together with the test compounds and the concentration of the test compounds to half maximally reverse the effect of somatostatin-14 (i.e., $IC_{50}$) were deduced from concentration-versus-fluorescence graphs.

The compounds of the present invention exhibit $K_i$ values of 0.1 nM to 10 µM, preferably $K_i$ values of 1 nM to 500 nM and more preferably 0.1 nM to 100 nM for human subtype 5 somatostatin receptor. The following table shows measured values for selected compounds of the present invention.

|  | SSTR5 $K_i$ (nmol/l) |
| --- | --- |
| Example 15 | 383 |
| Example 23 | 2 |
| Example 147 | 78 |

The compounds of formula I and their pharmaceutically acceptable salts and esters can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or infusion solutions, or topically, e.g., in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The present invention will be further explained by reference to the following illustrative examples. They are, however, not intended to limit its scope in any manner.

EXAMPLES

Abbreviations

Ar=argon, DMAc=dimethylacetamide, DMF=N,N-dimethylformamide, DMSO=dimethyl sulfoxide, EI=electron impact (ionization), ESI=electron spray ionisation, HPLC=high performance liquid chromatography, Hyflo Super Gel®=filtration aid (Fluka), ISN=ion spray negative (mode), ISP=ion spray positive (mode), NMP=N-methylpyrrolidon, NMR=nuclear magnetic resonance, MPLC=medium pressure liquid chromatography, MS=mass spectrum, P=protecting group, R=any group, rt=room temperature, THF=tetrahydrofuran, X=halogen, Y=any group including heteroatoms and halides.

Example 1

(2-Chloro-pyrimidin-4-yl)-[1-(3-ethoxy-4-methoxy-benzyl)-piperidin-4-yl]-amine

Step 1

[1-(3-Ethoxy-4-methoxy-benzyl)-piperidin-4-yl]-carbamic acid tert-butyl ester

A mixture of piperidin-4-yl-carbamic acid tert-butyl ester (10.0 g, 50.0 mmol, 1.0 equiv), 3-ethoxy-4-methoxy-benzaldehyde (10.8 g, 60.0 mmol, 1.2 equiv; commercially available) and acetic acid (11.4 mL, 12.01 g, 200.0 mmol, 4.0 equiv) in ethanol (40 mL) was heated by microwave irradiation to 100° C. for 5 min. Sodium cyanoborohydride (6.27 g, 100.0 mmol, 2.0 equiv), dissolved in ethanol (20 mL), was added and the reaction mixture heated by microwave irradiation to 100° C. for an additional time period of 5 min. The solvent was removed under reduced pressure and the crude reaction product extracted from a solution of 1 M NaOH (200 mL) with ethyl acetate (3×100 mL). The combined organic phases were dried over MgSO$_4$, concentrated by evaporation under reduced pressure and the crude material purified with column chromatography on silica eluting with ethyl acetate to yield 9.71 g (53%) of the title compound as a white solid. MS (ISP): 365.3 [M+H]$^+$.

Step 2

1-(3-Ethoxy-4-methoxy-benzyl)-piperidin-4-ylamine (Intermediate A1)

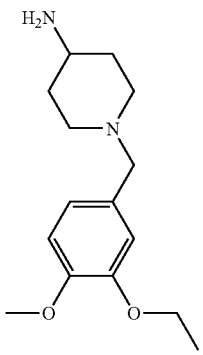

A solution of [1-(3-ethoxy-4-methoxy-benzyl)-piperidin-4-yl]-carbamic acid tert-butyl ester (9.71 g, 26.64 mmol) in ethanol (50 mL) and 4 M HCl in dioxane (75 mL) was stirred at rt for 2 h. The hydrochloric acid was removed under reduced pressure and the crude reaction product extracted from a solution of 1 M NaOH (200 mL) with ethyl acetate (3×100 mL). The combined organic phases were dried over MgSO$_4$ and concentrated by evaporation under reduced pressure yielding 4.69 g (89%) of a white solid. The crude material was directly used in the following reaction step. MS (ESI): 265.0 [M+H]$^+$.

Step 3 (Method A)

To a solution of 1-(3-ethoxy-4-methoxy-benzyl)-piperidin-4-ylamine (39.7 mg, 0.15 mmol, 1.2 equiv; intermediate A1) in dry DMF (1.5 mL) under Ar was added sodium hydride (6.6 mg, 0.15 mmol, 1.2 equiv; 55% free-flowing powder moistened with oil) and the reaction mixture stirred at rt. After 2 h, 2,4-dichloro-pyrimidine (18.6 mg, 0.125 mmol, 1.0 equiv; commercially available) was added and the mixture heated by microwave irradiation to 140° C. for 1 h. Removal of the solvent under reduced pressure and purification by preparative HPLC on reversed phase eluting with a gradient of acetonitrile/water provided 10.9 mg (23%) of the title compound. MS (ISP): 377.2 [M+H]$^+$.

Example 2

2-Chloro-N-[1-(3-ethoxy-4-methoxy-benzyl)-piperidin-4-yl]-N'-isopropyl-pyrimidine-4,6-diamine Step 1

(2,6-Dichloro-pyrimidin-4-yl)-isopropyl-amine [CAS RN 30297-43-9]

The title compound was prepared according to DE 2006 145 A1 (Sandoz A G).

Step 2 (Method B)

To a solution of 1-(3-ethoxy-4-methoxy-benzyl)-piperidin-4-ylamine (39.7 mg, 0.15 mmol, 1.2 equiv; intermediate A1) in dry DMF (1.5 mL) was added sodium hydride (6.6 mg, 0.15 mmol, 1.2 equiv; 55% free-flowing powder moistened with oil) and the reaction mixture stirred at rt under Ar. After 2 h, (2,6-dichloro-pyrimidin-4-yl)-isopropyl-amine (25.8 mg, 0.125 mmol, 1.0 equiv) was added and the mixture heated to 120° C. for 48 h. Removal of the solvent under reduced pressure and purification by preparative HPLC on reversed phase eluting with a gradient of acetonitrile/water provided 7.1 mg (13%) of the title compound. MS (ISP): 434.3 [M+H]$^+$.

Example 3

(2-Chloro-5-methyl-pyrimidin-4-yl)-[1-(3-ethoxy-4-methoxy-benzyl)-piperidin-4-yl]-amine Method C A solution of 2,4-dichloro-5-methyl-pyrimidine (16.3 mg, 0.10 mmol, 1.0 equiv; commercially available) and 1-(3-ethoxy-4-methoxy-benzyl)-piperidin-4-ylamine (39.7 mg, 0.15 mmol, 1.5 equiv; intermediate A1) in ethylene glycol (2 mL) was heated by microwave irradiation to 200° C. for 15 min. Removal of the solvent under reduced pressure and purification by preparative HPLC on reversed phase eluting with a gradient of acetonitrile/water provided 4.0 mg (7%) of the title compound. MS (ESI): 391.4 [M+H]$^+$.

Example 4

N-{2-Chloro-6-[1-(3-ethoxy-4-methoxy-benzyl)-piperidin-4-ylamino]-pyrimidin-4-yl}-acetamide Step 1

N-(2,6-Dichloro-pyrimidin-4-yl)-acetamide (Intermediate B1) [CAS RN 89581-87-3]

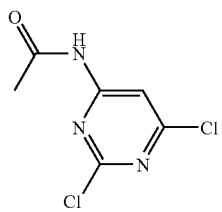

The title compound was prepared according to WO 05/026 149 A1 (AstraZeneca UK Limited).

Step 2 (Method D)

A solution of N-(2,6-dichloro-pyrimidin-4-yl)-acetamide (30.9 mg, 0.15 mmol, 1.0 equiv) and 1-(3-ethoxy-4-methoxy-benzyl)-piperidin-4-ylamine (47.6 mg, 0.18 mmol, 1.2 equiv; intermediate A1) in DMAc (2 mL) was heated by microwave irradiation to 180° C. for 15 min. Removal of the solvent under reduced pressure and purification by preparative HPLC on reversed phase eluting with a gradient of acetonitrile/water provided 1.6 mg (3%) of the title compound. MS (ISP): 434.4 [M+H]$^+$.

Example 5

N$^4$-[1-(3-ethoxy-4-methoxy-benzyl)-piperidin-4-yl]-6-methyl-pyrimidine-2,4-diamine Method E A solution of 4-chloro-6-methyl-pyrimidin-2-ylamine (21.5 mg, 0.15 mmol, 1.0 equiv; commercially available) and 1-(3-ethoxy-4-methoxy-benzyl)-piperidin-4-ylamine (47.6 mg, 0.18 mmol, 1.2 equiv; intermediate A1) in DMAc (2 mL) was heated by microwave irradiation to 180° C. for 40 min. Removal of the solvent under reduced pressure and purification by preparative HPLC on reversed phase eluting with a gradient of acetonitrile/water provided 6.1 mg (11%) of the title compound. MS (ISP): 372.3 [M+H]$^+$.

Example 6

(2,7-Dichloro-quinazolin-4-yl)-[1-(3-ethoxy-4-methoxy-benzyl)-piperidin-4-yl]-amine Step 1

2,4,7-Trichloro-quinazoline [CAS RN 6625-94-1]

The title compound was prepared according to WO 05/049 033 A1 (Astra Zeneca UK Limited).

Step 2 (Method F)

A solution of 2,4,7-trichloro-quinazoline (35.0 mg, 0.15 mmol, 1.0 equiv) and 1-(3-ethoxy-4-methoxy-benzyl)-piperidin-4-ylamine (47.6 mg, 0.18 mmol, 1.2 equiv; intermediate A1) in DMAc (2 mL) was heated by microwave irradiation to 200° C. for 30 min. Removal of the solvent under reduced pressure and purification by preparative HPLC on reversed phase eluting with a gradient of acetonitrile/water provided 1.8 mg (3%) of the title compound. MS (ISP): 461.3 [M+H]$^+$.

Example 7

[1-(3-Ethoxy-4-methoxy-benzyl)-piperidin-4-yl]-(2-phenyl-quinazolin-4-yl)-amine

Method G

A solution of 4-chloro-2-phenyl-quinazoline (36.1 mg, 0.15 mmol, 1.0 equiv; commercially available) and 1-(3-ethoxy-4-methoxy-benzyl)-piperidin-4-ylamine (47.6 mg, 0.18 mmol, 1.2 equiv; intermediate A1) in DMAc (1.5 mL) was heated by microwave irradiation to 180° C. for 10 min. Removal of the solvent under reduced pressure and purification by preparative HPLC on reversed phase eluting with a gradient of acetonitrile/water provided 1.6 mg (3%) of the title compound. MS (ISP): 469.4 [M+H]$^+$.

The pyrimidine and quinazoline intermediates B2 and B3 were prepared following literature precedents.

Synthesis of Pyrimidine and Quinazoline Intermediates B2 and B3 to be Used in Table 1

Intermediate B2

4-Azetidin-1-yl-2,6-dichloro-pyrimidine [CAS RN 202467-33-2]

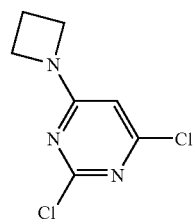

The title compound was prepared according to EP 0815 861 A1 (F. Hoffmann-La Roche A G).

Intermediate B3

2,4,7-Trichloro-6-fluoro-quinazoline [CAS RN 174866-16-6]

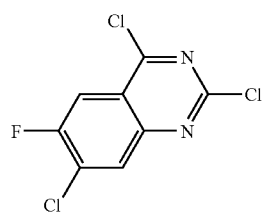

The title compound was prepared according to WO 95/32 205 A1 (F. Hoffmann-La Roche A G).

Examples 8 to 16

According to the procedure described for the synthesis of example 1/step 3 (Method A), example 2/step 2 (Method B), example 3 (Method C) and example 4/step 2 (Method D) further pyrimidine and quinazoline derivatives have been synthesized from 1-(3-ethoxy-4-methoxy-benzyl)-piperidin-4-ylamine (intermediate A1) and the respective pyrimidine and quinazoline intermediate as indicated in Table 1. The results are compiled in Table 1 and comprise example 8 to example 16.

TABLE 1

| No | MW | Compound Name | Preparation | Starting Materials | ISP [M + H]$^+$ found |
|---|---|---|---|---|---|
| 8 | 394.88 | (2-chloro-5-fluoro-pyrimidin-4-yl)-[1-(3-ethoxy-4-methoxy-benzyl)-piperidin-4-yl]-amine | Method A | 1-(3-ethoxy-4-methoxy-benzyl)-piperidin-4-ylamine (intermediate A1) and 2,4-dichloro-5-fluoro-pyrimidine (commercially available) | 395.3 |
| 9 | 411.33 | (2,6-dichloro-pyrimidin-4-yl)-[1-(3-ethoxy-4-methoxy-benzyl)-piperidin-4-yl]-amine | Method A | 1-(3-ethoxy-4-methoxy-benzyl)-piperidin-4-ylamine (intermediate A1) and 2,4,6-trichloro-pyrimidine (commercially available) | 411.1 |
| 10 | 445.78 | [1-(3-ethoxy-4-methoxy-benzyl)-piperidin-4-yl]-(2,5,6-trichloro-pyrimidin-4-yl)-amine | Method A | 1-(3-ethoxy-4-methoxy-benzyl)-piperidin-4-ylamine (intermediate A1) and 2,4,5,6-tetrachloro-pyrimidine (commercially available) | 447.0 |
| 11 | 391.90 | 6-chloro-N$^4$-[1-(3-ethoxy-4-methoxy-benzyl)-piperidin-4-yl]-pyrimidine-2,4-diamine | Method A | 1-(3-ethoxy-4-methoxy-benzyl)-piperidin-4-ylamine (intermediate A1) and 4,6-dichloro-pyrimidin-2-ylamine (commercially available) | 392.2 |
| 12 | 391.90 | 6-chloro-N$^4$-[1-(3-ethoxy-4-methoxy-benzyl)-piperidin-4-yl]-pyrimidine-4,5-diamine | Method A | 1-(3-ethoxy-4-methoxy-benzyl)-piperidin-4-ylamine (intermediate A1) and 4,6-dichloro-pyrimidin-5-ylamine (commercially available) | 392.2 |
| 13 | 431.97 | (6-azetidin-1-yl-2-chloro-pyrimidin-4-yl)-[1-(3-ethoxy-4-methoxy-benzyl)-piperidin-4-yl]-amine | Method B | 1-(3-ethoxy-4-methoxy-benzyl)-piperidin-4-ylamine (intermediate A1) and 4-azetidin-1-yl-2,6-dichloro-pyrimidine (intermediate B2) | 432.4 |
| 14 | 426.95 | (7-chloro-quinazolin-4-yl)-[1-(3-ethoxy-4-methoxy-benzyl)-piperidin-4-yl]-amine | Method A | 1-(3-ethoxy-4-methoxy-benzyl)-piperidin-4-ylamine (intermediate A1) and 4,7-dichloro-quinazoline (commercially available) | 427.3 |
| 15 | 479.38 | (2,7-dichloro-6-fluoro-quinazolin-4-yl)-[1-(3-ethoxy-4-methoxy-benzyl)-piperidin-4-yl]-amine | Method C | 1-(3-ethoxy-4-methoxy-benzyl)-piperidin-4-ylamine (intermediate A1) and 2,4,7-trichloro-6-fluoro-quinazoline (intermediate B3) | 479.4 |
| 16 | 487.00 | (2-chloro-6,7-dimethoxy-quinazolin-4-yl)-[1-(3-ethoxy-4-methoxy-benzyl)-piperidin-4-yl]-amine | Method D | 1-(3-ethoxy-4-methoxy-benzyl)-piperidin-4-ylamine (intermediate A1) and 2,4-dichloro-6,7-dimethoxy-quinazoline (commercially available) | 487.3 |

Example 17

[1-(4-Chloro-3-ethoxy-benzyl)-piperidin-4-yl]-(2-chloro-5-methyl-pyrimidin-4-yl)-amine

Step 1

[1-(4-Chloro-3-ethoxy-benzyl)-piperidin-4-yl]-carbamic acid tert-butyl ester

A mixture of piperidin-4-yl-carbamic acid tert-butyl ester (5.0 g, 25.0 mmol, 1.0 equiv), 4-chloro-3-ethoxy-benzaldehyde (5.54 g, 30.0 mmol, 1.2 equiv; intermediate D2, vide infra) and acetic acid (5.7 mL, 6.01 g, 100.0 mmol, 4.0 equiv) in ethanol (25 mL) was heated by microwave irradiation to 100° C. for 5 min. Sodium cyanoborohydride (3.14 g, 50.0 mmol, 2.0 equiv), dissolved in ethanol (10 mL), was added and the reaction mixture heated by microwave irradiation to 100° C. for an additional time period of 10 min. The solvent was removed under reduced pressure and the crude reaction product extracted from a solution of 1 M NaOH (100 mL) with ethyl acetate (3×100 mL). The combined organic phases were dried over MgSO$_4$, concentrated by evaporation under reduced pressure and the crude material purified by silica column chromatography using a MPLC system (CombiFlash Companion, Isco Inc.) eluting with a gradient of heptane/ethyl acetate providing 3.91 g (42%) of the title compound. MS (ISP): 369.0 [M+H]$^+$.

Step 2

1-(4-Chloro-3-ethoxy-benzyl)-piperidin-4-ylamine (Intermediate A2)

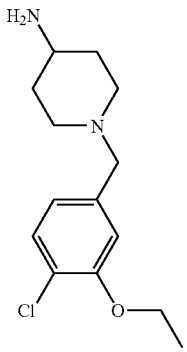

A solution of [1-(4-chloro-3-ethoxy-benzyl)-piperidin-4-yl]-carbamic acid tert-butyl ester (0.78 g, 2.12 mmol) in ethanol (10 mL) and 4 M HCl (15 mL) was stirred at rt for 2 h. The hydrochloric acid was removed under reduced pressure and the crude reaction product extracted from a solution of 1 M NaOH (50 mL) with ethyl acetate (3×50 mL). The combined organic phases were dried over MgSO$_4$ and concentrated by evaporation under reduced pressure yielding 0.32 g (57%) of a white solid. The crude material was directly used in the following reaction step. MS (ISP): 269.0 [M+H]$^+$.

Step 3 (Method B)

To a solution of 1-(4-chloro-3-ethoxy-benzyl)-piperidin-4-ylamine (40.3 mg, 0.15 mmol, 1.2 equiv; intermediate A2) in dry DMF (1.5 mL) was added sodium hydride (6.6 mg, 0.15 mmol, 1.2 equiv; 55% free-flowing powder moistened with oil) and the reaction mixture stirred at rt under Ar. After 2 h, 2,4-dichloro-5-methyl-pyrimidine (20.4 mg, 0.125 mmol, 1.0 equiv; commercially available) was added and the mixture heated to 120° C. for 48 h. Removal of the solvent under reduced pressure and purification by preparative HPLC on reversed phase eluting with a gradient of acetonitrile/water provided 3.7 mg (8%) of the title compound. MS (ISP): 395.2 [M+H]$^+$.

The pyrimidine intermediate B4 was prepared following literature precedents.

Synthesis of Pyrimidine Intermediate B4 to be Used in Table 2

Intermediate B4

2,4-Dichloro-5-(2-ethyl-4,5-dimethoxy-benzyl)-pyrimidine [CAS RN 6981-20-0]

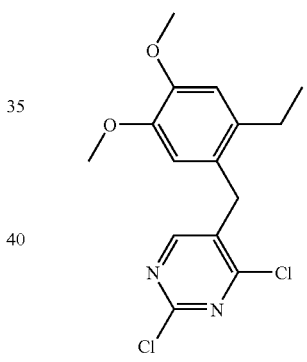

The title compound was prepared according to NL 6514 743 A (F. Hoffmann-La Roche A G).

Examples 18 to 24

According to the procedure described for the synthesis of example 1/step 3 (Method A) and example 2/step 2 (Method B) further pyrimidine, quinazoline and purine derivatives have been synthesized from 1-(4-chloro-3-ethoxy-benzyl)-piperidin-4-ylamine (intermediate A2) and the respective pyrimidine, quinazoline and purine intermediate as indicated in Table 2. The results are compiled in Table 2 and comprise example 18 to example 24.

TABLE 2

| No | MW | Compound Name | Preparation | Starting Materials | ISP [M + H]$^+$ found |
|---|---|---|---|---|---|
| 18 | 381.31 | [1-(4-chloro-3-ethoxy-benzyl)- | Method B | 1-(4-chloro-3-ethoxy-benzyl)-piperidin-4- | 381.3 |

TABLE 2-continued

| No | MW | Compound Name | Preparation | Starting Materials | ISP [M + H]+ found |
|----|------|---------------|-------------|--------------------|--------------------|
|    |      | piperidin-4-yl]-(2-chloro-pyrimidin-4-yl)-amine | | ylamine (intermediate A2) and 2,4-dichloro-pyrimidine (commercially available) | |
| 19 | 399.30 | [1-(4-chloro-3-ethoxy-benzyl)-piperidin-4-yl]-(2-chloro-5-fluoro-pyrimidin-4-yl)-amine | Method B | 1-(4-chloro-3-ethoxy-benzyl)-piperidin-4-ylamine (intermediate A2) and 2,4-dichloro-5-fluoro-pyrimidine (commercially available) | 399.2 |
| 20 | 396.32 | 6-chloro-N$^4$-[1-(4-chloro-3-ethoxy-benzyl)-piperidin-4-yl]-pyrimidine-4,5-diamine | Method B | 1-(4-chloro-3-ethoxy-benzyl)-piperidin-4-ylamine (intermediate A2) and 4,6-dichloro-pyrimidin-5-ylamine (commercially available) | 396.3 |
| 21 | 438.36 | N-{2-chloro-6-[1-(4-chloro-3-ethoxy-benzyl)-piperidin-4-ylamino]-pyrimidin-4-yl}-acetamide | Method B | 1-(4-chloro-3-ethoxy-benzyl)-piperidin-4-ylamine (intermediate A2) and N-(2,6-dichloro-pyrimidin-4-yl)-acetamide (intermediate B1) | 438.3 |
| 22 | 559.54 | [1-(4-chloro-3-ethoxy-benzyl)-piperidin-4-yl]-[2-chloro-5-(2-ethyl-4,5-dimethoxy-benzyl)-pyrimidin-4-yl]-amine | Method B | 1-(4-chloro-3-ethoxy-benzyl)-piperidin-4-ylamine (intermediate A2) and 2,4-dichloro-5-(2-ethyl-4,5-dimethoxy-benzyl)-pyrimidine (intermediate B4) | 559.3 |
| 23 | 431.37 | [1-(4-chloro-3-ethoxy-benzyl)-piperidin-4-yl]-(7-chloro-quinazolin-4-yl)-amine | Method A | 1-(4-chloro-3-ethoxy-benzyl)-piperidin-4-ylamine (intermediate A2) and 4,7-dichloro-quinazoline (commercially available) | 431.3 |
| 24 | 401.90 | N$^6$-[1-(4-chloro-3-ethoxy-benzyl)-piperidin-4-yl]-9H-purine-2,6-diamine | Method B | 1-(4-chloro-3-ethoxy-benzyl)-piperidin-4-ylamine (intermediate A2) and 6-chloro-9H-purin-2-ylamine (commercially available) | 402.4 |

Example 25

6-Chloro-N$^4$-[1-(3,5-diisopropoxy-benzyl)-piperidin-4-yl]-pyrimidine-4,5-diamine Step 1

[1-(3,5-Diisopropoxy-benzyl)-piperidin-4-yl]-carbamic acid tert-butyl ester

A mixture of piperidin-4-yl-carbamic acid tert-butyl ester (4.0 g, 20.0 mmol, 1.0 equiv), 3,5-diisopropoxy-benzaldehyde (5.33 g, 24.0 mmol, 1.2 equiv; intermediate D7, vide infra) and acetic acid (4.6 mL, 4.80 g, 80.0 mmol, 4.0 equiv) in ethanol (16 mL) was heated by microwave irradiation to 100° C. for 5 min. Sodium cyanoborohydride (2.51 g, 40.0 mmol, 2.0 equiv), dissolved in ethanol (8 mL), was added and the reaction mixture heated by microwave irradiation to 100° C. for an additional time period of 10 min. The solvent was removed under reduced pressure and the crude reaction product extracted from a solution of 1 M NaOH (100 mL) with ethyl acetate (3×100 mL). The combined organic phases were dried over MgSO$_4$, concentrated by evaporation under reduced pressure and the crude material purified on a Isolute flash NH2 chromatography column using a MPLC system (CombiFlash Companion, Isco Inc.) eluting with a gradient of heptane/ethyl acetate providing 3.23 g (40%) of the title compound. MS (ISP): 407.4 [M+H]+.

Step 2

1-(3,5-Diisopropoxy-benzyl)-piperidin-4-ylamine (Intermediate A3)

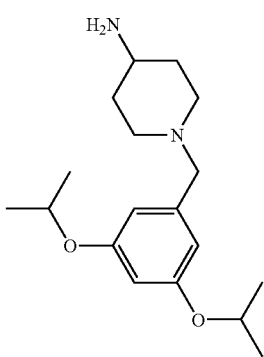

A solution of [1-(3,5-diisopropoxy-benzyl)-piperidin-4-yl]-carbamic acid tert-butyl ester (3.23 g, 7.95 mmol) in 4 M HCl (100 mL) was stirred at rt for 2 h. The hydrochloric acid was removed under reduced pressure and the crude reaction product extracted from a solution of 1 M NaOH (100 mL) with ethyl acetate (3×100 mL). The combined organic phases were dried over MgSO$_4$ and concentrated by evaporation under reduced pressure yielding 0.78 g (32%) of a colorless oil.

The crude material was directly used in the following reaction step. MS (ISP): 307.5 [M+H]$^+$.

Step 3 (Method H)

A solution of 4,6-dichloro-pyrimidin-5-ylamine (19.7 mg, 0.12 mmol, 1.0 equiv; commercially available) and 1-(3,5-diisopropoxy-benzyl)-piperidin-4-ylamine (46.0 mg, 0.15 mmol, 1.25 equiv; intermediate A3) in N-ethyl diisopropylamine (1.0 mL) and acetonitril (1.0 mL) was heated by microwave irradiation to 160° C. for 20 min. Removal of the solvent under reduced pressure and purification by preparative HPLC on reversed phase eluting with a gradient of acetonitrile/water provided 10.6 mg (20%) of the title compound. MS (ISP): 434.3 [M+H]$^+$.

Synthesis of Pyrimidine Intermediates B5 to B11 to be used in Table 3

Intermediate B5

4,6-Dichloro-5-phenoxy-pyrimidine [CAS RN 90876-79-2]

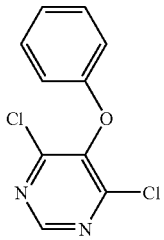

The title compound was prepared according to U.S. Pat. No. 5,292,740 (F. Hoffmann-La Roche A G).

Intermediate B6

4,6-Dichloro-5-o-tolyloxy-pyrimidine [CAS RN 150743-55-8]

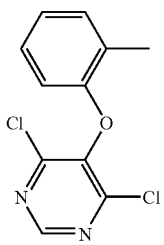

The title compound was prepared according to U.S. Pat. No. 5,292,740 (F. Hoffmann-La Roche A G).

Intermediate B7

4,6-Dichloro-5-(2-methoxy-phenoxy)-pyrimidine [CAS RN 150727-23-4]

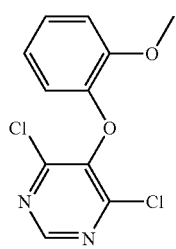

The title compound was prepared according to U.S. Pat. No. 5,292,740 (F. Hoffmann-La Roche A G).

Intermediate B8

4,6-Dichloro-5-(2-ethoxy-phenoxy)-pyrimidine [CAS RN 150727-94-9]

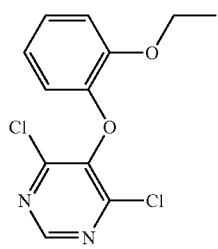

The title compound was prepared according to U.S. Pat. No. 5,292,740 (F. Hoffmann-La Roche A G).

Intermediate B9

4,6-Dichloro-5-(4-methoxy-phenoxy)-pyrimidine [CAS RN 150727-32-5]

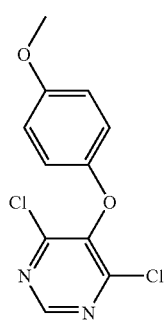

The title compound was prepared according to U.S. Pat. No. 5,292,740 (F. Hoffmann-La Roche A G).

Intermediate B10

4,6-Dichloro-5-(2-methoxy-benzyl)-pyrimidine [CAS RN 146532-80-1]

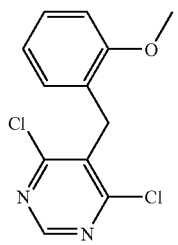

The title compound was prepared according to EP 510 526 B1 (F. Hoffmann-La Roche A G).

Intermediate B11

4,6-Dichloro-5-(2-trifluoromethyl-benzyl)-pyrimidine [CAS RN 146532-58-3]

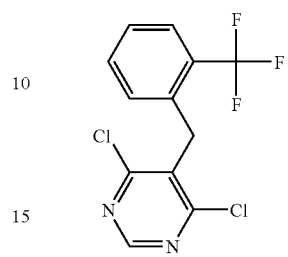

The title compound was prepared according to EP 510 526 B1 (F. Hoffmann-La Roche A G).

Examples 26 to 33

According to the procedure described for the synthesis of example 25/step 3 (Method H) further pyrimidine derivatives have been synthesized from 1-(3,5-diisopropoxy-benzyl)-piperidin-4-ylamine (intermediate A3) and the respective pyrimidine intermediate as indicated in Table 3. The results are compiled in Table 3 and comprise example 26 to example 33.

TABLE 3

| No | MW | Compound Name | Preparation | Starting Materials | ISP [M + H]+ found |
|---|---|---|---|---|---|
| 26 | 511.07 | (6-chloro-5-phenoxy-pyrimidin-4-yl)-[1-(3,5-diisopropoxy-benzyl)-piperidin-4-yl]-amine | Method H | 1-(3,5-diisopropoxy-benzyl)-piperidin-4-ylamine (intermediate A3) and 4,6-dichloro-5-phenoxy-pyrimidine (intermediate B5) | 511.4 |
| 27 | 525.09 | (6-chloro-5-o-tolyloxy-pyrimidin-4-yl)-[1-(3,5-diisopropoxy-benzyl)-piperidin-4-yl]-amine | Method H | 1-(3,5-diisopropoxy-benzyl)-piperidin-4-ylamine (intermediate A3) and 4,6-dichloro-5-o-tolyloxy-pyrimidine (intermediate B6) | 525.2 |
| 28 | 541.09 | [6-chloro-5-(2-methoxy-phenoxy)-pyrimidin-4-yl]-[1-(3,5-diisopropoxy-benzyl)-piperidin-4-yl]-amine | Method H | 1-(3,5-diisopropoxy-benzyl)-piperidin-4-ylamine (intermediate A3) and 4,6-dichloro-5-(2-methoxy-phenoxy)-pyrimidine_(intermediate B7) | 541.3 |
| 29 | 555.12 | [6-chloro-5-(2-ethoxy-phenoxy)-pyrimidin-4-yl]-[1-(3,5-diisopropoxy-benzyl)-piperidin-4-yl]-amine | Method H | 1-(3,5-diisopropoxy-benzyl)-piperidin-4-ylamine (intermediate A3) and 4,6-dichloro-5-(2-ethoxy-phenoxy)-pyrimidine_(intermediate B8) | 555.3 |
| 30 | 541.09 | [6-chloro-5-(4-methoxy-phenoxy)-pyrimidin-4-yl]-[1-(3,5-diisopropoxy-benzyl)-piperidin-4-yl]-amine | Method H | 1-(3,5-diisopropoxy-benzyl)-piperidin-4-ylamine (intermediate A3) and 4,6-dichloro-5-(4-methoxy-phenoxy)-pyrimidine (intermediate B9) | 541.3 |
| 31 | 539.12 | [6-chloro-5-(2-methoxy-benzyl)-pyrimidin-4-yl]-[1-(3,5-diisopropoxy-benzyl)-piperidin-4-yl]-amine | Method H | 1-(3,5-diisopropoxy-benzyl)-piperidin-4-ylamine (intermediate A3) and 4,6-dichloro-5-(2-methoxy-benzyl)-pyrimidine (intermediate B10) | 539.5 |

TABLE 3-continued

| No | MW | Compound Name | Preparation | Starting Materials | ISP [M + H]+ found |
|---|---|---|---|---|---|
| 32 | 577.09 | [6-chloro-5-(2-trifluoromethyl-benzyl)-pyrimidin-4-yl]-[1-(3,5-diisopropoxy-benzyl)-piperidin-4-yl]-amine | Method H | 1-(3,5-diisopropoxy-benzyl)-piperidin-4-ylamine (intermediate A3) and 4,6-dichloro-5-(2-trifluoromethyl-benzyl)-pyrimidine (intermediate B11) | 577.4 |
| 33 | 423.56 | [1-(3,5-diisopropoxy-benzyl)-piperidin-4-yl]-(7H-pyrrolo[2,3-d]pyrimidin-4-yl)-amine | Method H | 1-(3,5-diisopropoxy-benzyl)-piperidin-4-ylamine (intermediate A3) and 4-chloro-7H-pyrrolo[2,3-d]pyrimidine (commercially available) | 424.3 |

Example 34

(2-Chloro-pyrimidin-4-yl)-[1-(3-ethoxy-4-methyl-benzyl)-piperidin-4-yl]-amine

Step 1

4-(2-Chloro-pyrimidin-4-ylamino)-piperidine-1-carboxylic acid tert-butyl ester

A mixture of 2,4-dichloro-pyrimidine (4.0 g, 26.85 mmol, 1.0 equiv; commercially available) and 4-amino-piperidine-1-carboxylic acid tert-butyl ester (6.45 g, 32.22 mmol, 1.2 equiv) in anhydrous DMF (100 mL) was stirred at rt for 18 h. The organic phase was concentrated under reduced pressure and the crude reaction mixture purified with silica column chromatography using a MPLC system (CombiFlash Companion, Isco Inc.) eluting with a gradient of heptane/ethyl acetate providing 3.2 g (38%) of the title compound. $^1$H NMR (400 MHz, CDCl$_3$): δ 1.35-1.45 (m, 2H), 1.47 (s, 9H), 1.99-2.03 (m, 2H), 2.91-2.97 (m, 2H), 3.81-3.90 (m, 1H), 4.04-4.07 (br d, 2H), 5.33 (d, J=8.0 Hz, 1H), 6.25 (d, J=4.0 Hz, 1H), 7.98 (d, J=4.0 Hz, 1H). $^{13}$C NMR (75 MHz, DMSO): δ 28.05, 30.94, 42.04, 46.69, 78.64, 105.13, 153.86, 155.57, 159.81, 162.72. MS (ISP): 313.1 [M+H]+.

Step 2

(2-Chloro-pyrimidin-4-yl)-piperidin-4-yl-amine dihydrochloride (Intermediate C1)

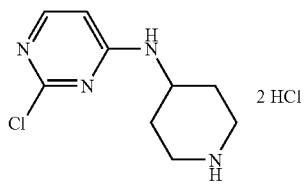

A solution of 4-(2-chloro-pyrimidin-4-ylamino)-piperidine-1-carboxylic acid tert-butyl ester (3.2 g, 10.23 mmol) in ethanol (40 mL) and 4 M HCl in dioxane (70 mL) was stirred at rt for 2 h. The solvent was removed under reduced pressure and the crude product used in the consecutive step without further purification assuming quantitative deprotection and formation of the dihydrochloride salt. MS (ISP): 213.3 [M+H]+.

Step 3

To a solution of (2-chloro-pyrimidin-4-yl)-piperidin-4-yl-amine dihydrochloride (42.9 mg, 0.15 mmol, 1.0 equiv; intermediate C1) in ethanol (2 mL), acetic acid (72.1 mg, 1.2 mmol, 8.0 equiv) and N-ethyl diisopropylamine (77.6 mg, 0.6 mmol, 4.0 equiv) was added 3-ethoxy-4-methyl-benzaldehyde (29.6 mg, 0.18 mmol, 1.2 equiv; intermediate D10, vide infra) and the mixture stirred at 55° C. After 1 h, sodium cyanoborohydride (47.1 mg, 0.75 mmol, 5.0 equiv), dissolved in ethanol (0.5 mL), was added and the mixture stirred at 55° C. over night. Removal of the solvent under reduced pressure and purification by preparative HPLC on reversed phase eluting with a gradient of acetonitrile/water provided 2.4 mg (4%) of the title compound. MS (ISP): 361.3 [M+H]+.

The pyrimidine, quinazoline and purine piperidine intermediates C2 to C14 were prepared following literature precedents or as described below.

Synthesis of Pyrimidine, Quinazoline and Purine Piperidine Intermediates C2 to C14 to be Used in Table 4

Intermediate C2

(2-Chloro-6-methyl-pyrimidin-4-yl)-piperidin-4-yl)-amine dihydrochloride

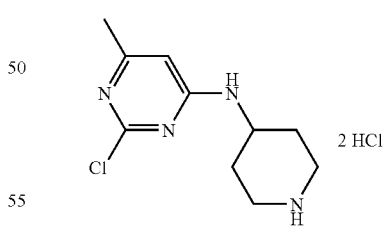

Step 1

4-(2-Chloro-6-methyl-pyrimidin-4-ylamino)-piperidine-1-carboxylic acid tert-butyl ester A solution of 2,4-dichloro-6-methyl-pyrimidine (1.25 g, 7.68 mmol, 1.0 equiv; commercially available), 4-amino-piperidine-1-carboxylic acid tert-butyl ester (2.0 g, 10.0 mmol, 1.3 equiv) and N-ethyl diisopropylamine (3.0 mL, 2.3 g, 17.7 mmol, 2.3 equiv) in acetonitrile (16 mL) was heated by microwave irradiation to 160° C. for 20 min. The reaction mixture was concentrated under reduced pressure and the crude material purified by silica column chromatography using a MPLC system (CombiFlash Companion, Isco Inc.) eluting with a gradient of heptane/ethyl acetate providing 1.15 g (46%) of the title compound. $^1$H NMR (400 MHz, DMSO): δ 1.24-1.31 (m, 2H), 1.40 (s, 9H), 1.80-1.83 (br d, 2H), 2.18 (s, 3H), 2.90 (br s, 2H), 3.87 (br s, 2H), 3.96 (br s, 1H), 6.23 (br s, 1H), 7.68 (d, J=8.0 Hz, 1H). MS (ISP): 327.4 [M+H]$^+$.

Step 2

A solution of 4-(2-chloro-6-methyl-pyrimidin-4-ylamino)-piperidine-1-carboxylic acid tert-butyl ester (1.15 g, 3.52 mmol) in 4 M HCl in dioxane (70 mL) was stirred at rt for 1 h. The solvent was removed under reduced pressure and the crude product used in the consecutive step without further purification assuming quantitative deprotection and formation of the dihydrochloride salt. MS (ISP): 225.3 [M+H]$^+$.

Intermediate C3

(2,6-Dichloro-pyrimidin-4-yl)-piperidin-4-yl-amine dihydrochloride

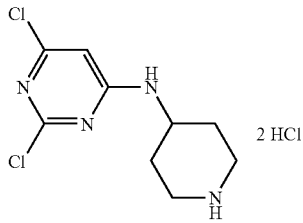

Step 1

4-(2,6-Dichloro-pyrimidin-4-ylamino)-piperidine-1-carboxylic acid tert-butyl ester To a solution of 4-amino-piperidine-1-carboxylic acid tert-butyl ester (4.0 g, 20.0 mmol, 1.3 equiv) in dry DMF (100 mL) under Ar was added sodium hydride (1.01 g, 23.1 mmol, 1.5 equiv; 55% free-flowing powder moistened with oil) and the reaction mixture stirred at rt. After 2 h, 2,4,6-trichloro-pyrimidine (2.82 g, 15.4 mmol, 1.0 equiv; commercially available) was added and the mixture stirred at rt for 48 h. The solvent was removed under reduced pressure and the crude reaction product extracted from a solution of 1 M NaOH (100 mL) with ethyl acetate (3×100 mL). The combined organic phases were dried over MgSO$_4$, concentrated by evaporation under reduced pressure and the crude material purified with silica column chromatography using a MPLC system (CombiFlash Companion, Isco Inc.) eluting with a gradient of heptane/ethyl acetate to provide 3.1 g (57%) of the title compound. $^1$H NMR (400 MHz, DMSO): δ 1.24-1.33 (m, 2H), 1.40 (s, 9H), 1.78-1.85 (m, 2H), 2.86-2.96 (m, 2H), 3.49-3.97 (m, 3H), 6.47 (s, 1H). MS (ISP): 347.3 [M+H]$^+$.

Step 2

A solution of 4-(2,6-dichloro-pyrimidin-4-ylamino)-piperidine-1-carboxylic acid tert-butyl ester (3.1 g, 8.93 mmol) in ethanol (40 mL) and 4 M HCl in dioxane (70 mL) was stirred at rt for 2 h. The solvent was removed under reduced pressure and the crude product used in the consecutive step without further purification assuming quantitative deprotection and formation of the dihydrochloride salt. MS (ISP): 247.3 [M+H]$^+$.

Intermediate C4

4-Methoxy-6-(piperidin-4-ylamino)-pyrimidin-2-ol dihydrochloride

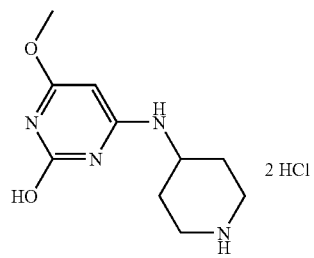

Step 1

4-(2,6-Dimethoxy-pyrimidin-4-ylamino)-piperidine-1-carboxylic acid tert-butyl ester A solution of 4-chloro-2,6-dimethoxy-pyrimidine (1.92 g, 11.0 mmol, 1.0 equiv; commercially available), 4-amino-piperidine-1-carboxylic acid tert-butyl ester (2.64 g, 13.20 mmol, 1.2 equiv) and N-ethyl diisopropylamine (2.24 mL, 1.71 g, 13.20 mmol, 1.2 equiv) in acetonitrile (8 mL) and DMAc (2 mL) was heated by microwave irradiation to 160° C. for 1 h and then to 180° C. for 30 min. The reaction mixture was concentrated under reduced pressure and the crude material purified by silica column chromatography using a MPLC system (CombiFlash Companion, Isco Inc.) eluting with a gradient of heptane/ethyl acetate providing 1.22 g (33%) of the title compound. $^1$H NMR (300 MHz, CDCl$_3$): δ1.39-1.48 (m, 2H), 1.46 (s, 9H), 1.97-2.00 (m, 2H), 2.85-2.96 (m, 2H), 3.86 (s, 3H), 3.89 (s, 3H), 3.96-4.02 (m, 3H), 5.52 (d, J=7.9 Hz, 1H). $^{13}$C NMR (75 MHz, CDCl$_3$): δ28.16, 31.48, 42.39, 47.95, 53.12, 53.76, 79.24, 100.51, 154.40, 164.60, 164.99, 171.52. MS (ISP): 339.4 [M+H]$^+$.

Step 2

A solution of 4-(2,6-dimethoxy-pyrimidin-4-ylamino)-piperidine-1-carboxylic acid tert-butyl ester (0.71 g, 2.10 mmol) in ethanol (10 mL) and 4 M HCl in dioxane (20 mL) was stirred at rt for 48 h. The solvent was removed under reduced pressure and the crude product used in the consecu-

Intermediate C5

2-Chloro-6-(piperidin-4-ylamino)-pyrimidine-4-carboxylic acid methyl ester dihydrochloride

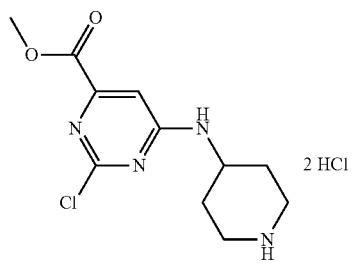

Step 1

6-(1-tert-Butoxycarbonyl-piperidin-4-ylamino)-2-chloro-pyrimidine-4-carboxylic acid methyl ester A mixture of 2,6-dichloro-pyrimidine-4-carboxylic acid methyl ester (3.98 g, 19.19 mmol, 1.0 equiv; commercially available) and 4-amino-piperidine-1-carboxylic acid tert-butyl ester (5.0 g, 24.94 mmol, 1.3 equiv) in anhydrous DMF (100 mL) was heated to 60° C. for 18 h. The organic phase was concentrated under reduced pressure and the crude reaction mixture extracted from a 1 M NaOH (100 mL) solution with ethyl acetate (3×50 mL). The combined organic phases were dried over MgSO$_4$ and the product purified with silica column chromatography using a MPLC system (CombiFlash Companion, Isco Inc.) eluting with a gradient of heptane/ethyl acetate providing 3.46 g (49%) of the title compound. $^1$H NMR (300 MHz, CDCl$_3$): δ1.42-1.51 (m, 2H), 1.47 (s, 9H), 2.00-2.05 (m, 2H), 2.90-3.01 (m, 2H), 3.92 (s, 3H), 4.05-4.10 (m, 2H), 4.19 (br s, 1H), 7.10 (s, 1H), 7.17 (br s, 1H). $^{13}$C NMR (75 MHz, CDCl$_3$): δ28.30, 31.23, 42.41, 48.00, 52.88, 79.61, 106.38, 153.58, 154.61, 161.21, 163.75, 164.23. MS (ISP): 371.1 [M+H]$^+$.

Step 2

A solution of 6-(1-tert-butoxycarbonyl-piperidin-4-ylamino)-2-chloro-pyrimidine-4-carboxylic acid methyl ester (3.46 g, 9.34 mmol) in ethanol (50 mL) and 4 M HCl in dioxane (75 mL) was stirred at rt for 2 h. The solvent was removed under reduced pressure and the crude product used in the consecutive step without further purification assuming quantitative deprotection and formation of the dihydrochloride salt. MS (ISP): 271.1 [M+H]$^+$.

Intermediate C6

N-[2-Chloro-6-(piperidin-4-ylamino)-pyrimidin-4-yl]-acetamide dihydrochloride

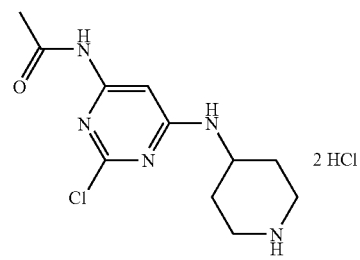

Step 1

4-(6-Acetylamino-2-chloro-pyrimidin-4-ylamino)-piperidine-1-carboxylic acid tert-butyl ester A mixture of N-(2,6-dichloro-pyrimidin-4-yl)-acetamide (0.7 g, 3.40 mmol, 1.0 equiv; intermediate B1) and 4-amino-piperidine-1-carboxylic acid tert-butyl ester (0.82 g, 4.08 mmol, 1.2 equiv) in anhydrous DMF (6 mL) was heated by microwave irradiation to 130° C. for 4 h. Removal of the solvent under reduced pressure and purification with column chromatography on silica eluting with a gradient of heptane/ethyl acetate (3:1→1:1) provided 0.1 g (8%) of the title compound. $^1$H NMR (300 MHz, CDCl$_3$): δ1.33-1.45 (m, 2H), 1.47 (s, 9H), 1.97-2.08 (m, 2H), 2.18 (s, 3H), 2.90-2.99 (m, 2H), 4.01-4.08 (m, 3H), 5.19 (br s, 1H), 7.13 (s, 1H), 8.04 (br s, 1H). MS (ISP): 370.1 [M+H]$^+$.

Step 2

A solution of 4-(6-acetylamino-2-chloro-pyrimidin-4-ylamino)-piperidine-1-carboxylic acid tert-butyl ester (0.1 g, 0.27 mmol) in ethanol (2 mL) and 4 M HCl in dioxane (2 mL) was stirred at rt for 2 h. The solvent was removed under reduced pressure and the crude product used in the consecutive step without further purification assuming quantitative deprotection and formation of the dihydrochloride salt. MS (ISP): 270.0 [M+H]$^+$.

Intermediate C7

(2-Chloro-5-fluoro-pyrimidin-4-yl)-piperidin-4-yl-amine dihydrochloride

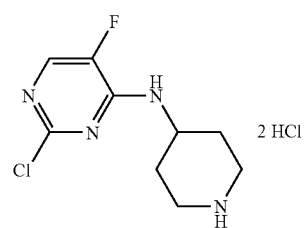

Step 1

4-(2-Chloro-5-fluoro-pyrimidin-4-ylamino)-piperidine-1-carboxylic acid tert-butyl ester A solution of 2,4-dichloro-5-fluoro-pyrimidine (1.28 g, 7.68 mmol, 1.0 equiv; commercially available), 4-amino-piperidine-1-carboxylic acid tert-butyl ester (2.0 g, 10.0 mmol, 1.3 equiv) and N-ethyl diisopropylamine (3.0 mL, 2.3 g, 17.7 mmol, 2.3 equiv) in acetonitrile (16 mL) was heated by microwave irradiation to 160° C. for 20 min. The reaction mixture was concentrated under reduced pressure and the crude material purified by silica column chromatography using a MPLC system (CombiFlash Companion, Isco Inc.) eluting with a gradient of heptane/ethyl acetate providing 2.23 g (88%) of the title compound. $^1$H NMR (400 MHz, DMSO): δ 1.38-1.48 (m, 2H), 1.41 (s, 9H), 1.78-1.82 (m, 2H), 2.84 (br s, 2H), 3.93-3.96 (m, 2H), 4.00-4.08 (m, 1H), 8.02 (d, J=6.0 Hz, 1H), 8.09 (d, J=4.0 Hz, 1H). $^{13}$C NMR (100 MHz, DMSO): δ 28.06, 30.75, 43.33, 47.34, 78.66, 139.86 (d, J=20.3 Hz), 145.03 (d, J=255.7 Hz), 152.63 (d, J=13.4 Hz), 153.49 (d, J=2.7 Hz), 153.83. MS (ISP): 331.3 [M+H]$^+$.

Step 2

A solution of 4-(2-chloro-5-fluoro-pyrimidin-4-ylamino)-piperidine-1-carboxylic acid tert-butyl ester (2.0 g, 6.05 mmol) in 4 M HCl in dioxane (100 mL) was stirred at rt for 1 h. The solvent was removed under reduced pressure and the crude product used in the consecutive step without further purification assuming quantitative deprotection and formation of the dihydrochloride salt. MS (ISP): 231.1 [M+H]$^+$.

Intermediate C8

(2-Chloro-5-methoxy-pyrimidin-4-yl)-piperidin-4-yl-amine dihydrochloride

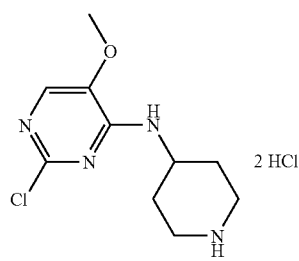

Step 1

4-(2-Chloro-5-methoxy-pyrimidin-4-ylamino)-piperidine-1-carboxylic acid tert-butyl ester A solution of 2,4-dichloro-5-methoxy-pyrimidine (0.80 g, 4.47 mmol, 1.0 equiv; commercially available from Specs Research Laboratory, The Netherlands), 4-amino-piperidine-1-carboxylic acid tert-butyl ester (1.34 g, 6.70 mmol, 1.5 equiv) and triethylamine (0.93 mL, 0.68 g, 6.70 mmol, 1.5 equiv) in acetonitrile (9 mL) and DMAc (2 mL) was heated by microwave irradiation to 120° C. for 20 min. The reaction mixture was concentrated under reduced pressure and the crude material purified by silica column chromatography using a MPLC system (CombiFlash Companion, Isco Inc.) eluting with a gradient of heptane/ethyl acetate providing 1.43 g (93%) of the title compound. $^1$H NMR (400 MHz, CDCl$_3$): δ1.28-1.49 (m, 2H), 1.40 (s, 9H), 1.93-1.98 (m, 2H), 2.85-2.92 (m, 2H), 3.80 (s, 3H), 3.97-4.02 (m, 2H), 4.06-4.12 (m, 1H), 5.22 (d, J=8.0 Hz, 1H), 7.46 (s, 1H). MS (ISP): 343.3 [M+H]$^+$.

Step 2

A solution of 4-(2-chloro-5-methoxy-pyrimidin-4-ylamino)-piperidine-1-carboxylic acid tert-butyl ester (1.43 g, 4.17 mmol) in dichloromethane (10 mL) and 4 M HCl in dioxane (40 mL) was stirred at rt for 2 h. The solvent was removed under reduced pressure and the crude product used in the consecutive step without further purification assuming quantitative deprotection and formation of the dihydrochloride salt. MS (ISP): 243.3 [M+H]$^+$.

Intermediate C9

(2-Chloro-6,7-dihydro-5H-cyclopentapyrimidin-4-yl)-piperidin-4-yl-amine dihydrochloride

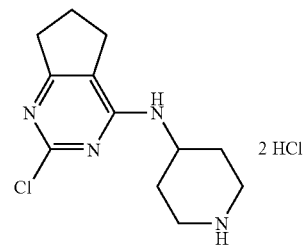

Step 1

2,4-Dichloro-6,7-dihydro-5H-cyclopentapyrimidine [CAS RN 5466-43-3]

The title compound was prepared as described in Y.-Z. Kim, J.-C. Lim, J.-H. Yeo, C.-S. Bang, W.-S. Kim, S.-S. Kim, Y.-M. Woo, D.-H. Yang, H. Oh and K. Nahm *J. Med. Chem.* 1994, 37, 3828-3833.

Step 2

4-(2-Chloro-6,7-dihydro-5H-cyclopentapyrimidin-4-ylamino)-piperidine-1-carboxylic acid tert-butyl ester A mixture of 2,4-dichloro-6,7-dihydro-5H-cyclopentapyrimidine (2.71 g, 14.34 mmol, 1.0 equiv) and 4-amino-piperidine-1-carboxylic acid tert-butyl ester (3.45 g, 17.20 mmol, 1.2 equiv) in anhydrous DMF (40 mL) was heated to 60° C. for 18 h. The organic phase was concentrated under reduced pressure and the crude reaction mixture extracted from a solution of 1 M NaOH (100 mL) with ethyl acetate (3×50 mL). The combined organic phases were dried over MgSO$_4$ and the product purified with column chromatography on silica eluting with a gradient of heptane/ethyl acetate (14:3→1:1) providing 2.34 g (47%) of the title compound. $^1$H NMR (300 MHz, DMSO): δ 1.32-1.43 (m, 2H), 1.39 (s, 9H), 1.79-1.82 (m, 2H), 2.0 (quint, J=7.5 Hz, 2H), 2.61 (t, J=7.5 Hz, 2H), 2.70 (t, J=7.5 Hz, 2H), 2.80-2.88 (m, 2H), 3.93-3.98

(m, 2H), 4.04-4.13 (m, 1H), 7.07 (d, J=8.0 Hz, 1H). $^{13}$C NMR (75 MHz, DMSO): δ 21.12, 26.42, 28.04, 31.17, 33.19, 42.55, 47.12, 78.53, 114.87, 153.84, 157.95, 159.02, 172.18. MS (ISP): 353.1 [M+H]$^+$.

Step 3

A solution of 4-(2-chloro-6,7-dihydro-5H-cyclopentapyrimidin-4-ylamino)-piperidine-1-carboxylic acid tert-butyl ester (2.34 g, 6.63 mmol) in MeOH (10 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 253.1 [M+H]$^+$.

Intermediate C10

[2,4-Dichloro-6-(piperidin-4-ylamino)-pyrimidin-5-yl]-acetic acid ethyl ester dihydrochloride

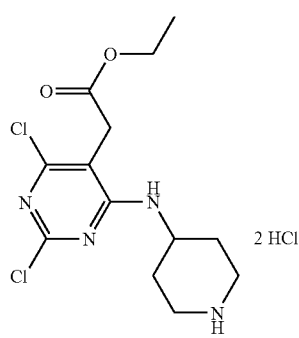

Step 1

4-(2,6-Dichloro-5-ethoxycarbonylmethyl-pyrimidin-4-ylamino)-piperidine-1-carboxylic acid tert-butyl ester A solution of (2,4,6-trichloro-pyrimidin-5-yl)-acetic acid ethyl ester (1.00 g, 3.71 mmol, 1.0 equiv; commercially available from Tyger Scientific Inc, USA), 4-amino-piperidine-1-carboxylic acid tert-butyl ester (1.26 g, 6.31 mmol, 1.7 equiv) and triethylamine (0.77 mL, 0.56 g, 5.57 mmol, 1.5 equiv) in acetonitrile (9 mL) and DMAc (2 mL) was heated by microwave irradiation to 120° C. for 30 min. The reaction mixture was concentrated under reduced pressure and the crude material purified by silica column chromatography using a MPLC system (CombiFlash Companion, Isco Inc.) eluting with a gradient of heptane/ethyl acetate providing 0.87 g (54%) of the title compound. $^1$H NMR (400 MHz, DMSO): δ 1.19 (t, J=8.0 Hz, 3H), 1.35-1.44 (m, 2H), 1.40 (s, 9H), 1.76-1.79 (m, 2H), 2.84 (br s, 2H), 3.73 (s, 2H), 3.93-3.96 (m, 2H), 4.11 (q, J=8.0 Hz, 2H), 4.08-4.13 (m, 1H), 7.52 (d, J=8.0 Hz, 1H). MS (ISP): 433.3 [M+H]$^+$.

Step 2

A solution of 4-(2,6-dichloro-5-ethoxycarbonylmethyl-pyrimidin-4-ylamino)-piperidine-1-carboxylic acid tert-butyl ester (0.87 g, 2.01 mmol) in dichloromethane (10 mL) and 4 M HCl in dioxane (40 mL) was stirred at rt for 2 h. The solvent was removed under reduced pressure and the crude product used in the consecutive step without further purification assuming quantitative deprotection and formation of the dihydrochloride salt. MS (ISP): 333.1 [M+H]$^+$.

Intermediate C11

Piperidin-4-yl-(2,5,6-trichloro-pyrimidin-4-yl)-amine dihydrochloride

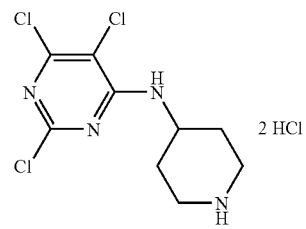

Step 1

4-(2,5,6-Trichloro-pyrimidin-4-ylamino)-piperidine-1-carboxylic acid tert-butyl ester A solution of 2,4,5,6-tetrachloro-pyrimidine (1.67 g, 7.68 mmol, 1.0 equiv; commercially available), 4-amino-piperidine-1-carboxylic acid tert-butyl ester (2.0 g, 10.0 mmol, 1.3 equiv) and N-ethyl diisopropylamine (3.0 mL, 2.3 g, 17.7 mmol, 2.3 equiv) in acetonitrile (16 mL) was heated by microwave irradiation to 160° C. for 20 min. The reaction mixture was concentrated under reduced pressure and the crude material purified by silica column chromatography using a MPLC system (CombiFlash Companion, Isco Inc.) eluting with a gradient of heptane/ethyl acetate providing 0.85 g (29%) of the title compound. $^1$H NMR (400 MHz, DMSO): δ 1.41 (s, 9H), 1.49-1.60 (m, 2H), 1.73-1.77 (m, 2H), 2.81 (br s, 2H), 3.95-3.98 (m, 2H), 4.09-4.16 (m, 1H), 7.88 (d, J=8.0 Hz, 1H). $^{13}$C NMR (100 MHz, DMSO): δ 28.07, 30.45, 43.33, 48.90, 78.65, 109.37, 153.80, 154.62, 155.66, 158.74. MS (ISP): 383.0 [M+H]$^+$.

Step 2

A solution of 4-(2,5,6-trichloro-pyrimidin-4-ylamino)-piperidine-1-carboxylic acid tert-butyl ester (0.85 g, 2.23 mmol) in 4 M HCl in dioxane (100 mL) was stirred at rt for 2 h. The solvent was removed under reduced pressure and the crude product used in the consecutive step without further purification assuming quantitative deprotection and formation of the dihydrochloride salt. MS (ISP): 283.4 [M+H]+.

Intermediate C12

(7-Chloro-quinazolin-4-yl)-piperidin-4-yl-amine dihydrochloride

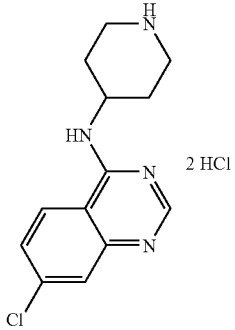

Step 1

4-(7-Chloro-quinazolin-4-ylamino)-piperidine-1-carboxylic acid tert-butyl ester

To a solution of 4-amino-piperidine-1-carboxylic acid tert-butyl ester (3.62 g, 18.1 mmol, 1.2 equiv) in dry DMF (20 mL) under Ar was added sodium hydride (0.99 g, 22.7 mmol, 1.5 equiv; 55% free-flowing powder moistened with oil) and the reaction mixture stirred at rt. After 2 h, 4,7-dichloro-quinazoline (3.0 g, 15.1 mmol, 1.0 equiv; commercially available) was added and the mixture heated by microwave irradiation to 140° C. for 30 min. Removal of the solvent under reduced pressure and purification with column chromatography on silica eluting with a gradient of heptane/ethyl acetate (10:1→1:1) afforded 4-(7-chloro-quinazolin-4-ylamino)-piperidine-1-carboxylic acid tert-butyl ester (4.33 g, 79%). $^1$H NMR (300 MHz, CDCl$_3$): δ1.42-1.53 (m, 2H), 1.48 (s, 9H), 2.16-2.18 (m, 2H), 2.92-2.98 (m, 2H), 4.17-4.20 (m, 2H), 4.39-4.49 (m, 1H), 5.79 (d, J=8.0 Hz, 1H), 7.40 (dd, J=8.8 Hz, J=2.1 Hz, 1H), 7.71 (d, J=8.8 Hz, 1H), 7.82 (d, J=2.1 Hz, 1H), 8.63 (s, 1H). $^{13}$C NMR (75 MHz, CDCl$_3$): δ28.50, 32.05, 42.89, 48.38, 79.85, 113.29, 122.11, 126.75, 127.89, 138.70, 150.65, 154.78, 156.37, 158.58. MS (ISP): 363.5 [M+H]+.

Step 2

A solution of 4-(7-chloro-quinazolin-4-ylamino)-piperidine-1-carboxylic acid tert-butyl ester (4.33 g, 11.9 mmol) in dioxane (35 mL) and conc. HCl (10 mL) was stirred at rt for 18 h. The solvent was removed under reduced pressure and the crude product used in the consecutive step without further purification assuming quantitative deprotection and formation of the dihydrochloride salt. MS (ESP): 263.0 [M+H]+.

Intermediate C13

(2-Chloro-6,7-dimethoxy-quinazolin-4-yl)-piperidin-4-yl-amine dihydrochloride

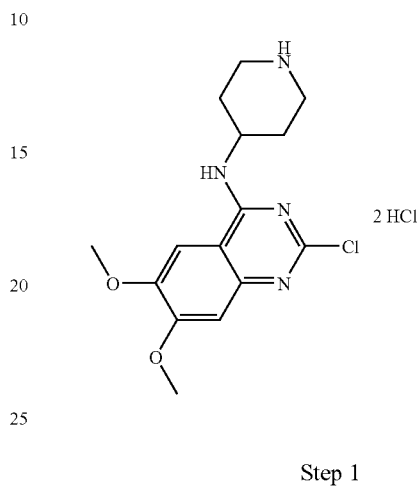

Step 1

4-(2-Chloro-6,7-dimethoxy-quinazolin-4-ylamino)-piperidine-1-carboxylic acid tert-butyl ester To a solution of 2,4-dichloro-6,7-dimethoxyquinazoline (5.12 g, 19.8 mmol, 1.0 equiv) in THF (50 mL) was added 4-amino-piperidine-1-carboxylic acid tert-butyl ester (4.34 g, 21.7 mmol, 1.1 equiv) and 1,8-diazabicyclo[5.4.0]undec-7-ene (3.31 g, 3.25 mL, 21.7 mmol, 1.1 equiv) and the reaction mixture stirred at rt for 16 h. Additional 4-amino-piperidine-1-carboxylic acid tert-butyl ester (0.87 g, 4.3 mmol, 0.2 equiv) and 1,8-diazabicyclo[5.4.0]undec-7-ene (0.66 g, 0.65 mL, 4.3 mmol, 0.2 equiv) were added and the mixture was stirred for 2 h. The solvent was evaporated under reduced pressure and the mixture dissolved in dichloromethane (100 mL). The solution was washed with water (2×20 mL) and a sat. solution of NaCl (20 mL), the aqueous layers were combined and extracted with dichloromethane (20 mL). The combined organic layers were dried over MgSO$_4$ and evaporated under reduced pressure to give an amber solid. The solid was crystallized from MeOH (500 mL) to afford 4-(2-chloro-6,7-dimethoxy-quinazolin-4-ylamino)-piperidine-1-carboxylic acid tert-butyl ester (2.67 g, 22%) as a white solid. The mother liquors were evaporated and purified with column chromatography on silica eluting with a gradient of heptane/ethyl acetate (1:1)→ethyl acetate and the fractions combined to afford additional 4-(2-chloro-6,7-dimethoxy-quinazolin-4-ylamino)-piperidine-1-carboxylic acid tert-butyl ester (1.0 g, 12%). $^1$H NMR (250 MHz, CDCl$_3$): δ1.49-1.51 (m, 2H), 1.61 (s, 9H), 2.30-2.48 (m, 2H), 2.89-3.10 (m, 2H), 4.04 (s, 3H), 4.09 (s, 3H), 4.29-4.48 (m, 2H), 4.75-4.50 (m, 1H), 5.61 (d, J=8.0 Hz, 1H), 6.87 (s, 1H), 7.18 (s, 1H). MS (ESP): 423.5 [M+H]+.

Step 2

A solution of 4-(2-chloro-6,7-dimethoxy-quinazolin-4-ylamino)-piperidine-1-carboxylic acid tert-butyl ester (3.65 g, 8.6 mmol) in dioxane (35 mL) and conc. HCl (5 mL) was stirred at rt for 18 h. The solvent was removed under reduced pressure and the crude product used in the consecutive step without further purification assuming quantitative deprotection and formation of the dihydrochloride salt. MS (ESP): 323.3 [M+H]⁺.

Intermediate C14

Piperidin-4-yl-(9H-purin-6-yl)-amine dihydrochloride

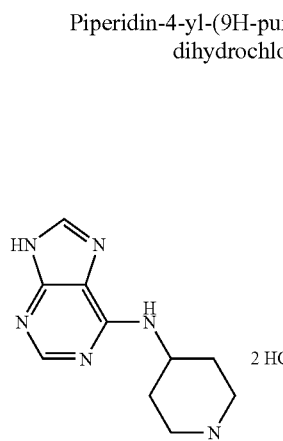

Step 1

4-(9H-Purin-6-ylamino)-piperidine-1-carboxylic acid tert-butyl ester

A solution of 6-chloro-9H-purine (1.19 g, 7.68 mmol, 1.0 equiv; commercially available), 4-amino-piperidine-1-carboxylic acid tert-butyl ester (2.0 g, 10.0 mmol, 1.3 equiv) and N-ethyl diisopropylamine (3.0 mL, 2.3 g, 17.7 mmol, 2.3 equiv) in acetonitrile (16 mL) was heated by microwave irradiation to 160° C. for 20 min. The reaction mixture was concentrated under reduced pressure and the crude material purified by silica column chromatography using a MPLC system (CombiFlash Companion, Isco Inc.) eluting with a gradient of heptane/ethyl acetate. Suspension of the pre-purified material in ethyl acetate and filtration provided 0.89 g (36%) of the title compound. ¹H NMR (300 MHz, DMSO): δ 1.31-1.43 (m, 2H), 1.40 (s, 9H), 1.87-1.90 (m, 2H), 2.74-2.88 (m, 2H), 3.92-3.96 (m, 2H), 4.32 (br s, 1H), 7.52 (br s, 1H), 8.08 (s, 1H), 8.18 (s, 1H). MS (ISP): 319.3 [M+H]⁺.

Step 2

A solution of 4-(9H-purin-6-ylamino)-piperidine-1-carboxylic acid tert-butyl ester (0.89 g, 2.8 mmol) in 4 M HCl in dioxane (50 mL) was stirred at rt for 1 h. The solvent was removed under reduced pressure and the crude product used in the consecutive step without further purification assuming quantitative deprotection and formation of the dihydrochloride salt. MS (ISP): 219.4 [M+H]⁺.

The aldehyde intermediates D1 to D33 were prepared following literature precedents or in analogy to literature precedents or as described below.

Synthesis of Aldehyde Intermediates D1 to D25 to be Used in Table 4

Intermediate D1

3-Ethoxy-4-fluoro-benzaldehyde

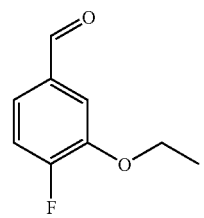

The title compound was prepared according to the procedure described for the synthesis of 4-chloro-3-ethoxy-benzaldehyde (intermediate D2, vide infra) starting from 4-fluoro-3-hydroxy-benzoic acid in 73% overall yield after purification by flash column chromatography on silica eluting with hexane/ethyl acetate (10:1). ¹H NMR (300 MHz, DMSO): δ 1.32 (t, J=7.0 Hz, 3H), 4.12 (q, J=7.0 Hz, 2H), 7.34-7.41 (m, 1H), 7.47-7.56 (m, 2H), 9.87 (s, 1H). MS (ISP): 186.1 [M+NH₄]⁺.

Intermediate D2

4-Chloro-3-ethoxy-benzaldehyde [CAS RN 85259-46-7]

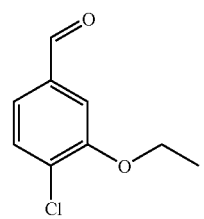

To a solution of 4-chloro-3-hydroxy-benzoic acid (3.0 g, 17.4 mmol, 1.0 equiv) in DMF (15 mL) was added K₂CO₃ (4.81 g, 34.8 mmol, 2.0 equiv) and ethyl iodide (4.03 mL, 5.97 g, 38.2 mmol, 2.2 equiv). The reaction mixture was stirred for 6 h at rt, diluted with water (20 mL) and extracted with ethyl acetate (3×50 mL). The organic phases were dried over Na₂SO₄ and concentrated to afford 3.6 g (91%) of 4-chloro-3-ethoxy-benzoic acid ethyl ester. The crude ester was then dissolved in THF (20 mL) and cooled to −78° C. under Ar. A solution of diisobutylaluminium hydride (95 mL, 95.0 mmol, 6.0 equiv; 1.0 M solution in THF) was slowly added over a time period of 15 min, the cooling bath removed on completion of addition and the reaction allowed to warm up to 0° C. After stirring for 1 h, the reaction was cooled to −78° C. and the excess hydride quenched by cautious addition of a solution of 1 M HCl (10 mL). The mixture was brought to rt, the organic phase separated and the aqueous layer extracted with ethyl acetate (3×100 mL). The combined organic phases were dried over Na$_2$SO$_4$ and concentrated by evaporation under reduced pressure providing 2.94 g (100%) of 4-chloro-3-ethoxy-benzyl alcohol. The crude alcohol (2.94 g, 15.75 mmol, 1.0 equiv) was dissolved in dichloromethane (15 mL) and activated MnO$_2$ (5.48 g, 63.0 mmol, 4.0 equiv) was added. The reaction mixture was stirred for 16 h, after which time the reaction was filtered through Hyflo Super Cel and concentrated. The residue was purified by flash column chromatography on silica eluting with heptane/ethyl acetate (4:1) to yield 1.51 g (52%) of the title compound. $^1$H NMR (300 MHz, CDCl$_3$): δ1.51 (t, J=7.1 Hz, 3H), 4.19 (q, J=7.1 Hz, 2H), 7.37-7.42 (m, 2H), 7.55 (d, J=9.0 Hz, 1H), 9.94 (s, 1H).

Intermediate D3

3-Ethoxy-4-(1-ethyl-propoxy)-benzaldehyde

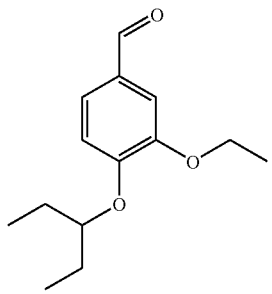

The title compound was prepared analogously to 3-ethoxy-4-methyl-benzaldehyde (intermediate D10, vide infra) by reaction of 3-ethoxy-4-hydroxy-benzaldehyde with 3-bromo-pentane in DMF using K$_2$CO$_3$ as base. MS (ISP): 237.1 [M+H]$^+$.

Intermediate D4

3-Butoxy-4-methoxy-benzaldehyde

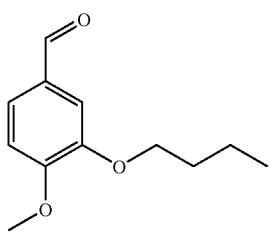

The title compound was prepared analogously to 3-ethoxy-4-methyl-benzaldehyde (intermediate D10, vide infra) by reaction of 3-hydroxy-4-methoxy-benzaldehyde with 4-bromo-butane in DMF using K$_2$CO$_3$ as base. MS (ISP): 209.1 [M+H]$^+$.

Intermediate D5

3,5-Diethoxy-benzaldehyde [CAS RN 120355-79-5]

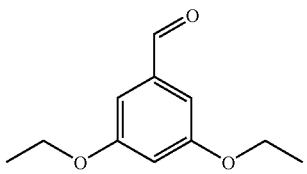

The title compound was prepared analogously to 3-ethoxy-4-methyl-benzaldehyde (intermediate D10, vide infra) by reaction of 3,5-dihydroxybenzaldehyde with ethyl iodide in DMF using K$_2$CO$_3$ as base.

Intermediate D6

3-Hydroxy-5-isopropoxy-benzaldehyde

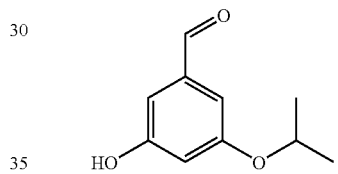

Isolated as a side-product in the synthesis of 3,5-diisopropoxy-benzaldehyde (intermediate D7, vide infra). $^1$H NMR (300 MHz, CDCl$_3$): δ1.34 (d, J=6.1 Hz, 6H), 4.58 (hept, J=6.1 Hz, 1H), 6.28 (br s, 1H), 6.68-6.69 (m, 1H), 6.95-6.98 (m, 2H), 9.85 (s, 1H). MS (ISN): 179.1 [M–H]$^-$.

Intermediate D7

3,5-Diisopropoxy-benzaldehyde [CAS RN 94169-64-9]

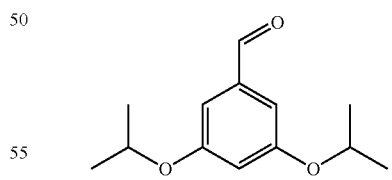

To a solution of 3,5-dihydroxy-benzaldehyde (5.0 g, 36.20 mmol, 1.0 equiv) in anhydrous DMF (30 mL) was added K$_2$CO$_3$ (15.0 g, 108.60 mmol, 3.0 equiv) and 2-bromo-propane (13.36 g, 10.20 mL, 108.60 mmol, 3.0 equiv) and the mixture stirred at 100° C. for 18 h. The K$_2$CO$_3$ was removed by filtration and the organic phase concentrated under reduced pressure. To the residue was added a sat. solution of NaCl (100 mL) and the solution extracted with ethyl acetate (3×100 mL). The combined organic phases were dried over MgSO$_4$ and the product purified by silica column chromatography using a MPLC system (CombiFlash Companion, Isco Inc.) eluting with a gradient of heptane/ethyl acetate affording 6.64 g (83%) of the title compound and 0.59 g (9%) of 3-hydroxy-5-isopropoxy-benzaldehyde (intermediate D6). $^1$H NMR (300 MHz, CDCl$_3$): δ1.35 (d, J=6.1 Hz, 6H), 4.59 (hept, J=6.1 Hz, 1H), 6.66-6.68 (m, 1H), 6.96-6.97 (m, 2H), 9.88 (s, 1H). MS (ISP): 223.1 [M+H]$^+$.

Intermediate D8

3-Ethoxy-4-iodo-5-methoxymethoxy-benzaldehyde [CAS RN 338451-02-8]

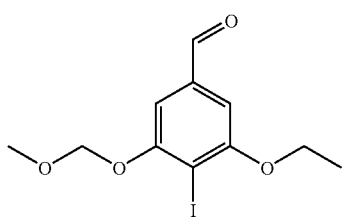

The title compound was prepared as described in WO 01/032 633 A1 (F. Hoffmann-La Roche A G).

Intermediate D9

2-Chloro-3,5-diethoxy-benzaldehyde

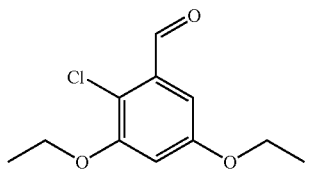

The title compound was prepared analogously to 3-ethoxy-4-methyl-benzaldehyde (intermediate D10, vide infra) by reaction of 2-chloro-3,5-dihydroxy benzaldehyde with iodoethane in DMF using K$_2$CO$_3$ as base. MS (ISP): 229.3 [M+H]$^+$.

Intermediate D10

3-Ethoxy-4-methyl-benzaldehyde [CAS RN 157143-20-9]

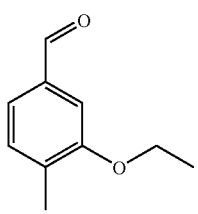

The title compound was prepared by reaction of commercially available 3-hydroxy-4-methyl-benzaldehyde with ethyl iodide in DMF using K$_2$CO$_3$ as base in analogy to the procedure described in M. J. Ashton, D. C. Cook, G. Fenton, J.-A. Karlsson, M. N. Palfreyman, D. Raeburn, A. J. Ratcliffe, J. E. Souness, S. Thurairatnam and N. Vicker *J. Med. Chem.* 1994, 37, 1696-1703.

Intermediate D11

4-Methoxy-3-propoxy-benzaldehyde [CAS RN 5922-56-5]

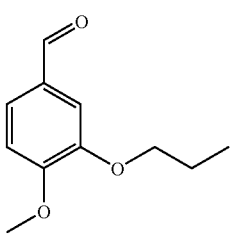

The title compound was prepared by reaction of isovanillin with propyl iodide in DMF using K$_2$CO$_3$ as base in analogy to the preparation of 3-ethoxy-4-methyl-benzaldehyde (intermediate D10).

Intermediate D12

3-(2-Fluoro-ethoxy)-4-methoxy-benzaldehyde

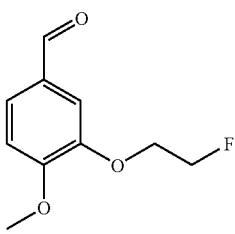

To a solution of 3-hydroxy-4-methoxy-benzaldehyde (10.0 g, 66.0 mmol, 1.0 equiv) in anhydrous DMF (40 mL) was added K$_2$CO$_3$ (13.6 g, 99.0 mmol, 1.5 equiv) and 1-bromo-2-fluoro-ethane (9.2 mg, 72.0 mmol, 1.1 equiv) and the mixture stirred at rt for 48 h. The K$_2$CO$_3$ was removed by filtration and the organic phase concentrated under reduced pressure. To the residue was added a sat. solution of NaCl (100 mL) and the solution extracted with ethyl acetate (3×100 mL). The combined organic phases were dried over MgSO$_4$ and the product crystallized from a mixture of isopropanol/diethylether to yield 12.69 g (97%) of the title compound. $^1$H NMR (300 MHz, DMSO): δ 3.89 (s, 3H), 4.24-4.27 (m, 1H), 4.34-4.37 (m, 1H), 4.67-4.70 (m, 1H), 4.83-4.86 (m, 1H), 7.20 (d, J=8.4 Hz, 1H), 7.43 (d, J=1.9 Hz, 1H), 7.59 (dd, J=8.4 Hz, J=1.9 Hz, 1H), 9.84 (s, 1H). MS (ISP): 198.6 [M+H]⁺.

Intermediate D13

4-Methoxy-3-(2,2,2-trifluoro-ethoxy)-benzaldehyde [CAS RN 76588-84-6]

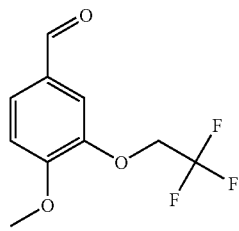

The title compound was prepared according to EP 0 251 294 B1 (Shionogi & Co.).

Intermediate D14

3-Allyloxy-4-methoxy-benzaldehyde [CAS RN 225939-36-6]

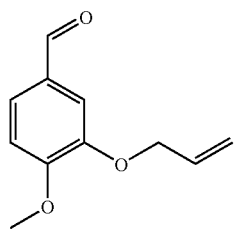

The title compound was prepared analogously to 3-ethoxy-4-methyl-benzaldehyde (intermediate D10) by reaction of 3-hydroxy-4-methoxy-benzaldehyde with allylbromide in DMF using $K_2CO_3$ as base (see also A. W. White, R. Almassy, A. H. Calvert, N. J. Curtin, R. J. Griffin, Z. Hostomsky, K. Maegley, D. R. Newell, S. Srinivasan and B. T. Golding *J. Med. Chem.* 2000, 43, 4084-4097).

Intermediate D15

3-Isobutoxy-4-methoxy-benzaldehyde [CAS RN 57724-26-2]

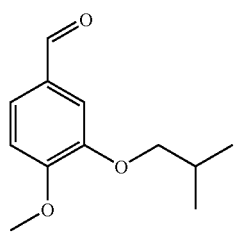

The title compound was prepared by reaction of isovanillin with 1-bromo-2-methyl propane as described in WO 04/000 806 A1 (Elbion A G).

Intermediate D16

8-Ethoxy-2,2-dimethyl-2H-chromene-6-carbaldehyde [CAS RN 210404-30-9]

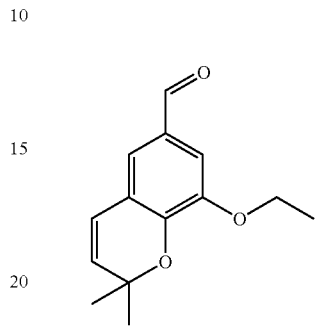

The title compound was prepared according to WO 01/083 476 A1 (Hoffmann-La Roche A G).

Intermediate D17

4-Chloro-3,5-diethoxy-benzaldehyde

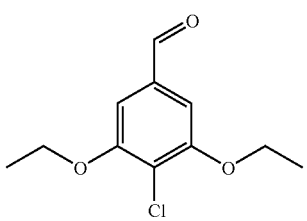

Step 1

4-Chloro-3,5-diethoxy-benzoic acid ethyl ester

To a solution of 4-amino-3,5-diethoxy-benzoic acid ethyl ester (5.1 g, 20.13 mmol, 1.0 equiv; prepared as described in I. Kompis and A. Wick, *Helv. Chim. Acta* 1977, 60, 3025-3034) in water (40 mL) and 37% HCl (40 mL) at 0° C. was added sodium nitrite (1.67 g, 24.16 mmol, 1.2 equiv). After 10 min, copper(I) chloride (12.0 g, 120.81 mmol, 6.0 equiv) was added, the reaction mixture stirred for an additional 5 h at 0° C. and then the ice bath removed. After stirring for 18 h, the crude reaction mixture was adjusted to pH=8 by addition of a solution of 1 M NaOH and the aqueous layer extracted with ethyl acetate (3×100 mL). The combined organic phases were dried over $MgSO_4$, concentrated by evaporation under reduced pressure and the crude material purified by silica column chromatography using a MPLC system (CombiFlash Companion, Isco Inc.) eluting with a gradient of heptane/ethyl acetate providing 5.0 g (91%) of the title compound. ¹H NMR (300 MHz, $CDCl_3$): δ1.32 (t, J=7.0 Hz, 4H), 1.40 (t, J=7.0 Hz, 6H), 4.09 (q, J=7.0 Hz, 4H), 4.30 (q, J=7.0 Hz, 2H), 7.18 (s, 2H). ¹³C NMR (75 MHz, $CDCl_3$): δ13.33, 13.66, 60.29, 64.16, 105.75, 115.88, 128.25, 154.49, 165.01. MS (ISP): 273.3 [M+H]⁺.

Step 2

(4-Chloro-3,5-diethoxy-phenyl)-methanol

To a solution of 4-chloro-3,5-diethoxy-benzoic acid ethyl ester (5.0 g, 18.33 mmol, 1.0 equiv) in dichloromethane (25 mL) was added slowly over a time period of 15 min under slight cooling to −30° C. a solution of diisobutylaluminium hydride (55.0 mL, 55.00 mmol, 3.0 equiv; 1.0 M solution in THF). After 30 min, the excess hydride was quenched by cautious addition of methanol (10 mL) and water (2 mL). The mixture was stirred for 30 min, a solution of 1 M HCl was added and the aqueous layer extracted with ethyl acetate (3×100 mL). The combined organic phases were dried over MgSO$_4$ and concentrated by evaporation under reduced pressure providing 4.0 g (95%) of the title compound. $^1$H NMR (300 MHz, CDCl$_3$): δ 1.45 (t, J=7.0 Hz, 6H), 1.93 (br s, 1H), 4.09 (q, J=7.0 Hz, 4H), 4.62 (s, 2H), 6.57 (s, 2H). $^{13}$C NMR (75 MHz, CDCl$_3$): δ 14.74, 64.96, 65.18, 104.30, 110.65, 140.29, 155.66. MS (ISP): 231.4 [M+H]$^+$.

Step 3

To a solution of (4-chloro-3,5-diethoxy-phenyl)-methanol (4.0 g, 17.34 mmol, 1.0 equiv) in THF (40 mL) was added activated MnO$_2$ (15.08 g, 173.4 mmol, 10.0 equiv) and the reaction mixture stirred for 18 h at rt. Filtration through Hyflo Super Cel and purification of the crude material by silica column chromatography using a MPLC system (CombiFlash Companion, Isco Inc.) eluting with a gradient of heptane/ ethyl acetate provided 3.7 g (92%) of the title compound. $^1$H NMR (300 MHz, CDCl$_3$): δ 1.50 (t, J=7.0 Hz, 6H), 4.19 (q, J=7.0 Hz, 4H), 7.07 (s, 2H), 9.89 (s, 1H). $^{13}$C NMR (75 MHz, CDCl$_3$): δ 14.61, 65.22, 106.26, 118.64, 135.08, 156.22, 191.01. MS (EI): 229.4 [M]$^+$.

Intermediate D18

4-Bromo-3,5-diethoxy-benzaldehyde [CAS RN 363166-11-4]

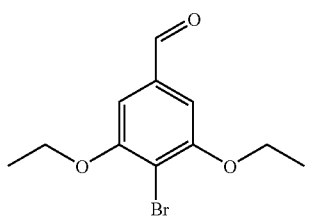

The title compound was prepared from 4-bromo-3,5-dihydroxy-benzoic acid as described in S. P. Dudek, H. D. Sikes and C. E. D. Chidsey *J. Am. Chem. Soc.* 2001, 123, 8033-8038.

Intermediate D19

3,5-Diethoxy-4-pyrrol-1-yl-benzaldehyde

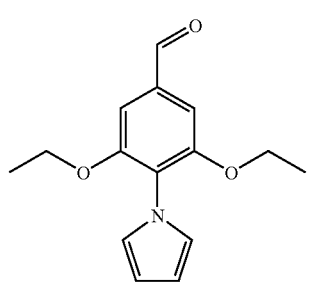

Step 1

3,5-Diethoxy-4-pyrrol-1-yl-benzoic acid ethyl ester

To a solution of 4-amino-3,5-diethoxy-benzoic acid ethyl ester (3.0 g, 11.84 mmol, 1.0 equiv; prepared as described in I. Kompis and A. Wick *Helv. Chim. Acta* 1977, 60, 3025-3034) in heptane (10 mL) and conc. acetic acid (0.2 mL) was added 2,5-dimethoxy-tetrahydro-furan (1.88 g, 14.21 mmol, 1.2 equiv). After heating to reflux for 5 h, a Dean-Stark apparatus was attached and the reaction mixture heated for an additional time period of 5 h. Filtration of the crude reaction mixture and crystallization at 0° C. from heptane provided 2.94 g (82%) of the title compound. $^1$H NMR (300 MHz, DMSO): δ 1.15 (t, J=7.0 Hz, 6H), 1.27 (t, J=7.1 Hz, 3H), 3.98 (q, J=7.0 Hz, 4H), 4.28 (q, J=7.1 Hz, 2H), 6.07-6.08 (m, 2H), 6.73-6.74 (m, 2H), 7.22 (s, 2H). $^{13}$C NMR (75 MHz, DMSO): δ 14.11, 14.35, 61.06, 64.57, 106.87, 107.64, 122.61, 123.33, 129.29, 153.75, 165.06. MS (ISP): 303.4 [M+H]$^+$.

Step 2

To a solution of 3,5-diethoxy-4-pyrrol-1-yl-benzoic acid ethyl ester (1.51 g, 4.98 mmol, 1.0 equiv) in toluene (5 mL) was added slowly over a time period of 15 min under slight cooling to 20° C. a solution of diisobutylaluminium hydride (8.9 mL, 12.45 mmol, 2.5 equiv; 20% solution in toluene). After 1 h, the excess hydride was quenched by cautious addition of water (10 mL) and a 28% solution of NaOH (2 mL). The mixture was stirred for 30 min and the organic phase filtered over Hyflo Super Cel. The aqueous layer was extracted with toluene (2×50 mL), the combined organic phases washed with a sat. solution of NaCl (2×50 mL) and concentrated by evaporation under reduced pressure to afford 1.30 g (100%) of (3,5-diethoxy-4-pyrrol-1-yl-phenyl)-methanol. The crude alcohol (1.30 g, 4.98 mmol, 1.0 equiv) was dissolved in toluene (20 mL) and activated MnO$_2$ (7.79 g, 89.5 mmol, 18.0 equiv) was added. The reaction mixture was heated to reflux for 7 h, after which time the reaction mixture was filtered through Hyflo Super Cel and concentrated yielding 1.15 g (89% yield) of the title compound. $^1$H NMR (300 MHz, DMSO): δ 1.17 (t, J=7.0 Hz, 6H), 4.02 (q, J=7.0 Hz, 4H), 6.08-6.09 (m, 2H), 6.75-6.76 (m, 2H), 7.25 (s, 2H), 9.89 (s, 1H). MS (ISP): 260.1 [M+H]+.

Intermediate D20

3,5-Diethoxy-4-fluoro-benzaldehyde

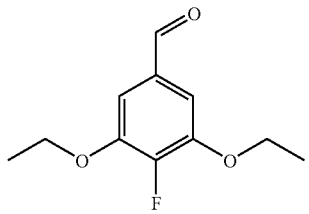

Step 1 tert-Butyl-(4-fluoro-benzyloxy)-dimethyl-silane

To a solution of (4-fluoro-phenyl)-methanol (12.16 g, 96.4 mmol, 1.0 equiv) in anhydrous DMF (50 mL) at 0° C. under Ar was added imidazole (7.22 g, 106.1 mmol, 1.1 equiv) and tert-butyl-chloro-dimethyl-silane (15.99 g, 106.1 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of Na$_2$CO$_3$ (2×100 mL) and NaCl (2×100 mL). The organic phase was dried over Na$_2$SO$_4$, concentrated by evaporation under reduced pressure yielding a brown oil that was purified by high vacuum distillation (bp 32-35° C. at 0.1 mbar) to give 23.0 g (99%) of the title compound. $^1$H NMR (400 MHz, CDCl$_3$): δ0.00 (s, 6H), 0.84 (s, 9H), 4.60 (s, 2H), 6.89-6.94 (m, 2H), 7.16-7.20 (m, 2H). MS (EI): 183.1 [M-tert-Bu]+.

Step 2

5-(tert-Butyl-dimethyl-silanyloxymethyl)-2-fluoro-phenol

To a solution of tert-butyl-(4-fluoro-benzyloxy)-dimethyl-silane (5.00 g, 20.8 mmol, 1.0 equiv) in anhydrous THF (20 mL) was added at −78° C. under Ar a solution of sec-BuLi (17.6 mL, 22.8 mmol, 1.1 equiv; 1.3 M solution in hexane) within 30 min. Then a solution of trimethyl borate (2.37 mL, 2.20 g, 20.8 mmol, 1.0 equiv) in anhydrous THF (7.5 mL) was added slowly within 30 min and the cooling bath removed. A solution of conc. acetic acid (2.78 mL, 1.87 g, 31.2 mmol, 1.5 equiv) was slowly added followed by addition of a solution of 35% hydrogen peroxide in water (2.0 mL, 2.23 g, 22.9 mmol, 1.1 equiv) and the reaction mixture kept at 0° C. for 30 min. After stirring at rt for an additional 4 h, the reaction was extracted with diethyl ether (2×100 mL) and the combined organic phases washed with a solution of 10% NaOH (2×100 mL) and a sat. solution of NaCl (2×100 mL). The organic phase was dried over Na$_2$SO$_4$, concentrated by evaporation under reduced pressure and the crude material purified with column chromatography on silica eluting with hexane/ethyl acetate (19:1) providing 4.80 g (90%) of the title compound. $^1$H NMR (400 MHz, CDCl$_3$): δ0.00 (s, 6H), 0.84 (s, 9H), 4.56 (s, 2H), 4.97 (br s, 1H), 6.68-6.72 (m, 1H), 6.87-6.94 (m, 2H). MS (EI): 256.2 [M]+.

Step 3

2-(tert-Butyl-dimethyl-silanyloxy)-4-(tert-butyl-dimethyl-silanyloxymethyl)-1-fluoro-benzene To a solution of 5-(tert-butyl-dimethyl-silanyloxymethyl)-2-fluoro-phenol (4.60 g, 17.9 mmol, 1.0 equiv) in anhydrous DMF (20 mL) at 0° C. under Ar was added imidazole (1.34 g, 19.7 mmol, 1.1 equiv) and tert-butyl-chloro-dimethyl-silane (2.97 g, 19.7 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of Na$_2$CO$_3$ (2×100 mL) and NaCl (2×100 mL). The organic phase was dried over Na$_2$SO$_4$ and concentrated by evaporation under reduced pressure yielding 4.50 g (68%) of the title compound. $^1$H NMR (400 MHz, CDCl$_3$): δ0.00 (s, 6H), 0.10 (s, 6H), 0.85 (s, 9H), 0.92 (s, 9H), 4.55 (s, 2H), 6.71-6.74 (m, 1H), 6.80-6.83 (m, 1H), 6.87-6.92 (m, 1H). MS (O): 370.2 [M]+.

Step 4

3-(tert-Butyl-dimethyl-silanyloxy)-5-(tert-butyl-dimethyl-silanyloxymethyl)-2-fluoro-phenol To a solution of 2-(tert-butyl-dimethyl-silanyloxy)-4-(tert-butyl-dimethyl-silanyloxymethyl)-1-fluoro-benzene (23.70 g, 63.9 mmol, 1.0 equiv) in anhydrous THF (130 mL) was added at −78° C. under Ar a solution of sec-BuLi (54.5 mL, 71.6 mmol, 1.1 equiv; 1.3 M solution in hexane) within 30 min. Then a solution of trimethyl borate (7.13 mL, 6.64 g, 63.9 mmol, 1.0 equiv) in anhydrous THF (30 mL) was added slowly within 30 min and the cooling bath removed. A solution of conc. acetic acid (5.49 mL, 5.76 g, 95.9 mmol, 1.5 equiv) was slowly added followed by addition of a solution of 35% hydrogen peroxide in water (6.2 mL, 6.83 g, 70.3 mmol, 1.1 equiv) and the reaction mixture kept at 0° C. for 30 min. After stirring at rt for an additional 4 h, the reaction was extracted with diethyl ether (2×100 mL) and the combined organic phases washed with a solution of 10% NaOH (2×100 mL) and a sat. solution of NaCl (2×100 mL). The organic phase was dried over Na$_2$SO$_4$, concentrated by evaporation under reduced pressure and the crude material purified with column chromatography on silica eluting with hexane/ethyl acetate (19:1) providing 15.80 g (64%) of the title compound. $^1$H NMR (400 MHz, CDCl$_3$): δ0.00 (s, 6H), 0.10 (s, 6H), 0.85 (s, 9H), 0.91 (s, 9H), 4.50 (s, 2H), 4.93 (br s, 1H), 6.37 (d, J=5.6 Hz, 1H), 6.47 (d, J=5.6 Hz, 1H). MS (EI): 329.2 [M-tert-Bu]+.

Step 5 tert-Butyl-(3,5-diethoxy-4-fluoro-benzyloxy)-dimethyl-silane

To a solution of 3-(tert-butyl-dimethyl-silanyloxy)-5-(tert-butyl-dimethyl-silanyloxymethyl)-2-fluoro-phenol (5.80 g, 15.0 mmol, 1.0 equiv) in DMF (60 mL) was added K$_2$CO$_3$ (4.56 g, 33.0 mmol, 2.2 equiv) and ethyl bromide (2.46 mL, 3.60 g, 33.0 mmol, 2.2 equiv) and the reaction mixture stirred under Ar at 60° C. for 5 h. The K$_2$CO$_3$ was removed by filtration, the crude reaction mixture concentrated by evaporation under reduced pressure, the residue extracted with ethyl acetate (3×100 mL), the combined organic phases washed with water (2×100 ml) and dried over Na$_2$SO$_4$. The solvent was removed by evaporation under reduced pressure and the crude material purified with column chromatography on silica eluting with hexane/ethyl:acetate (99:1) providing 3.10 g (63%) of the title compound. $^1$H NMR (400 MHz, CDCl$_3$): δ0.00 (s, 6H), 0.85 (s, 9H), 1.33 (t, J=7.0 Hz, 6H), 4.00 (q, J=7.0 Hz, 4H), 4.55 (s, 2H), 6.47 (d, J=6.8 Hz, 2H). MS (ISP): 329.3 [M+H]$^+$.

Step 6

(3,5-Diethoxy-4-fluoro-phenyl)-methanol

To a solution of tert-butyl-(3,5-diethoxy-4-fluoro-benzyloxy)-dimethyl-silane (1.20 g, 3.65 mmol, 1.0 equiv) in methanol (8 mL) was added Dowex 50W-X8 (0.33 g, cation exchange resin) and the reaction mixture stirred under Ar at rt for 22 h. The resin was removed by filtration and the reaction mixture concentrated by evaporation under reduced pressure yielding the title compound in quantitative yield (0.78 g). $^1$H NMR (400 MHz, CDCl$_3$): δ1.34 (t, J=7.0 Hz, 6H), 1.57 (t, J=5.4 Hz, 1H), 4.01 (q, J=7.0 Hz, 4H), 4.51 (d, J=5.4 Hz, 2H), 6.51 (d, J=6.8 Hz, 2H). MS (EI): 214.2 [M]$^+$.

Step 7

To a solution of (3,5-diethoxy-4-fluoro-phenyl)-methanol (2.30 g, 10.7 mmol, 1.0 equiv) in 1,2-dichloroethane (50 mL) was added activated MnO$_2$ (2.89 g, 33.3 mmol, 3.1 equiv). The reaction mixture was stirred for 21 h at 50° C. and then filtered through Hyflo Super Cel providing after evaporation of the solvent under reduced pressure 1.90 g (83%) of the title compound. $^1$H NMR (400 MHz, CDCl$_3$): δ1.38 (t, J=7.0 Hz, 6H), 4.09 (q, J=7.0 Hz, 4H), 7.04 (d, J=7.2 Hz, 2H), 9.75 (s, 1H). MS (EI): 212.1 [M]$^+$.

Intermediate D21

3-Ethoxy-4-methoxy-5-nitro benzaldehyde

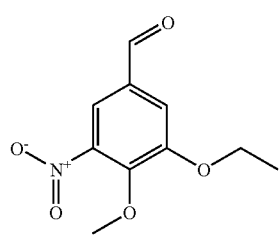

To a solution of 3-ethoxy-4-methoxybenzaldehyde (6.0 g, 33.3 mmol, 1.0 equiv; commercially available) in diethyl ether (50 mL) was added dropwise nitric acid 65% (4.12 mL, 5.81 g, 59.9 mmol, 1.8 equiv) over a period of 30 min at rt. After the addition was completed the reaction mixture was heated to reflux for 4 h. The reaction product precipitated out of solution, was filtered off, washed with cold diethyl ether (3×20 mL) and dried yielding 5.85 g (78%) of the title compound. $^1$H NMR (300 MHz, CDCl$_3$): δ1.53 (t, J=7.0 Hz, 3H), 4.04 (s, 3H), 4.26 (q, J=7.0 Hz, 2H), 7.37 (s, 1H), 7.61 (s, 1H), 10.40 (s, 1H). $^{13}$C NMR (75 MHz, CDCl$_3$): δ14.34, 56.68, 65.35, 107.31, 110.48, 125.52, 143.56, 152.54, 152.70, 187.60. MS (ISP): 225.9 [M+H]$^+$.

Intermediate D22

3-Ethylamino-4-methoxy-benzaldehyde

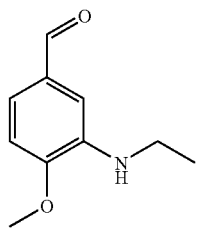

Through a solution of 2-(3-bromo-4-methoxy-phenyl)-[1,3]dioxolane (1.2 g, 4.63 mmol, 1.0 equiv; prepared as described in WO 01/74775 A1, Sanofi-Synthelabo) in toluene (6 mL) was bubbled ethylamine for 10 min. To this solution was added KOtert-Bu (0.67 g, 6.95 mmol, 1.5 equiv), rac-2,2'-bis(diphenylphosphino)-1,1'-binaphthalene (0.029 g, 0.046 mmol, 0.01 equiv) and tris(dibenzylideneacetone)-dipalladium(0) (0.021 g, 0.023 mmol, 0.005 equiv) and the solution heated to 110° C. under microwave irradiation for 20 min. A few drops of a solution of 37% HCl were added and the reaction mixture heated again under microwave irradiation to 100° C. for 5 min. Evaporation of the solvent and purification of the crude reaction product by column chromatography on silica eluting with hexane/ethyl acetate (7:3) provided 0.52 g (63%) of the title compound. $^1$H NMR (300 MHz, CDCl$_3$): δ1.24 (t, J=7.1 Hz, 3H), 3.16 (q, J=7.1 Hz, 2H), 3.86 (s, 3H), 4.17 (br s, 1H), 6.78 (d, J=8.1 Hz, 1H), 7.01 (d, J=1.9 Hz, 1H), 7.13 (dd, J=8.1 Hz, J=1.9 Hz, 1H), 9.75 (s, 1H). MS (ISP): 179.9 [M+H]$^+$.

Intermediate D23

4-Amino-3,5-diethoxy-benzaldehyde

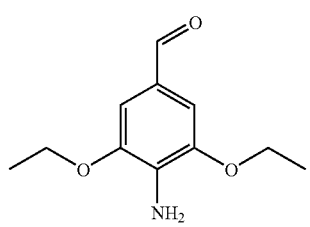

Step 1

(4-Amino-3,5-diethoxy-phenyl)-methanol

To a solution of 4-amino-3,5-diethoxy-benzoic acid ethyl ester (2.8 g, 11.05 mmol, 1.0 equiv; prepared as described in I. Kompis, A. Wick Helv. Chim. Acta 1977, 60, 3025-3034) in dichloromethane (50 mL) at 0° C. under Ar was slowly added diisobutylaluminium hydride (27.6 mL, 27.64 mmol, 2.5 equiv; 1.0 M solution in dichloromethane) over a time period of 15 min and the cooling bath removed on completion of addition. After stirring for 18 h, the excess hydride was quenched by cautious addition of a sat. solution of potassium sodium tartrate (10 mL). The solidified mixture was extracted with dichloromethane (5×200 mL) and THF (2×150 mL), the combined organic phases washed with water (3×100 mL), dried over MgSO$_4$, concentrated by evaporation under reduced pressure and the crude material purified by column chromatography on silica eluting with a gradient of heptane/ethyl acetate (4:1→1:1) providing 1.10 g (47%) of the title compound. $^1$H NMR (300 MHz, CDCl$_3$): δ1.42 (t, J=7.0 Hz, 3H), 3.82 (br s, 2H), 4.05 (q, J=7.0 Hz, 2H), 4.54 (s, 2H), 6.50 (s, 2H). $^{13}$C NMR (75 MHz, CDCl$_3$): δ15.03, 64.21, 66.00, 104.51, 125.44, 129.89, 146.71. MS (ISP): 211.9 [M+H]$^+$.

Step 2

To a solution of (4-amino-3,5-diethoxy-phenyl)-methanol (0.79 g, 3.74 mmol, 1.0 equiv) in DMF (20 mL) was added activated MnO$_2$ (1.63 g, 18.70 mmol, 5.0 equiv). The reaction mixture was stirred for 24 h at rt, filtered through Hyflo Super Cel, the filtrate extracted with ethyl acetate (3×50 mL) and the combined organic phases dried over MgSO$_4$ providing 0.69 g (88%) of the title compound. $^1$H NMR (300 MHz, DMSO): δ 1.46 (t, J=7.0 Hz, 3H), 4.15 (q, J=7.0 Hz, 2H), 4.50 (br s, 2H), 7.04 (s, 2H), 9.70 (s, 1H). MS (ISP): 210.0 [M+H]$^+$.

Intermediate D24

Methanesulfonic acid 2-ethoxy-4-formyl-phenyl ester

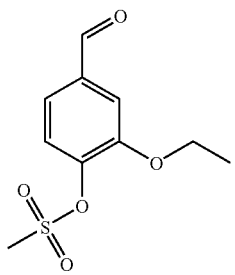

To a solution of 3-ethoxy-4-hydroxybenzaldehyde (3.0 g, 18.1 mmol, 1.0 equiv) and N,N-dimethylaminopyridine (2.87 g, 23.5 mmol, 1.3 equiv) in dichloromethane (10 mL) under Ar at 0° C. was added methanesulfonyl chloride (1.68 mL, 2.48 g, 21.7 mmol, 1.2 equiv). After the reaction mixture was stirred for 1 h, water (100 mL) was added, the solution extracted with dichloromethane (3×50 mL) and the combined organic phases dried over MgSO$_4$. Removal of the solvent by evaporation under reduced pressure provided the title compound in quantitative yield (4.8 g). $^1$H NMR (300 MHz, CDCl$_3$): δ1.42 (t, J=7.0 Hz, 3H), 3.19 (s, 3H), 4.14 (q, J=7.0 Hz, 2H), 7.41 (s, 2H), 7.45 (s, 1H), 9.89 (s, 1H). $^{13}$C NMR (75 MHz, CDCl$_3$): δ14.53, 38.94, 64.99, 112.20, 124.38, 125.17, 136.01, 142.92, 151.63, 190.65. MS (ISP): 245.2 [M+H]$^+$.

Intermediate D25

3-Benzyloxy-5-ethoxy-benzaldehyde [CAS RN 227023-81-6]

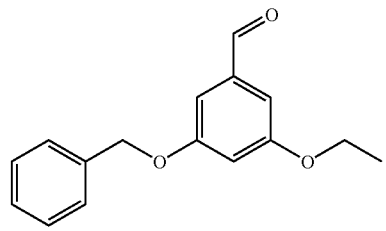

The title compound was prepared according to EP 0921 116 A1 (F. Hoffmann-La Roche A G).

Examples 35 to 216

According to the procedure described for the synthesis of example 34/step 3 further pyrimidine, quinazoline and purine derivatives have been synthesized from (2-chloro-pyrimidin-4-yl)-piperidin-4-yl-amine dihydrochloride (intermediate C1), (2-chloro-6-methyl-pyrimidin-4-yl)-piperidin-4-yl-amine dihydrochloride (intermediate C2), (2,6-dichloro-pyrimidin-4-yl)-piperidin-4-yl-amine dihydrochloride (intermediate C3), 4-methoxy-6-(piperidin-4-ylamino)-pyrimidin-2-ol dihydrochloride (intermediate C4), 2-chloro-6-(piperidin-4-ylamino)-pyrimidine-4-carboxylic acid methyl ester dihydrochloride (intermediate C5), N-[2-chloro-6-(piperidin-4-ylamino)-pyrimidin-4-yl]-acetamide dihydrochloride (intermediate C6), (2-chloro-5-fluoro-pyrimidin-4-yl)-piperidin-4-yl-amine dihydrochloride (intermediate C7), (2-chloro-5-methoxy-pyrimidin-4-yl)-piperidin-4-yl-amine dihydrochloride (intermediate C8), (2-chloro-6,7-dihydro-5H-cyclopentapyrimidin-4-yl)-piperidin-4-yl-amine dihydrochloride (intermediate C9), [2,4-dichloro-6-(piperidin-4-ylamino)-pyrimidin-5-yl]-acetic acid ethyl ester dihydrochloride (intermediate C10), piperidin-4-yl-(2,5,6-trichloro-pyrimidin-4-yl)-amine dihydrochloride (intermediate C11), (7-chloro-quinazolin-4-yl)-piperidin-4-yl-amine dihydrochloride (intermediate C12), (2-chloro-6,7-dimethoxy-quinazolin-4-yl)-piperidin-4-yl-amine dihydrochloride (intermediate C13) and piperidin-4-yl-(9H-purin-6-yl)-amine dihydrochloride (intermediate C14) and the respective benzaldehyde intermediate as indicated in Table 4. The results are compiled in Table 4 and comprise example 35 to example 216.

TABLE 4

| No | MW | Compound Name | Starting Materials | [M + H]$^+$ or [M − H]$^-$ found |
|---|---|---|---|---|
| 35 | 364.85 | (2-chloro-pyrimidin-4-yl)-[1-(3-ethoxy-4-fluoro-benzyl)-piperidin-4-yl]-amine | (2-chloro-pyrimidin-4-yl)-piperidin-4-yl-amine dihydrochloride (intermediate C1) and 3-ethoxy-4-fluoro-benzaldehyde (intermediate D1) | ISP [M + H]$^+$ 365.2 |

TABLE 4-continued

| No | MW | Compound Name | Starting Materials | [M + H]+ or [M − H]− found |
|---|---|---|---|---|
| 36 | 381.31 | [1-(4-chloro-3-ethoxy-benzyl)-piperidin-4-yl]-(2-chloro-pyrimidin-4-yl)-amine | (2-chloro-pyrimidin-4-yl)-piperidin-4-yl-amine dihydrochloride (intermediate C1) and 4-chloro-3-ethoxy-benzaldehyde (intermediate D2) | ISP [M + H]+ 381.3 |
| 37 | 362.86 | 4-[4-(2-chloro-pyrimidin-4-ylamino)-piperidin-1-ylmethyl]-2-ethoxy-phenol | (2-chloro-pyrimidin-4-yl)-piperidin-4-yl-amine dihydrochloride (intermediate C1) and 3-ethoxy-4-hydroxy-benzaldehyde (commercially available) | ISP [M + H]+ 363.5 |
| 38 | 404.94 | (2-chloro-pyrimidin-4-yl)-[1-(3-ethoxy-4-isopropoxy-benzyl)-piperidin-4-yl]-amine | (2-chloro-pyrimidin-4-yl)-piperidin-4-yl-amine dihydrochloride (intermediate C1) and 3-ethoxy-4-isopropoxy-benzaldehyde (commercially available) | ISP [M + H]+ 405.4 |
| 39 | 433.00 | (2-chloro-pyrimidin-4-yl)-{1-[3-ethoxy-4-(1-ethyl-propoxy)-benzyl]-piperidin-4-yl}-amine | (2-chloro-pyrimidin-4-yl)-piperidin-4-yl-amine dihydrochloride (intermediate C1) and 3-ethoxy-4-(1-ethyl-propoxy)-benzaldehyde (intermediate D3) | ISP [M + H]+ 433.4 |
| 40 | 404.94 | [1-(3-butoxy-4-methoxy-benzyl)-piperidin-4-yl]-(2-chloro-pyrimidin-4-yl)-amine | (2-chloro-pyrimidin-4-yl)-piperidin-4-yl-amine dihydrochloride (intermediate C1) and 3-butoxy-4-methoxy-benzaldehyde (intermediate D4) | ISP [M + H]+ 405.4 |
| 41 | 390.91 | (2-chloro-pyrimidin-4-yl)-[1-(3,5-diethoxy-benzyl)-piperidin-4-yl]-amine | (2-chloro-pyrimidin-4-yl)-piperidin-4-yl-amine dihydrochloride (intermediate C1) and 3,5-diethoxy-benzaldehyde (intermediate D5) | ISP [M + H]+ 391.2 |
| 42 | 376.89 | 3-[4-(2-chloro-pyrimidin-4-ylamino)-piperidin-1-ylmethyl]-5-isopropoxy-phenol | (2-chloro-pyrimidin-4-yl)-piperidin-4-yl-amine dihydrochloride (intermediate C1) and 3-hydroxy-5-isopropoxy-benzaldehyde (intermediate D6) | ISP [M + H]+ 377.3 |
| 43 | 418.97 | (2-chloro-pyrimidin-4-yl)-[1-(3,5-diisopropoxy-benzyl)-piperidin-4-yl]-amine | (2-chloro-pyrimidin-4-yl)-piperidin-4-yl-amine dihydrochloride (intermediate C1) and 3,5-diisopropoxy-benzaldehyde (intermediate D7) | ISP [M + H]+ 419.2 |
| 44 | 532.81 | (2-chloro-pyrimidin-4-yl)-[1-(3-ethoxy-4-iodo-5-methoxymethoxy-benzyl)-piperidin-4-yl]-amine | (2-chloro-pyrimidin-4-yl)-piperidin-4-yl-amine dihydrochloride (intermediate C1) and 3-ethoxy-4-iodo-5-methoxymethoxy-benzaldehyde (intermediate D8) | ISP [M + H]+ 533.1 |
| 45 | 425.36 | [1-(2-chloro-3,5-diethoxy-benzyl)-piperidin-4-yl]-(2-chloro-pyrimidin-4-yl)-amine | (2-chloro-pyrimidin-4-yl)-piperidin-4-yl-amine dihydrochloride (intermediate C1) and 2-chloro-3,5-diethoxy-benzaldehyde (intermediate D9) | ISP [M + H]+ 425.2 |
| 46 | 374.92 | (2-chloro-6-methyl-pyrimidin-4-yl)-[1-(3-ethoxy-4-methyl-benzyl)-piperidin-4-yl]-amine | (2-chloro-6-methyl-pyrimidin-4-yl)-piperidin-4-yl-amine dihydrochloride (intermediate C2) and 3-ethoxy-4-methyl-benzaldehyde (intermediate D10) | ISP [M + H]+ 375.3 |
| 47 | 378.88 | (2-chloro-6-methyl-pyrimidin-4-yl)-[1-(3-ethoxy-4-fluoro-benzyl)-piperidin-4-yl]-amine | (2-chloro-6-methyl-pyrimidin-4-yl)-piperidin-4-yl-amine dihydrochloride (intermediate C2) and 3-ethoxy-4-fluoro-benzaldehyde (intermediate D1) | ISP [M + H]+ 379.3 |
| 48 | 395.33 | [1-(4-chloro-3-ethoxy-benzyl)-piperidin-4-yl]-(2-chloro-6-methyl-pyrimidin-4-yl)-amine | (2-chloro-6-methyl-pyrimidin-4-yl)-piperidin-4-yl-amine dihydrochloride (intermediate C2) and 4-chloro-3-ethoxy-benzaldehyde (intermediate D2) | ISP [M + H]+ 395.2 |

TABLE 4-continued

| No | MW | Compound Name | Starting Materials | [M + H]+ or [M − H]− found |
|---|---|---|---|---|
| 49 | 404.94 | (2-chloro-6-methyl-pyrimidin-4-yl)-[1-(3,4-diethoxy-benzyl)-piperidin-4-yl]-amine | (2-chloro-6-methyl-pyrimidin-4-yl)-piperidin-4-yl-amine dihydrochloride (intermediate C2) and 3,4-diethoxy-benzaldehyde (commercially available) | ISP [M + H]+ 405.4 |
| 50 | 418.97 | (2-chloro-6-methyl-pyrimidin-4-yl)-[1-(3-ethoxy-4-isopropoxy-benzyl)-piperidin-4-yl]-amine | (2-chloro-6-methyl-pyrimidin-4-yl)-piperidin-4-yl-amine dihydrochloride (intermediate C2) and 3-ethoxy-4-isopropoxy-benzaldehyde (commercially available) | ISP [M + H]+ 419.2 |
| 51 | 404.94 | (2-chloro-6-methyl-pyrimidin-4-yl)-[1-(4-methoxy-3-propoxy-benzyl)-piperidin-4-yl]-amine | (2-chloro-6-methyl-pyrimidin-4-yl)-piperidin-4-yl-amine dihydrochloride (intermediate C2) and 4-methoxy-3-propoxy-benzaldehyde (intermediate D11) | ISP [M + H]+ 405.3 |
| 52 | 408.90 | (2-chloro-6-methyl-pyrimidin-4-yl)-{1-[3-(2-fluoro-ethoxy)-4-methoxy-benzyl]-piperidin-4-yl}-amine | (2-chloro-6-methyl-pyrimidin-4-yl)-piperidin-4-yl-amine dihydrochloride (intermediate C2) and 3-(2-fluoro-ethoxy)-4-methoxy-benzaldehyde (intermediate D12) | ISP [M + H]+ 409.2 |
| 53 | 444.88 | (2-chloro-6-methyl-pyrimidin-4-yl)-{1-[4-methoxy-3-(2,2,2-trifluoro-ethoxy)-benzyl]-piperidin-4-yl}-amine | (2-chloro-6-methyl-pyrimidin-4-yl)-piperidin-4-yl-amine dihydrochloride (intermediate C2) and 4-methoxy-3-(2,2,2-trifluoro-ethoxy)-benzaldehyde (intermediate D13) | ISP [M + H]+ 445.2 |
| 54 | 402.93 | [1-(3-allyloxy-4-methoxy-benzyl)-piperidin-4-yl]-(2-chloro-6-methyl-pyrimidin-4-yl)-amine | (2-chloro-6-methyl-pyrimidin-4-yl)-piperidin-4-yl-amine dihydrochloride (intermediate C2) and 3-allyloxy-4-methoxy-benzaldehyde (intermediate D14) | ISP [M + H]+ 403.3 |
| 55 | 418.97 | [1-(3-butoxy-4-methoxy-benzyl)-piperidin-4-yl]-(2-chloro-6-methyl-pyrimidin-4-yl)-amine | (2-chloro-6-methyl-pyrimidin-4-yl)-piperidin-4-yl-amine dihydrochloride (intermediate C2) and 3-butoxy-4-methoxy-benzaldehyde (intermediate D4) | ISP [M + H]+ 419.2 |
| 56 | 418.97 | (2-chloro-6-methyl-pyrimidin-4-yl)-[1-(3-isobutoxy-4-methoxy-benzyl)-piperidin-4-yl]-amine | (2-chloro-6-methyl-pyrimidin-4-yl)-piperidin-4-yl-amine dihydrochloride (intermediate C2) and 3-isobutoxy-4-methoxy-benzaldehyde (intermediate D15) | ISP [M + H]+ 419.2 |
| 57 | 442.99 | (2-chloro-6-methyl-pyrimidin-4-yl)-[1-(8-ethoxy-2,2-dimethyl-2H-chromen-6-ylmethyl)-piperidin-4-yl]-amine | (2-chloro-6-methyl-pyrimidin-4-yl)-piperidin-4-yl-amine dihydrochloride (intermediate C2) and 8-ethoxy-2,2-dimethyl-2H-chromene-6-carbaldehyde (intermediate D16) | ISP [M + H]+ 443.3 |
| 58 | 404.94 | (2-chloro-6-methyl-pyrimidin-4-yl)-[1-(3,5-diethoxy-benzyl)-piperidin-4-yl]-amine | (2-chloro-6-methyl-pyrimidin-4-yl)-piperidin-4-yl-amine dihydrochloride (intermediate C2) and 3,5-diethoxy-benzaldehyde (intermediate D5) | ISP [M + H]+ 405.4 |
| 59 | 433.00 | (2-chloro-6-methyl-pyrimidin-4-yl)-[1-(3,5-diisopropoxy-benzyl)-piperidin-4-yl]-amine | (2-chloro-6-methyl-pyrimidin-4-yl)-piperidin-4-yl-amine dihydrochloride (intermediate C2) and 3,5-diisopropoxy-benzaldehyde (intermediate D7) | ISP [M + H]+ 433.3 |
| 60 | 439.39 | [1-(4-chloro-3,5-diethoxy-benzyl)-piperidin-4-yl]-(2-chloro-6-methyl-pyrimidin-4-yl)-amine | (2-chloro-6-methyl-pyrimidin-4-yl)-piperidin-4-yl-amine dihydrochloride (intermediate C2) and 4-chloro-3,5-diethoxy-benzaldehyde (intermediate D17) | ISP [M + H]+ 439.2 |
| 61 | 483.84 | [1-(4-bromo-3,5-diethoxy-benzyl)-piperidin-4-yl]-(2-chloro-6-methyl-pyrimidin-4-yl)-amine | (2-chloro-6-methyl-pyrimidin-4-yl)-piperidin-4-yl-amine dihydrochloride (intermediate C2) and 4-bromo-3,5-diethoxy-benzaldehyde (intermediate D18) | ISP [M + H]+ 485.2 |

TABLE 4-continued

| No | MW | Compound Name | Starting Materials | [M + H]+ or [M − H]− found |
|---|---|---|---|---|
| 62 | 470.02 | (2-chloro-6-methyl-pyrimidin-4-yl)-[1-(3,5-diethoxy-4-pyrrol-1-yl-benzyl)-piperidin-4-yl]-amine | (2-chloro-6-methyl-pyrimidin-4-yl)-piperidin-4-yl-amine dihydrochloride (intermediate C2) and 3,5-diethoxy-4-pyrrol-1-yl-benzaldehyde (intermediate D19) | ISP [M + H]+ 470.3 |
| 63 | 395.33 | (2,6-dichloro-pyrimidin-4-yl)-[1-(3-ethoxy-4-methyl-benzyl)-piperidin-4-yl]-amine | (2,6-dichloro-pyrimidin-4-yl)-piperidin-4-yl-amine dihydrochloride (intermediate C3) and 3-ethoxy-4-methyl-benzaldehyde (intermediate D10) | ISP [M + H]+ 395.3 |
| 64 | 399.30 | (2,6-dichloro-pyrimidin-4-yl)-[1-(3-ethoxy-4-fluoro-benzyl)-piperidin-4-yl]-amine | (2,6-dichloro-pyrimidin-4-yl)-piperidin-4-yl-amine dihydrochloride (intermediate C3) and 3-ethoxy-4-fluoro-benzaldehyde (intermediate D1) | ISP [M + H]+ 399.2 |
| 65 | 415.75 | [1-(4-chloro-3-ethoxy-benzyl)-piperidin-4-yl]-(2,6-dichloro-pyrimidin-4-yl)-amine | (2,6-dichloro-pyrimidin-4-yl)-piperidin-4-yl-amine dihydrochloride (intermediate C3) and 4-chloro-3-ethoxy-benzaldehyde (intermediate D2) | ISP [M + H]+ 417.2 |
| 66 | 397.31 | 4-[4-(2,6-dichloro-pyrimidin-4-ylamino)-piperidin-1-ylmethyl]-2-ethoxy-phenol | (2,6-dichloro-pyrimidin-4-yl)-piperidin-4-yl-amine dihydrochloride (intermediate C3) and 3-ethoxy-4-hydroxy-benzaldehyde (commercially available) | ISP [M + H]+ 397.2 |
| 67 | 411.33 | (2,6-dichloro-pyrimidin-4-yl)-[1-(3-ethoxy-4-methoxy-benzyl)-piperidin-4-yl]-amine | (2,6-dichloro-pyrimidin-4-yl)-piperidin-4-yl-amine dihydrochloride (intermediate C3) and 3-ethoxy-4-methoxy-benzaldehyde (commercially available) | ISP [M + H]+ 411.3 |
| 68 | 439.39 | (2,6-dichloro-pyrimidin-4-yl)-[1-(3-ethoxy-4-isopropoxy-benzyl)-piperidin-4-yl]-amine | (2,6-dichloro-pyrimidin-4-yl)-piperidin-4-yl-amine dihydrochloride (intermediate C3) and 3-ethoxy-4-isopropoxy-benzaldehyde (commercially available) | ISP [M + H]+ 439.2 |
| 69 | 467.44 | (2,6-dichloro-pyrimidin-4-yl)-{1-[3-ethoxy-4-(1-ethyl-propoxy)-benzyl]-piperidin-4-yl}-amine | (2,6-dichloro-pyrimidin-4-yl)-piperidin-4-yl-amine dihydrochloride (intermediate C3) and 3-ethoxy-4-(1-ethyl-propoxy)-benzaldehyde (intermediate D3) | ISP [M + H]+ 467.2 |
| 70 | 429.32 | (2,6-dichloro-pyrimidin-4-yl)-{1-[3-(2-fluoro-ethoxy)-4-methoxy-benzyl]-piperidin-4-yl}-amine | (2,6-dichloro-pyrimidin-4-yl)-piperidin-4-yl-amine dihydrochloride (intermediate C3) and 3-(2-fluoro-ethoxy)-4-methoxy-benzaldehyde (intermediate D12) | ISP [M + H]+ 429.2 |
| 71 | 423.34 | [1-(3-allyloxy-4-methoxy-benzyl)-piperidin-4-yl]-(2,6-dichloro-pyrimidin-4-yl)-amine | (2,6-dichloro-pyrimidin-4-yl)-piperidin-4-yl-amine dihydrochloride (intermediate C3) and 3-allyloxy-4-methoxy-benzaldehyde (intermediate D14) | ISP [M + H]+ 423.2 |
| 72 | 439.39 | [1-(3-butoxy-4-methoxy-benzyl)-piperidin-4-yl]-(2,6-dichloro-pyrimidin-4-yl)-amine | (2,6-dichloro-pyrimidin-4-yl)-piperidin-4-yl-amine dihydrochloride (intermediate C3) and 3-butoxy-4-methoxy-benzaldehyde (intermediate D4) | ISP [M + H]+ 439.2 |
| 73 | 439.39 | (2,6-dichloro-pyrimidin-4-yl)-[1-(3-isobutoxy-4-methoxy-benzyl)-piperidin-4-yl]-amine | (2,6-dichloro-pyrimidin-4-yl)-piperidin-4-yl-amine dihydrochloride (intermediate C3) and 3-isobutoxy-4-methoxy-benzaldehyde (intermediate D15) | ISP [M + H]+ 439.2 |
| 74 | 463.41 | (2,6-dichloro-pyrimidin-4-yl)-[1-(8-ethoxy-2,2-dimethyl-2H-chromen-6-ylmethyl)-piperidin-4-yl]-amine | (2,6-dichloro-pyrimidin-4-yl)-piperidin-4-yl-amine dihydrochloride (intermediate C3) and 8-ethoxy-2,2-dimethyl-2H-chromene-6-carbaldehyde (intermediate D16) | ISP [M + H]+ 463.2 |

TABLE 4-continued

| No | MW | Compound Name | Starting Materials | [M + H]+ or [M − H]− found |
|---|---|---|---|---|
| 75 | 425.36 | (2,6-dichloro-pyrimidin-4-yl)-[1-(3,5-diethoxy-benzyl)-piperidin-4-yl]-amine | (2,6-dichloro-pyrimidin-4-yl)-piperidin-4-yl-amine dihydrochloride (intermediate C3) and 3,5-diethoxy-benzaldehyde (intermediate D5) | ISP [M + H]+ 425.2 |
| 76 | 411.33 | 3-[4-(2,6-dichloro-pyrimidin-4-ylamino)-piperidin-1-ylmethyl]-5-isopropoxy-phenol | (2,6-dichloro-pyrimidin-4-yl)-piperidin-4-yl-amine dihydrochloride (intermediate C3) and 3-hydroxy-5-isopropoxy-benzaldehyde (intermediate D6) | ISP [M + H]+ 411.3 |
| 77 | 453.41 | (2,6-dichloro-pyrimidin-4-yl)-[1-(3,5-diisopropoxy-benzyl)-piperidin-4-yl]-amine | (2,6-dichloro-pyrimidin-4-yl)-piperidin-4-yl-amine dihydrochloride (intermediate C3) and 3,5-diisopropoxy-benzaldehyde (intermediate D7) | ISP [M + H]+ 453.2 |
| 78 | 443.35 | (2,6-dichloro-pyrimidin-4-yl)-[1-(3,5-diethoxy-4-fluoro-benzyl)-piperidin-4-yl]-amine | (2,6-dichloro-pyrimidin-4-yl)-piperidin-4-yl-amine dihydrochloride (intermediate C3) and 3,5-diethoxy-4-fluoro-benzaldehyde (intermediate D20) | ISP [M + H]+ 443.3 |
| 79 | 459.80 | [1-(4-chloro-3,5-diethoxy-benzyl)-piperidin-4-yl]-(2,6-dichloro-pyrimidin-4-yl)-amine | (2,6-dichloro-pyrimidin-4-yl)-piperidin-4-yl-amine dihydrochloride (intermediate C3) and 4-chloro-3,5-diethoxy-benzaldehyde (intermediate D17) | ISP [M + H]+ 459.2 |
| 80 | 504.26 | [1-(4-bromo-3,5-diethoxy-benzyl)-piperidin-4-yl]-(2,6-dichloro-pyrimidin-4-yl)-amine | (2,6-dichloro-pyrimidin-4-yl)-piperidin-4-yl-amine dihydrochloride (intermediate C3) and 4-bromo-3,5-diethoxy-benzaldehyde (intermediate D18) | ISP [M + H]+ 505.0 |
| 81 | 490.43 | (2,6-dichloro-pyrimidin-4-yl)-[1-(3,5-diethoxy-4-pyrrol-1-yl-benzyl)-piperidin-4-yl]-amine | (2,6-dichloro-pyrimidin-4-yl)-piperidin-4-yl-amine dihydrochloride (intermediate C3) and 3,5-diethoxy-4-pyrrol-1-yl-benzaldehyde (intermediate D19) | ISP [M + H]+ 490.1 |
| 82 | 372.47 | 4-[1-(3-ethoxy-4-methyl-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3-ethoxy-4-methyl-benzaldehyde (intermediate D10) | ISP [M + H]+ 373.3 |
| 83 | 376.43 | 4-[1-(3-ethoxy-4-fluoro-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3-ethoxy-4-fluoro-benzaldehyde (intermediate D1) | ISP [M + H]+ 377.3 |
| 84 | 392.89 | 4-[1-(4-chloro-3-ethoxy-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 4-chloro-3-ethoxy-benzaldehyde (intermediate D2) | ISP [M + H]+ 393.2 |
| 85 | 374.44 | 4-[1-(3-ethoxy-4-hydroxy-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3-ethoxy-4-hydroxy-benzaldehyde (commercially available) | ISP [M + H]+ 375.3 |
| 86 | 388.47 | 4-[1-(3-ethoxy-4-methoxy-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3-ethoxy-4-methoxy-benzaldehyde (commercially available) | ISP [M + H]+ 389.3 |
| 87 | 416.52 | 4-[1-(3-ethoxy-4-isopropoxy-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3-ethoxy-4-isopropoxy-benzaldehyde (commercially available) | ISP [M + H]+ 417.3 |

TABLE 4-continued

| No | MW | Compound Name | Starting Materials | [M + H]+ or [M − H]− found |
|---|---|---|---|---|
| 88 | 402.49 | 4-methoxy-6-[1-(4-methoxy-3-propoxy-benzyl)-piperidin-4-ylamino]-pyrimidin-2-ol | 4-methoxy-6-(piperidin-4-ylamino)-pyrimidin-2-ol dihydrochloride (intermediate C4) and 4-methoxy-3-propoxy-benzaldehyde (intermediate D11) | ISP [M + H]+ 403.4 |
| 89 | 406.46 | 4-{1-[3-(2-fluoro-ethoxy)-4-methoxy benzyl]-piperidin-4-ylamino}-6-methoxy-pyrimidin-2-ol | 4-methoxy-6-(piperidin-4-ylamino)-pyrimidin-2-ol dihydrochloride (intermediate C4) and 3-(2-fluoro-ethoxy)-4-methoxy-benzaldehyde (intermediate D12) | ISP [M + H]+ 407.4 |
| 90 | 400.48 | 4-[1-(3-allyloxy-4-methoxy-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3-allyloxy-4-methoxy-benzaldehyde (intermediate D14) | ISP [M + H]+ 401.3 |
| 91 | 416.52 | 4-[1-(3-butoxy-4-methoxy-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3-butoxy-4-methoxy-benzaldehyde (intermediate D4) | ISP [M + H]+ 417.3 |
| 92 | 416.52 | 4-[1-(3-isobutoxy-4-methoxy-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3-isobutoxy-4-methoxy-benzaldehyde (intermediate D15) | ISP [M + H]+ 417.3 |
| 93 | 440.54 | 4-[1-(8-ethoxy-2,2-dimethyl-2H-chromen-6-ylmethyl)-piperidin-4-ylamino]-6-methoxy-pyrimidin-2-ol | 4-methoxy-6-(piperidin-4-ylamino)-pyrimidin-2-ol dihydrochloride (intermediate C4) and 8-ethoxy-2,2-dimethyl-2H-chromene-6-carbaldehyde (intermediate D16) | ISP [M + H]+ 441.3 |
| 94 | 402.49 | 4-[1-(3,5-diethoxy-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3,5-diethoxy-benzaldehyde (intermediate D5) | ISP [M + H]+ 403.4 |
| 95 | 430.55 | 4-[1-(3,5-diisopropoxy-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3,5-diisopropoxy-benzaldehyde (intermediate D7) | ISP [M + H]+ 431.4 |
| 96 | 420.48 | 4-[1-(3,5-diethoxy-4-fluoro-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3,5-diethoxy-4-fluoro-benzaldehyde (intermediate D20) | ISP [M + H]+ 421.3 |
| 97 | 436.94 | 4-[1-(4-chloro-3,5-diethoxy-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 4-chloro-3,5-diethoxy-benzaldehyde (intermediate D17) | ISP [M + H]+ 437.3 |
| 98 | 467.57 | 4-[1-(3,5-diethoxy-4-pyrrol-1-yl-benzyl)-piperidin-4-ylamino]-6-methoxy-pyrimidin-2-ol | 4-methoxy-6-(piperidin-4-ylamino)-pyrimidin-2-ol dihydrochloride (intermediate C4) and 3,5-diethoxy-4-pyrrol-1-yl-benzaldehyde (intermediate D19) | ISP [M + H]+ 468.4 |
| 99 | 418.92 | 2-chloro-6-[1-(3-ethoxy-4-methyl-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride (intermediate C5) and 3-ethoxy-4-methyl-benzaldehyde (intermediate D10) | ESI [M + H]+ 419.7 |

TABLE 4-continued

| No | MW | Compound Name | Starting Materials | [M + H]+ or [M − H]− found |
|---|---|---|---|---|
| 100 | 422.89 | 2-chloro-6-[1-(3-ethoxy-4-fluoro-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3-ethoxy-4-fluoro-benzaldehyde (intermediate D1) | ISP [M + H]+ 423.2 |
| 101 | 439.34 | 2-chloro-6-[1-(4-chloro-3-ethoxy-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 4-chloro-3-ethoxy-benzaldehyde (intermediate D2) | ISP [M + H]+ 439.2 |
| 102 | 434.92 | 2-chloro-6-[1-(3-ethoxy-4-methoxy-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3-ethoxy-4-methoxy-benzaldehyde (commercially available) | ESI [M + H]+ 434.7 |
| 103 | 462.98 | 2-chloro-6-[1-(3-ethoxy-4-isopropoxy-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3-ethoxy-4-isopropoxy-benzaldehyde (commercially available) | ISP [M + H]+ 463.2 |
| 104 | 452.91 | 2-chloro-6-{1-[3-(2-fluoro-ethoxy)-4-methoxy-benzyl]-piperidin-4-ylamino}-pyrimidine-4-carboxylic acid methyl ester | 2-chloro-6-(piperidin-4-ylamino)-pyrimidine-4-carboxylic acid methyl ester dihydrochloride_(intermediate C5) and 3-(2-fluoro-ethoxy)-4-methoxy-benzaldehyde (intermediate D12) | ESI [M + H]+ 452.7 |
| 105 | 446.93 | 6-[1-(3-allyloxy-4-methoxy-benzyl)-piperidin-4-ylamino]-2-chloro-pyrimidine-4-carboxylic acid methyl ester | 2-chloro-6-(piperidin-4-ylamino)-pyrimidine-4-carboxylic acid methyl ester dihydrochloride_(intermediate C5) and 3-allyloxy-4-methoxy-benzaldehyde (intermediate D14) | ESI [M + H]+ 446.7 |
| 106 | 462.98 | 6-[1-(3-butoxy-4-methoxy-benzyl)-piperidin-4-ylamino]-2-chloro-pyrimidine-4-carboxylic acid methyl ester | 2-chloro-6-(piperidin-4-ylamino)-pyrimidine-4-carboxylic acid methyl ester dihydrochloride_(intermediate C5) and 3-butoxy-4-methoxy-benzaldehyde (intermediate D4) | ESI [M + H]+ 462.8 |
| 107 | 462.98 | 2-chloro-6-[1-(3-isobutoxy-4-methoxy-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3-isobutoxy-4-methoxy-benzaldehyde (intermediate D15) | ISP [M + H]+ 463.2 |
| 108 | 487.00 | 2-chloro-6-[1-(8-ethoxy-2,2-dimethyl-2H-chromen-6-ylmethyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 8-ethoxy-2,2-dimethyl-2H-chromene-6-carbaldehyde (intermediate D16) | ISP [M + H]+ 487.3 |
| 109 | 448.95 | 2-chloro-6-[1-(3,5-diethoxy-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3,5-diethoxy-benzaldehyde (intermediate D5) | ESI [M + H]+ 448.7 |
| 110 | 434.92 | 2-chloro-6-[1-(3-hydroxy-5-isopropoxy-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3-hydroxy-5-isopropoxy-benzaldehyde (intermediate D6) | ESI [M + H]+ 434.7 |

TABLE 4-continued

| No | MW | Compound Name | Starting Materials | [M + H]⁺ or [M − H]⁻ found |
|---|---|---|---|---|
| 111 | 477.00 | 2-chloro-6-[1-(3,5-diisopropoxy-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3,5-diisopropoxy-benzaldehyde (intermediate D7) | ESI [M + H]⁺ 476.8 |
| 112 | 466.94 | 2-chloro-6-[1-(3,5-diethoxy-4-fluoro-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3,5-diethoxy-4-fluoro-benzaldehyde (intermediate D20) | ISP [M + H]⁺ 467.3 |
| 113 | 527.84 | 6-[1-(4-bromo-3,5-diethoxy-benzyl)-piperidin-4-ylamino]-2-chloro-pyrimidine-4-carboxylic acid methyl ester | 2-chloro-6-(piperidin-4-ylamino)-pyrimidine-4-carboxylic acid methyl ester dihydrochloride_(intermediate C5) and 4-bromo-3,5-diethoxy-benzaldehyde (intermediate D18) | ESI [M + H]⁺ 528.7 |
| 114 | 590.84 | 2-chloro-6-[1-(3-ethoxy-4-iodo-5-methoxymethoxy-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3-ethoxy-4-iodo-5-methoxymethoxy-benzaldehyde (intermediate D8) | ESI [M + H]⁺ 590.8 |
| 115 | 514.03 | 2-chloro-6-[1-(3,5-diethoxy-4-pyrrol-1-yl-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3,5-diethoxy-4-pyrrol-1-yl-benzaldehyde (intermediate D19) | ISP [M + H]⁺ 514.3 |
| 116 | 483.39 | 2-chloro-6-[1-(2-chloro-3,5-diethoxy-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 2-chloro-3,5-diethoxy-benzaldehyde (intermediate D9) | ESI [M − H]⁻ 482.8 |
| 117 | 479.92 | 2-chloro-6-[1-(3-ethoxy-4-methoxy-5-nitro-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3-ethoxy-4-methoxy-5-nitro-benzaldehyde (intermediate D21) | ESI [M + H]⁺ 477.8 |
| 118 | 433.94 | 2-chloro-6-[1-(3-ethylamino-4-methoxy-benzyl)-piperidin-4-ylamino]-pyrimidine-4-carboxylic acid methyl ester | 2-chloro-6-(piperidin-4-ylamino)-pyrimidine-4-carboxylic acid methyl ester dihydrochloride_(intermediate C5) and 3-ethylamino-4-methoxy-benzaldehyde (intermediate D22) | ESI [M + H]⁺ 433.7 |
| 119 | 438.36 | N-{2-chloro-6-[1-(4-chloro-3-ethoxy-benzyl)-piperidin-4-ylamino]-pyrimidin-4-yl}-acetamide | N-[2-chloro-6-(piperidin-4-ylamino)-pyrimidin-4-yl]-acetamide dihydrochloride (intermediate C6) and 4-chloro-3-ethoxy-benzaldehyde (intermediate D2) | ISP [M + H]⁺ 438.3 |
| 120 | 378.88 | (2-chloro-5-fluoro-pyrimidin-4-yl)-[1-(3-ethoxy-4-methyl-benzyl)-piperidin-4-yl]-amine | (2-chloro-5-fluoro-pyrimidin-4-yl)-piperidin-4-yl-amine dihydrochloride (intermediate C7) and 3-ethoxy-4-methyl-benzaldehyde (intermediate D10) | ISP [M + H]⁺ 379.3 |
| 121 | 382.84 | (2-chloro-5-fluoro-pyrimidin-4-yl)-[1-(3-ethoxy-4-fluoro-benzyl)-piperidin-4-yl]-amine | (2-chloro-5-fluoro-pyrimidin-4-yl)-piperidin-4-yl-amine dihydrochloride (intermediate C7) and 3-ethoxy-4-fluoro-benzaldehyde (intermediate D1) | ISP [M + H]⁺ 383.1 |

TABLE 4-continued

| No | MW | Compound Name | Starting Materials | [M + H]⁺ or [M − H]⁻ found |
|---|---|---|---|---|
| 122 | 399.30 | [1-(4-chloro-3-ethoxy-benzyl)-piperidin-4-yl]-(2-chloro-5-fluoro-pyrimidin-4-yl)-amine | (2-chloro-5-fluoro-pyrimidin-4-yl)-piperidin-4-yl-amine dihydrochloride (intermediate C7) and 4-chloro-3-ethoxy-benzaldehyde (intermediate D2) | ISP [M + H]⁺ 399.2 |
| 123 | 394.88 | (2-chloro-5-fluoro-pyrimidin-4-yl)-[1-(3-ethoxy-4-methoxy-benzyl)-piperidin-4-yl]-amine | (2-chloro-5-fluoro-pyrimidin-4-yl)-piperidin-4-yl-amine dihydrochloride (intermediate C7) and 3-ethoxy-4-methoxy-benzaldehyde (commercially available) | ISP [M + H]⁺ 395.3 |
| 124 | 408.90 | (2-chloro-5-fluoro-pyrimidin-4-yl)-[1-(3,4-diethoxy-benzyl)-piperidin-4-yl]-amine | (2-chloro-5-fluoro-pyrimidin-4-yl)-piperidin-4-yl-amine dihydrochloride (intermediate C7) and 3,4-diethoxy-benzaldehyde (commercially available) | ISP [M + H]⁺ 409.2 |
| 125 | 422.93 | (2-chloro-5-fluoro-pyrimidin-4-yl)-[1-(3-ethoxy-4-isopropoxy-benzyl)-piperidin-4-yl]-amine | (2-chloro-5-fluoro-pyrimidin-4-yl)-piperidin-4-yl-amine dihydrochloride (intermediate C7) and 3-ethoxy-4-isopropoxy-benzaldehyde (commercially available) | ISP [M + H]⁺ 423.2 |
| 126 | 408.90 | (2-chloro-5-fluoro-pyrimidin-4-yl)-[1-(4-methoxy-3-propoxy-benzyl)-piperidin-4-yl]-amine | (2-chloro-5-fluoro-pyrimidin-4-yl)-piperidin-4-yl-amine dihydrochloride (intermediate C7) and 4-methoxy-3-propoxy-benzaldehyde (intermediate D11) | ISP [M + H]⁺ 409.2 |
| 127 | 412.87 | (2-chloro-5-fluoro-pyrimidin-4-yl)-{1-[3-(2-fluoro-ethoxy)-4-methoxy-benzyl]-piperidin-4-yl}-amine | (2-chloro-5-fluoro-pyrimidin-4-yl)-piperidin-4-yl-amine dihydrochloride (intermediate C7) and 3-(2-fluoro-ethoxy)-4-methoxy-benzaldehyde (intermediate D12) | ISP [M + H]⁺ 413.2 |
| 128 | 448.85 | (2-chloro-5-fluoro-pyrimidin-4-yl)-{1-[4-methoxy-3-(2,2,2-trifluoro-ethoxy)-benzyl]-piperidin-4-yl}-amine | (2-chloro-5-fluoro-pyrimidin-4-yl)-piperidin-4-yl-amine dihydrochloride (intermediate C7) and 4-methoxy-3-(2,2,2-trifluoro-ethoxy)-benzaldehyde (intermediate D13) | ISP [M + H]⁺ 449.1 |
| 129 | 406.89 | [1-(3-allyloxy-4-methoxy-benzyl)-piperidin-4-yl]-(2-chloro-5-fluoro-pyrimidin-4-yl)-amine | (2-chloro-5-fluoro-pyrimidin-4-yl)-piperidin-4-yl-amine dihydrochloride (intermediate C7) and 3-allyloxy-4-methoxy-benzaldehyde (intermediate D14) | ISP [M + H]⁺ 407.3 |
| 130 | 422.93 | [1-(3-butoxy-4-methoxy-benzyl)-piperidin-4-yl]-(2-chloro-5-fluoro-pyrimidin-4-yl)-amine | (2-chloro-5-fluoro-pyrimidin-4-yl)-piperidin-4-yl-amine dihydrochloride (intermediate C7) and 3-butoxy-4-methoxy-benzaldehyde (intermediate D4) | ISP [M + H]⁺ 423.2 |
| 131 | 422.93 | (2-chloro-5-fluoro-pyrimidin-4-yl)-[1-(3-isobutoxy-4-methoxy-benzyl)-piperidin-4-yl]-amine | (2-chloro-5-fluoro-pyrimidin-4-yl)-piperidin-4-yl-amine dihydrochloride (intermediate C7) and 3-isobutoxy-4-methoxy-benzaldehyde (intermediate D15) | ISP [M + H]⁺ 423.2 |
| 132 | 408.90 | (2-chloro-5-fluoro-pyrimidin-4-yl)-[1-(3,5-diethoxy-benzyl)-piperidin-4-yl]-amine | (2-chloro-5-fluoro-pyrimidin-4-yl)-piperidin-4-yl-amine dihydrochloride (intermediate C7) and 3,5-diethoxy-benzaldehyde (intermediate D5) | ISP [M + H]⁺ 409.3 |
| 133 | 436.96 | (2-chloro-5-fluoro-pyrimidin-4-yl)-[1-(3,5-diisopropoxy-benzyl)-piperidin-4-yl]-amine | (2-chloro-5-fluoro-pyrimidin-4-yl)-piperidin-4-yl-amine dihydrochloride (intermediate C7) and 3,5-diisopropoxy-benzaldehyde (intermediate D7) | ISP [M + H]⁺ 437.3 |
| 134 | 426.89 | (2-chloro-5-fluoro-pyrimidin-4-yl)-[1-(3,5-diethoxy-4-fluoro-benzyl)-piperidin-4-yl]-amine | (2-chloro-5-fluoro-pyrimidin-4-yl)-piperidin-4-yl-amine dihydrochloride (intermediate C7) and 3,5-diethoxy-4-fluoro-benzaldehyde (intermediate D20) | ISP [M + H]⁺ 427.2 |

TABLE 4-continued

| No | MW | Compound Name | Starting Materials | [M + H]+ or [M − H]− found |
|---|---|---|---|---|
| 135 | 443.35 | [1-(4-chloro-3,5-diethoxy-benzyl)-piperidin-4-yl]-(2-chloro-5-fluoro-pyrimidin-4-yl)-amine | (2-chloro-5-fluoro-pyrimidin-4-yl)-piperidin-4-yl-amine dihydrochloride (intermediate C7) and 4-chloro-3,5-diethoxy-benzaldehyde (intermediate D17) | ISP [M + H]+ 443.2 |
| 136 | 487.81 | [1-(4-bromo-3,5-diethoxy-benzyl)-piperidin-4-yl]-(2-chloro-5-fluoro-pyrimidin-4-yl)-amine | (2-chloro-5-fluoro-pyrimidin-4-yl)-piperidin-4-yl-amine dihydrochloride (intermediate C7) and 4-bromo-3,5-diethoxy-benzaldehyde (intermediate D18) | ISP [M + H]+ 487.1 |
| 137 | 473.98 | (2-chloro-5-fluoro-pyrimidin-4-yl)-[1-(3,5-diethoxy-4-pyrrol-1-yl-benzyl)-piperidin-4-yl]-amine | (2-chloro-5-fluoro-pyrimidin-4-yl)-piperidin-4-yl-amine dihydrochloride (intermediate C7) and 3,5-diethoxy-4-pyrrol-1-yl-benzaldehyde (intermediate D19) | ISP [M + H]+ 474.2 |
| 138 | 443.35 | [1-(2-chloro-3,5-diethoxy-benzyl)-piperidin-4-yl]-(2-chloro-5-fluoro-pyrimidin-4-yl)-amine | (2-chloro-5-fluoro-pyrimidin-4-yl)-piperidin-4-yl-amine dihydrochloride (intermediate C7) and 2-chloro-3,5-diethoxy-benzaldehyde (intermediate D9) | ISP [M + H]+ 443.2 |
| 139 | 390.18 | (2-chloro-5-methoxy-pyrimidin-4-yl)-[1-(3-ethoxy-4-methyl-benzyl)-piperidin-4-yl]-amine | (2-chloro-5-methoxy-pyrimidin-4-yl)-piperidin-4-yl-amine dihydrochloride (intermediate C8) and 3-ethoxy-4-methyl-benzaldehyde (intermediate D10) | ESI [M + H]+ 391.2 |
| 140 | 394.16 | (2-chloro-5-methoxy-pyrimidin-4-yl)-[1-(3-ethoxy-4-fluoro-benzyl)-piperidin-4-yl]-amine | (2-chloro-5-methoxy-pyrimidin-4-yl)-piperidin-4-yl-amine dihydrochloride (intermediate C8) and 3-ethoxy-4-fluoro-benzaldehyde (intermediate D1) | ESI [M + H]+ 395.2 |
| 141 | 410.13 | [1-(4-chloro-3-ethoxy-benzyl)-piperidin-4-yl]-(2-chloro-5-methoxy-pyrimidin-4-yl)-amine | (2-chloro-5-methoxy-pyrimidin-4-yl)-piperidin-4-yl-amine dihydrochloride (intermediate C8) and 4-chloro-3-ethoxy-benzaldehyde (intermediate D2) | ESI [M + H]+ 411.1 |
| 142 | 392.16 | 4-[4-(2-chloro-5-methoxy-pyrimidin-4-ylamino)-piperidin-1-ylmethyl]-2-ethoxy-phenol | (2-chloro-5-methoxy-pyrimidin-4-yl)-piperidin-4-yl-amine dihydrochloride (intermediate C8) and 3-ethoxy-4-hydroxy-benzaldehyde (commercially available) | ESI [M + H]+ 393.2 |
| 143 | 406.18 | (2-chloro-5-methoxy-pyrimidin-4-yl)-[1-(3-ethoxy-4-methoxy-benzyl)-piperidin-4-yl]-amine | (2-chloro-5-methoxy-pyrimidin-4-yl)-piperidin-4-yl-amine dihydrochloride (intermediate C8) and 3-ethoxy-4-methoxy-benzaldehyde (commercially available) | ESI [M + H]+ 407.2 |
| 144 | 434.21 | (2-chloro-5-methoxy-pyrimidin-4-yl)-[1-(3-ethoxy-4-isopropoxy-benzyl)-piperidin-4-yl]-amine | (2-chloro-5-methoxy-pyrimidin-4-yl)-piperidin-4-yl-amine dihydrochloride (intermediate C8) and 3-ethoxy-4-isopropoxy-benzaldehyde (commercially available) | ESI [M + H]+ 435.3 |
| 145 | 462.24 | (2-chloro-5-methoxy-pyrimidin-4-yl)-{1-[3-ethoxy-4-(1-ethyl-propoxy)-benzyl]-piperidin-4-yl}-amine | (2-chloro-5-methoxy-pyrimidin-4-yl)-piperidin-4-yl-amine dihydrochloride (intermediate C8) and 3-ethoxy-4-(1-ethyl-propoxy)-benzaldehyde (intermediate D3) | ESI [M + H]+ 463.3 |
| 146 | 424.17 | (2-chloro-5-methoxy-pyrimidin-4-yl)-{1-[3-(2-fluoro-ethoxy)-4-methoxy-benzyl]-piperidin-4-yl}-amine | (2-chloro-5-methoxy-pyrimidin-4-yl)-piperidin-4-yl-amine dihydrochloride (intermediate C8) and 3-(2-fluoro-ethoxy)-4-methoxy-benzaldehyde (intermediate D12) | ESI [M + H]+ 425.2 |
| 147 | 418.18 | [1-(3-allyloxy-4-methoxy-benzyl)-piperidin-4-yl]-(2- | (2-chloro-5-methoxy-pyrimidin-4-yl)-piperidin-4-yl-amine dihydrochloride | ESI [M + H]+ 419.3 |

TABLE 4-continued

| No | MW | Compound Name | Starting Materials | [M + H]+ or [M − H]− found |
|---|---|---|---|---|
| | | chloro-5-methoxy-pyrimidin-4-yl)-amine | (intermediate C8) and 3-allyloxy-4-methoxy-benzaldehyde (intermediate D14) | |
| 148 | 434.21 | [1-(3-butoxy-4-methoxy-benzyl)-piperidin-4-yl]-(2-chloro-5-methoxy-pyrimidin-4-yl)-amine | (2-chloro-5-methoxy-pyrimidin-4-yl)-piperidin-4-yl-amine dihydrochloride (intermediate C8) and 3-butoxy-4-methoxy-benzaldehyde (intermediate D4) | ESI [M + H]+ 435.3 |
| 149 | 458.21 | (2-chloro-5-methoxy-pyrimidin-4-yl)-[1-(8-ethoxy-2,2-dimethyl-2H-chromen-6-ylmethyl)-piperidin-4-yl]-amine | (2-chloro-5-methoxy-pyrimidin-4-yl)-piperidin-4-yl-amine dihydrochloride (intermediate C8) and 8-ethoxy-2,2-dimethyl-2H-chromene-6-carbaldehyde (intermediate D16) | ESI [M + H]+ 459.2 |
| 150 | 420.19 | (2-chloro-5-methoxy-pyrimidin-4-yl)-[1-(3,5-diethoxy-benzyl)-piperidin-4-yl]-amine | (2-chloro-5-methoxy-pyrimidin-4-yl)-piperidin-4-yl-amine dihydrochloride (intermediate C8) and 3,5-diethoxy-benzaldehyde (intermediate D5) | ESI [M + H]+ 421.3 |
| 151 | 448.22 | (2-chloro-5-methoxy-pyrimidin-4-yl)-[1-(3,5-diisopropoxy-benzyl)-piperidin-4-yl]-amine | (2-chloro-5-methoxy-pyrimidin-4-yl)-piperidin-4-yl-amine dihydrochloride (intermediate C8) and 3,5-diisopropoxy-benzaldehyde (intermediate D7) | ESI [M + H]+ 449.3 |
| 152 | 406.18 | 3-[4-(2-chloro-5-methoxy-pyrimidin-4-ylamino)-piperidin-1-ylmethyl]-5-isopropoxy-phenol | (2-chloro-5-methoxy-pyrimidin-4-yl)-piperidin-4-yl-amine dihydrochloride (intermediate C8) and 3-hydroxy-5-isopropoxy-benzaldehyde (intermediate D6) | ESI [M + H]+ 407.2 |
| 153 | 438.18 | (2-chloro-5-methoxy-pyrimidin-4-yl)-[1-(3,5-diethoxy-4-fluoro-benzyl)-piperidin-4-yl]-amine | (2-chloro-5-methoxy-pyrimidin-4-yl)-piperidin-4-yl-amine dihydrochloride (intermediate C8) and 3,5-diethoxy-4-fluoro-benzaldehyde (intermediate D20) | ESI [M + H]+ 439.2 |
| 154 | 454.15 | [1-(4-chloro-3,5-diethoxy-benzyl)-piperidin-4-yl]-(2-chloro-5-methoxy-pyrimidin-4-yl)-amine | (2-chloro-5-methoxy-pyrimidin-4-yl)-piperidin-4-yl-amine dihydrochloride (intermediate C8) and 4-chloro-3,5-diethoxy-benzaldehyde (intermediate D17) | ESI [M + H]+ 455.2 |
| 155 | 499.84 | [1-(4-bromo-3,5-diethoxy-benzyl)-piperidin-4-yl]-(2-chloro-5-methoxy-pyrimidin-4-yl)-amine | (2-chloro-5-methoxy-pyrimidin-4-yl)-piperidin-4-yl-amine dihydrochloride (intermediate C8) and 4-bromo-3,5-diethoxy-benzaldehyde (intermediate D18) | ESI [M + H]+ 499.2 |
| 156 | 435.20 | [1-(4-amino-3,5-diethoxy-benzyl)-piperidin-4-yl]-(2-chloro-5-methoxy-pyrimidin-4-yl)-amine | (2-chloro-5-methoxy-pyrimidin-4-yl)-piperidin-4-yl-amine dihydrochloride (intermediate C8) and 4-amino-3,5-diethoxy-benzaldehyde (intermediate D23) | ESI [M + H]+ 436.3 |
| 157 | 485.22 | (2-chloro-5-methoxy-pyrimidin-4-yl)-[1-(3,5-diethoxy-4-pyrrol-1-yl-benzyl)-piperidin-4-yl]-amine | (2-chloro-5-methoxy-pyrimidin-4-yl)-piperidin-4-yl-amine dihydrochloride (intermediate C8) and 3,5-diethoxy-4-pyrrol-1-yl-benzaldehyde (intermediate D19) | ESI [M − H]− 484.3 |
| 158 | 454.15 | [1-(2-chloro-3,5-diethoxy-benzyl)-piperidin-4-yl]-(2-chloro-5-methoxy-pyrimidin-4-yl)-amine | (2-chloro-5-methoxy-pyrimidin-4-yl)-piperidin-4-yl-amine dihydrochloride (intermediate C8) and 2-chloro-3,5-diethoxy-benzaldehyde (intermediate D9) | ESI [M + H]+ 455.2 |
| 159 | 404.92 | (2-chloro-6,7-dihydro-5H-cyclopentapyrimidin-4-yl)-[1-(3-ethoxy-4- | (2-chloro-6,7-dihydro-5H-cyclopentapyrimidin-4-yl)-piperidin-4-yl-amine | ISP [M + H]+ 405.4 |

TABLE 4-continued

| No | MW | Compound Name | Starting Materials | [M + H]⁺ or [M − H]⁻ found |
|---|---|---|---|---|
| | | fluoro-benzyl)-piperidin-4-yl]-amine | dihydrochloride (intermediate C9) and 3-ethoxy-4-fluoro-benzaldehyde (intermediate D1) | |
| 160 | 421.37 | (2-chloro-6,7-dihydro-5H-cyclopentapyrimidin-4-yl)-[1-(4-chloro-3-ethoxy-benzyl)-piperidin-4-yl]-amine | (2-chloro-6,7-dihydro-5H-cyclopentapyrimidin-4-yl)-piperidin-4-yl-amine dihydrochloride (intermediate C9) and 4-chloro-3-ethoxy-benzaldehyde (intermediate D2) | ISP [M + H]⁺ 421.2 |
| 161 | 402.93 | 4-[4-(2-chloro-6,7-dihydro-5H-cyclopentapyrimidin-4-ylamino)-piperidin-1-ylmethyl]-2-ethoxy-phenol | (2-chloro-6,7-dihydro-5H-cyclopentapyrimidin-4-yl)-piperidin-4-yl-amine dihydrochloride (intermediate C9) and 3-ethoxy-4-hydroxy-benzaldehyde (commercially available) | ISP [M + H]⁺ 403.4 |
| 162 | 416.96 | (2-chloro-6,7-dihydro-5H-cyclopentapyrimidin-4-yl)-[1-(3-ethoxy-4-methoxy-benzyl)-piperidin-4-yl]-amine | (2-chloro-6,7-dihydro-5H-cyclopentapyrimidin-4-yl)-piperidin-4-yl-amine dihydrochloride (intermediate C9) and 3-ethoxy-4-methoxy-benzaldehyde (commercially available) | ISP [M + H]⁺ 417.3 |
| 163 | 445.01 | (2-chloro-6,7-dihydro-5H-cyclopentapyrimidin-4-yl)-[1-(3-ethoxy-4-isopropoxy-benzyl)-piperidin-4-yl]-amine | (2-chloro-6,7-dihydro-5H-cyclopentapyrimidin-4-yl)-piperidin-4-yl-amine dihydrochloride (intermediate C9) and 3-ethoxy-4-isopropoxy-benzaldehyde (commercially available) | ISP [M + H]⁺ 445.3 |
| 164 | 473.06 | ((2-chloro-6,7-dihydro-5H-cyclopentapyrimidin-4-yl)-{1-[3-ethoxy-4-(1-ethyl-propoxy)-benzyl]-piperidin-4-yl}-amine | (2-chloro-6,7-dihydro-5H-cyclopentapyrimidin-4-yl)-piperidin-4-yl-amine dihydrochloride (intermediate C9) and 3-ethoxy-4-(1-ethyl-propoxy)-benzaldehyde (intermediate D3) | ISP [M + H]⁺ 473.3 |
| 165 | 481.02 | methanesulfonic acid 4-[4-(2-chloro-6,7-dihydro-5H-cyclopentapyrimidin-4-ylamino)-piperidin-1-ylmethyl]-2-ethoxy-phenyl ester | (2-chloro-6,7-dihydro-5H-cyclopentapyrimidin-4-yl)-piperidin-4-yl-amine dihydrochloride (intermediate C9) and methanesulfonic acid 2-ethoxy-4-formyl-phenyl ester (intermediate D24) | ISP [M + H]⁺ 481.2 |
| 166 | 434.95 | (2-chloro-6,7-dihydro-5H-cyclopentapyrimidin-4-yl)-{1-[3-(2-fluoro-ethoxy)-4-methoxy-benzyl]-piperidin-4-yl}-amine | (2-chloro-6,7-dihydro-5H-cyclopentapyrimidin-4-yl)-piperidin-4-yl-amine dihydrochloride (intermediate C9) and 3-(2-fluoro-ethoxy)-4-methoxy-benzaldehyde (intermediate D12) | ISP [M + H]⁺ 435.4 |
| 167 | 428.97 | [1-(3-allyloxy-4-methoxy-benzyl)-piperidin-4-yl]-(2-chloro-6,7-dihydro-5H-cyclopentapyrimidin-4-yl)-amine | (2-chloro-6,7-dihydro-5H-cyclopentapyrimidin-4-yl)-piperidin-4-yl-amine dihydrochloride (intermediate C9) and 3-allyloxy-4-methoxy-benzaldehyde (intermediate D14) | ISP [M + H]⁺ 429.3 |
| 168 | 445.01 | [1-(3-butoxy-4-methoxy-benzyl)-piperidin-4-yl]-(2-chloro-6,7-dihydro-5H-cyclopentapyrimidin-4-yl)-amine | (2-chloro-6,7-dihydro-5H-cyclopentapyrimidin-4-yl)-piperidin-4-yl-amine dihydrochloride (intermediate C9) and 3-butoxy-4-methoxy-benzaldehyde (intermediate D4) | ISP [M + H]⁺ 445.3 |
| 169 | 469.03 | (2-chloro-6,7-dihydro-5H-cyclopentapyrimidin-4-yl)-[1-(8-ethoxy-2,2-dimethyl-2H-chromen-6-ylmethyl)-piperidin-4-yl]-amine | (2-chloro-6,7-dihydro-5H-cyclopentapyrimidin-4-yl)-piperidin-4-yl-amine dihydrochloride (intermediate C9) and 8-ethoxy-2,2-dimethyl-2H-chromene-6-carbaldehyde (intermediate D16) | ISP [M + H]⁺ 469.3 |

TABLE 4-continued

| No | MW | Compound Name | Starting Materials | [M + H]+ or [M − H]− found |
|---|---|---|---|---|
| 170 | 430.98 | (2-chloro-6,7-dihydro-5H-cyclopentapyrimidin-4-yl)-[1-(3,5-diethoxy-benzyl)-piperidin-4-yl]-amine | (2-chloro-6,7-dihydro-5H-cyclopentapyrimidin-4-yl)-piperidin-4-yl-amine dihydrochloride (intermediate C9) and 3,5-diethoxy-benzaldehyde (intermediate D5) | ISP [M + H]+ 431.4 |
| 171 | 416.96 | 3-[4-(2-chloro-6,7-dihydro-5H-cyclopentapyrimidin-4-ylamino)-piperidin-1-ylmethyl]-5-isopropoxy-phenol | (2-chloro-6,7-dihydro-5H-cyclopentapyrimidin-4-yl)-piperidin-4-yl-amine dihydrochloride (intermediate C9) and 3-hydroxy-5-isopropoxy-benzaldehyde (intermediate D6) | ISP [M + H]+ 417.3 |
| 172 | 459.04 | (2-chloro-6,7-dihydro-5H-cyclopentapyrimidin-4-yl)-[1-(3,5-diisopropoxy-benzyl)-piperidin-4-yl]-amine | (2-chloro-6,7-dihydro-5H-cyclopentapyrimidin-4-yl)-piperidin-4-yl-amine dihydrochloride (intermediate C9) and 3,5-diisopropoxy-benzaldehyde (intermediate D7) | ISP [M + H]+ 459.3 |
| 173 | 493.05 | [1-(3-benzyloxy-5-ethoxy-benzyl)-piperidin-4-yl]-(2-chloro-6,7-dihydro-5H-cyclopentapyrimidin-4-yl)-amine | (2-chloro-6,7-dihydro-5H-cyclopentapyrimidin-4-yl)-piperidin-4-yl-amine dihydrochloride (intermediate C9) and 3-benzyloxy-5-ethoxy-benzaldehyde (intermediate D25) | ISP [M + H]+ 493.3 |
| 174 | 448.97 | (2-chloro-6,7-dihydro-5H-cyclopentapyrimidin-4-yl)-[1-(3,5-diethoxy-4-fluoro-benzyl)-piperidin-4-yl]-amine | (2-chloro-6,7-dihydro-5H-cyclopentapyrimidin-4-yl)-piperidin-4-yl-amine dihydrochloride (intermediate C9) and 3,5-diethoxy-4-fluoro-benzaldehyde (intermediate D20) | ISP [M + H]+ 449.2 |
| 175 | 496.06 | (2-chloro-6,7-dihydro-5H-cyclopentapyrimidin-4-yl)-[1-(3,5-diethoxy-4-pyrrol-1-yl-benzyl)-piperidin-4-yl]-amine | (2-chloro-6,7-dihydro-5H-cyclopentapyrimidin-4-yl)-piperidin-4-yl-amine dihydrochloride (intermediate C9) and 3,5-diethoxy-4-pyrrol-1-yl-benzaldehyde (intermediate D19) | ISP [M + H]+ 496.4 |
| 176 | 465.43 | [1-(2-chloro-3,5-diethoxy-benzyl)-piperidin-4-yl]-(2-chloro-6,7-dihydro-5H-cyclopentapyrimidin-4-yl)-amine | (2-chloro-6,7-dihydro-5H-cyclopentapyrimidin-4-yl)-piperidin-4-yl-amine dihydrochloride (intermediate C9) and 2-chloro-3,5-diethoxy-benzaldehyde (intermediate D9) | ISP [M + H]+ 465.2 |
| 177 | 538.21 | {2,4-dichloro-6-[1-(3,5-diisopropoxy-benzyl)-piperidin-4-ylamino]-pyrimidin-5-yl}-acetic acid ethyl ester | [2,4-dichloro-6-(piperidin-4-ylamino)-pyrimidin-5-yl]-acetic acid ethyl ester dihydrochloride (intermediate C10) and 3,5-diisopropoxy-benzaldehyde (intermediate D7) | ESI [M + H]+ 539.3 |
| 178 | 528.17 | {2,4-dichloro-6-[1-(3,5-diethoxy-4-fluoro-benzyl)-piperidin-4-ylamino]-pyrimidin-5-yl}-acetic acid ethyl ester | [2,4-dichloro-6-(piperidin-4-ylamino)-pyrimidin-5-yl]-acetic acid ethyl ester dihydrochloride (intermediate C10) and 3,5-diethoxy-4-fluoro-benzaldehyde (intermediate D20) | ESI [M + H]+ 529.3 |
| 179 | 544.14 | {2,4-dichloro-6-[1-(4-chloro-3,5-diethoxy-benzyl)-piperidin-4-ylamino]-pyrimidin-5-yl}-acetic acid ethyl ester | [2,4-dichloro-6-(piperidin-4-ylamino)-pyrimidin-5-yl]-acetic acid ethyl ester dihydrochloride (intermediate C10) and 4-chloro-3,5-diethoxy-benzaldehyde (intermediate D17) | ESI [M + H]+ 547.3 |
| 180 | 525.19 | {4-[1-(4-amino-3,5-diethoxy-benzyl)-piperidin-4-ylamino]-2,6-dichloro-pyrimidin-5-yl}-acetic acid ethyl ester | [2,4-dichloro-6-(piperidin-4-ylamino)-pyrimidin-5-yl]-acetic acid ethyl ester dihydrochloride (intermediate C10) and 4-amino-3,5-diethoxy-benzaldehyde (intermediate D23) | ESI [M − H]− 524.3 |
| 181 | 575.21 | {2,4-dichloro-6-[1-(3,5-diethoxy-4-pyrrol-1-yl-benzyl)-piperidin-4- | [2,4-dichloro-6-(piperidin-4-ylamino)-pyrimidin-5-yl]-acetic acid ethyl ester dihydrochloride | ESI [M + H]+ 576.3 |

TABLE 4-continued

| No | MW | Compound Name | Starting Materials | [M + H]+ or [M − H]− found |
|---|---|---|---|---|
| | | ylamino]-pyrimidin-5-yl}-acetic acid ethyl ester | (intermediate C10) and 3,5-diethoxy-4-pyrrol-1-yl-benzaldehyde (intermediate D19) | |
| 182 | 429.78 | [1-(3-ethoxy-4-methyl-benzyl)-piperidin-4-yl]-(2,5,6-trichloro-pyrimidin-4-yl)-amine | piperidin-4-yl-(2,5,6-trichloro-pyrimidin-4-yl)-amine dihydrochloride (intermediate C11) and 3-ethoxy-4-methyl-benzaldehyde (intermediate D10) | ISP [M + H]+ 429.2 |
| 183 | 450.20 | [1-(4-chloro-3-ethoxy-benzyl)-piperidin-4-yl]-(2,5,6-trichloro-pyrimidin-4-yl)-amine | piperidin-4-yl-(2,5,6-trichloro-pyrimidin-4-yl)-amine dihydrochloride (intermediate C11) and 4-chloro-3-ethoxy-benzaldehyde (intermediate D2) | ISP [M + H]+ 451.0 |
| 184 | 445.78 | [1-(3-ethoxy-4-methoxy-benzyl)-piperidin-4-yl]-(2,5,6-trichloro-pyrimidin-4-yl)-amine | piperidin-4-yl-(2,5,6-trichloro-pyrimidin-4-yl)-amine dihydrochloride (intermediate C11) and 3-ethoxy-4-methoxy-benzaldehyde (commercially available) | ISP [M + H]+ 447.1 |
| 185 | 463.77 | {1-[3-(2-fluoro-ethoxy)-4-methoxy-benzyl]-piperidin-4-yl}-(2,5,6-trichloro-pyrimidin-4-yl)-amine | piperidin-4-yl-(2,5,6-trichloro-pyrimidin-4-yl)-amine dihydrochloride (intermediate C11) and 3-(2-fluoro-ethoxy)-4-methoxy-benzaldehyde (intermediate D12) | ISP [M + H]+ 465.1 |
| 186 | 473.83 | [1-(3-isobutoxy-4-methoxy-benzyl)-piperidin-4-yl]-(2,5,6-trichloro-pyrimidin-4-yl)-amine | piperidin-4-yl-(2,5,6-trichloro-pyrimidin-4-yl)-amine dihydrochloride (intermediate C11) and 3-isobutoxy-4-methoxy-benzaldehyde (intermediate D15) | ISP [M + H]+ 473.1 |
| 187 | 487.86 | [1-(3,5-diisopropoxy-benzyl)-piperidin-4-yl]-(2,5,6-trichloro-pyrimidin-4-yl)-amine | piperidin-4-yl-(2,5,6-trichloro-pyrimidin-4-yl)-amine dihydrochloride (intermediate C11) and 3,5-diisopropoxy-benzaldehyde (intermediate D7) | ISP [M + H]+ 487.2 |
| 188 | 494.25 | [1-(4-chloro-3,5-diethoxy-benzyl)-piperidin-4-yl]-(2,5,6-trichloro-pyrimidin-4-yl)-amine | piperidin-4-yl-(2,5,6-trichloro-pyrimidin-4-yl)-amine dihydrochloride (intermediate C11) and 4-chloro-3,5-diethoxy-benzaldehyde (intermediate D17) | ISP [M + H]+ 495.2 |
| 189 | 524.88 | [1-(3,5-diethoxy-4-pyrrol-1-yl-benzyl)-piperidin-4-yl]-(2,5,6-trichloro-pyrimidin-4-yl)-amine | piperidin-4-yl-(2,5,6-trichloro-pyrimidin-4-yl)-amine dihydrochloride (intermediate C11) and 3,5-diethoxy-4-pyrrol-1-yl-benzaldehyde (intermediate D19) | ISP [M + H]+ 524.2 |
| 190 | 410.95 | (7-chloro-quinazolin-4-yl)-[1-(3-ethoxy-4-methyl-benzyl)-piperidin-4-yl]-amine | (7-chloro-quinazolin-4-yl)-piperidin-4-yl-amine dihydrochloride (intermediate C12) and 3-ethoxy-4-methyl-benzaldehyde (intermediate D10) | ESI [M + H]+ 410.7 |
| 191 | 414.91 | (7-chloro-quinazolin-4-yl)-[1-(3-ethoxy-4-fluoro-benzyl)-piperidin-4-yl]-amine | (7-chloro-quinazolin-4-yl)-piperidin-4-yl-amine dihydrochloride (intermediate C12) and 3-ethoxy-4-fluoro-benzaldehyde (intermediate D1) | ESI [M + H]+ 414.6 |
| 192 | 412.92 | 4-[4-(7-chloro-quinazolin-4-ylamino)-piperidin-1-ylmethyl]-2-ethoxy-phenol | (7-chloro-quinazolin-4-yl)-piperidin-4-yl-amine dihydrochloride (intermediate C12) and 3-ethoxy-4-hydroxy-benzaldehyde (commercially available) | ESI [M + H]+ 412.6 |
| 193 | 440.97 | (7-chloro-quinazolin-4-yl)-[1-(3,5-diethoxy-benzyl)-piperidin-4-yl]-amine | (7-chloro-quinazolin-4-yl)-piperidin-4-yl-amine dihydrochloride (intermediate C12) and 3,5-diethoxy-benzaldehyde (intermediate D5) | ESI [M + H]+ 440.7 |

TABLE 4-continued

| No | MW | Compound Name | Starting Materials | [M + H]+ or [M − H]− found |
|---|---|---|---|---|
| 194 | 469.03 | (7-chloro-quinazolin-4-yl)-[1-(3,5-diisopropoxy-benzyl)-piperidin-4-yl]-amine | (7-chloro-quinazolin-4-yl)-piperidin-4-yl-amine dihydrochloride (intermediate C12) and 3,5-diisopropoxy-benzaldehyde (intermediate D7) | ESI [M + H]+ 468.7 |
| 195 | 458.96 | (7-chloro-quinazolin-4-yl)-[1-(3,5-diethoxy-4-fluoro-benzyl)-piperidin-4-yl]-amine | (7-chloro-quinazolin-4-yl)-piperidin-4-yl-amine dihydrochloride (intermediate C12) and 3,5-diethoxy-4-fluoro-benzaldehyde (intermediate D20) | ESI [M + H]+ 458.7 |
| 196 | 475.42 | [1-(4-chloro-3,5-diethoxy-benzyl)-piperidin-4-yl]-(7-chloro-quinazolin-4-yl)-amine | (7-chloro-quinazolin-4-yl)-piperidin-4-yl-amine dihydrochloride (intermediate C12) and 4-chloro-3,5-diethoxy-benzaldehyde (intermediate D17) | ESI [M + H]+ 475.4 |
| 197 | 455.99 | [1-(4-amino-3,5-diethoxy-benzyl)-piperidin-4-yl]-(7-chloro-quinazolin-4-yl)-amine | (7-chloro-quinazolin-4-yl)-piperidin-4-yl-amine dihydrochloride (intermediate C12) and 4-amino-3,5-diethoxy-benzaldehyde (intermediate D23) | ESI [M − H]− 453.7 |
| 198 | 506.05 | (7-chloro-quinazolin-4-yl)-[1-(3,5-diethoxy-4-pyrrol-1-yl-benzyl)-piperidin-4-yl]-amine | (7-chloro-quinazolin-4-yl)-piperidin-4-yl-amine dihydrochloride (intermediate C12) and 3,5-diethoxy-4-pyrrol-1-yl-benzaldehyde (intermediate D19) | ESI [M − H]− 505.8 |
| 199 | 474.97 | (2-chloro-6,7-dimethoxy-quinazolin-4-yl)-[1-(3-ethoxy-4-fluoro-benzyl)-piperidin-4-yl]-amine | (2-chloro-6,7-dimethoxy-quinazolin-4-yl)-piperidin-4-yl-amine dihydrochloride (intermediate C13) and 3-ethoxy-4-fluoro-benzaldehyde (intermediate D1) | ISP [M + H]+ 475.1 |
| 200 | 491.42 | (2-chloro-6,7-dimethoxy-quinazolin-4-yl)-[1-(4-chloro-3-ethoxy-benzyl)-piperidin-4-yl]-amine | (2-chloro-6,7-dimethoxy-quinazolin-4-yl)-piperidin-4-yl-amine dihydrochloride (intermediate C13) and 4-chloro-3-ethoxy-benzaldehyde (intermediate D2) | ISP [M + H]+ 491.1 |
| 201 | 529.08 | (2-chloro-6,7-dimethoxy-quinazolin-4-yl)-[1-(3,5-diisopropoxy-benzyl)-piperidin-4-yl]-amine | (2-chloro-6,7-dimethoxy-quinazolin-4-yl)-piperidin-4-yl-amine dihydrochloride (intermediate C13) and 3,5-diisopropoxy-benzaldehyde (intermediate D7) | ISP [M + H]+ 529.2 |
| 202 | 519.02 | (2-chloro-6,7-dimethoxy-quinazolin-4-yl)-[1-(3,5-diethoxy-4-fluoro-benzyl)-piperidin-4-yl]-amine | (2-chloro-6,7-dimethoxy-quinazolin-4-yl)-piperidin-4-yl-amine dihydrochloride (intermediate C13) and 3,5-diethoxy-4-fluoro-benzaldehyde (intermediate D20) | ISP [M + H]+ 519.3 |
| 203 | 566.11 | (2-chloro-6,7-dimethoxy-quinazolin-4-yl)-[1-(3,5-diethoxy-4-pyrrol-1-yl-benzyl)-piperidin-4-yl]-amine | (2-chloro-6,7-dimethoxy-quinazolin-4-yl)-piperidin-4-yl-amine dihydrochloride (intermediate C13) and 3,5-diethoxy-4-pyrrol-1-yl-benzaldehyde (intermediate D19) | ISP [M + H]+ 566.3 |
| 204 | 366.47 | [1-(3-ethoxy-4-methyl-benzyl)-piperidin-4-yl]-(9H-purin-6-yl)-amine | piperidin-4-yl-(9H-purin-6-yl)-amine dihydrochloride (intermediate C14) and 3-ethoxy-4-methyl-benzaldehyde (intermediate D10) | ISP [M + H]+ 367.2 |
| 205 | 386.89 | [1-(4-chloro-3-ethoxy-benzyl)-piperidin-4-yl]-(9H-purin-6-yl)-amine | piperidin-4-yl-(9H-purin-6-yl)-amine dihydrochloride (intermediate C14) and 4-chloro-3-ethoxy-benzaldehyde (intermediate D2) | ISP [M + H]+ 387.2 |
| 206 | 368.44 | 2-ethoxy-4-[4-(9H-purin-6-ylamino)-piperidin-1-ylmethyl]-phenol | piperidin-4-yl-(9H-purin-6-yl)-amine dihydrochloride (intermediate C14) and 3-ethoxy-4-hydroxy-benzaldehyde (commercially available) | ISP [M + H]+ 369.3 |

TABLE 4-continued

| No | MW | Compound Name | Starting Materials | [M + H]⁺ or [M − H]⁻ found |
|---|---|---|---|---|
| 207 | 382.47 | [1-(3-ethoxy-4-methoxy-benzyl)-piperidin-4-yl]-(9H-purin-6-yl)-amine | piperidin-4-yl-(9H-purin-6-yl)-amine dihydrochloride (intermediate C14) and 3-ethoxy-4-methoxy-benzaldehyde (commercially available) | ISP [M + H]⁺ 383.2 |
| 208 | 410.52 | [1-(3-ethoxy-4-isopropoxy-benzyl)-piperidin-4-yl]-(9H-purin-6-yl)-amine | piperidin-4-yl-(9H-purin-6-yl)-amine dihydrochloride (intermediate C14) and 3-ethoxy-4-isopropoxy-benzaldehyde (commercially available) | ISP [M + H]⁺ 411.4 |
| 209 | 396.49 | [1-(4-methoxy-3-propoxy-benzyl)-piperidin-4-yl]-(9H-purin-6-yl)-amine | piperidin-4-yl-(9H-purin-6-yl)-amine dihydrochloride (intermediate C14) and 4-methoxy-3-propoxy-benzaldehyde (intermediate D11) | ISP [M + H]⁺ 397.3 |
| 210 | 400.46 | {1-[3-(2-fluoro-ethoxy)-4-methoxy-benzyl]-piperidin-4-yl}-(9H-purin-6-yl)-amine | piperidin-4-yl-(9H-purin-6-yl)-amine dihydrochloride (intermediate C14) and 3-(2-fluoro-ethoxy)-4-methoxy-benzaldehyde (intermediate D12) | ISP [M + H]⁺ 401.3 |
| 211 | 410.52 | [1-(3-butoxy-4-methoxy-benzyl)-piperidin-4-yl]-(9H-purin-6-yl)-amine | piperidin-4-yl-(9H-purin-6-yl)-amine dihydrochloride (intermediate C14) and 3-butoxy-4-methoxy-benzaldehyde (intermediate D4) | ISP [M + H]⁺ 411.4 |
| 212 | 410.52 | [1-(3-isobutoxy-4-methoxy-benzyl)-piperidin-4-yl]-(9H-purin-6-yl)-amine | piperidin-4-yl-(9H-purin-6-yl)-amine dihydrochloride (intermediate C14) and 3-isobutoxy-4-methoxy-benzaldehyde (intermediate D15) | ISP [M + H]⁺ 411.4 |
| 213 | 434.54 | [1-(8-ethoxy-2,2-dimethyl-2H-chromen-6-ylmethyl)-piperidin-4-yl]-(9H-purin-6-yl)-amine | piperidin-4-yl-(9H-purin-6-yl)-amine dihydrochloride (intermediate C14) and 8-ethoxy-2,2-dimethyl-2H-chromene-6-carbaldehyde (intermediate D16) | ISP [M + H]⁺ 435.4 |
| 214 | 424.55 | [1-(3,5-diisopropoxy-benzyl)-piperidin-4-yl]-(9H-purin-6-yl)-amine | piperidin-4-yl-(9H-purin-6-yl)-amine dihydrochloride (intermediate C14) and 3,5-diisopropoxy-benzaldehyde (intermediate D7) | ISP [M + H]⁺ 425.4 |
| 215 | 430.94 | [1-(4-chloro-3,5-diethoxy-benzyl)-piperidin-4-yl]-(9H-purin-6-yl)-amine | piperidin-4-yl-(9H-purin-6-yl)-amine dihydrochloride (intermediate C14) and 4-chloro-3,5-diethoxy-benzaldehyde (intermediate D17) | ISP [M + H]⁺ 431.3 |
| 216 | 461.57 | [1-(3,5-diethoxy-4-pyrrol-1-yl-benzyl)-piperidin-4-yl]-(9H-purin-6-yl)-amine | piperidin-4-yl-(9H-purin-6-yl)-amine dihydrochloride (intermediate C14) and 3,5-diethoxy-4-pyrrol-1-yl-benzaldehyde (intermediate D19) | ISP [M + H]⁺ 462.4 |

Example 217

6-[1-(4-Chloro-3-ethoxy-benzyl)-piperidin-4-ylamino]-pyrimidine-2,4-dicarboxylic acid To a solution of 2-chloro-6-(piperidin-4-ylamino)-pyrimidine-4-carboxylic acid methyl ester dihydrochloride (51.6 mg, 0.15 mmol, 1.0 equiv; intermediate C5) in ethanol (2 mL) was added 4-chloro-3-ethoxy-benzaldehyde (33.2 mg, 0.18 mmol, 1.2 equiv; intermediate D2), acetic acid (27.0 mg, 0.45 mmol, 3.0 equiv) and N-ethyl diisopropylamine (58.3 mg, 0.45 mmol, 3.0 equiv) and the reaction mixture stirred at 55° C. After 1 h, sodium cyanoborohydride (47.1 mg, 0.75 mmol, 5.0 equiv), dissolved in ethanol (0.5 mL), was added and the mixture stirred at 55° C. After 8 h, a 10 M NaOH solution (0.75 mL) was added and heating continued at 55° C. overnight. Removal of the solvent under reduced pressure and purification by preparative HPLC on reversed phase eluting with a gradient of acetonitrile/water provided 2.5 mg (4%) of the title compound. MS (ESI): 434.4 [M+H]⁺.

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula I | 3.0 mg |
| Gelatine | 150.0 mg |
| Phenol | 4.7 mg |
| Sodium carbonate | to obtain a final pH of 7 |
| Water for injection solutions | ad 1.0 mL |

Example D

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula I | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:
1. A compound of formula I:

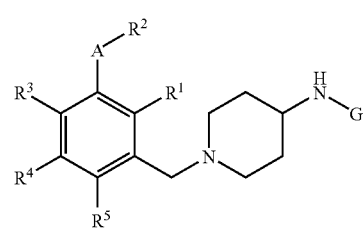

wherein

A is —O— or —NH—;

$R^1$ is selected from the group consisting of hydrogen, $C_{1-7}$-alkoxy and halogen;

$R^2$ is selected from the group consisting of $C_{2-7}$-alkyl, $C_{2-7}$-alkenyl, halogen-$C_{1-7}$-alkyl, $C_{1-7}$-alkoxy-$C_{1-7}$-alkyl, and benzyl;

$R^3$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O—$C_{3-7}$-cycloalkyl, halogen, halogen-$C_{1-7}$-alkyl, —$NR^6R^7$, wherein $R^6$ and $R^7$ independently from each other are hydrogen or $C_{1-7}$-alkyl, —O—$SO_2$—$R^8$, wherein $R^8$ is $C_{1-7}$-alkyl, and pyrrolyl;

$R^4$ is selected from the group consisting of hydrogen, hydroxy, $C_{1-7}$-alkoxy, amino, nitro, hydroxy-$C_{1-7}$-alkoxy, $C_{1-7}$-alkoxy-$C_{1-7}$-alkoxy, and —O-benzyl;

or $R^3$ and $R^4$ are bonded to each other to form a ring together with the carbon atoms they are attached to and $R^3$ and $R^4$ together are —O—$C(CH_3)_2$—CH=CH—;

$R^5$ is selected from the group consisting of hydrogen, halogen and $C_{1-7}$-alkoxy;

G is selected from the groups

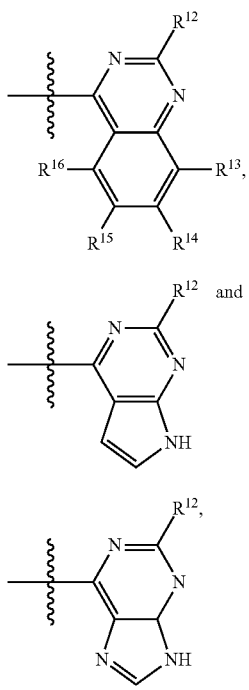

wherein $R^{12}$ is selected from the group consisting of hydrogen, $C_{1-7}$-alkyl, halogen, halogen-$C_{1-7}$-alkyl, amino, phenyl, —$OR^{23}$, wherein $R^{23}$ is hydrogen or $C_{1-7}$-alkyl, and —C(O)—$OR^{24}$, wherein $R^{24}$ is hydrogen or $C_{1-7}$-alkyl;

$R^{13}$, $R^{14}$, $R^{15}$ and $R^{16}$ independently from each other are selected from the group consisting of hydrogen, $C_{1-7}$-alkyl, halogen, hydroxy, and $C_{1-7}$-alkoxy;

and pharmaceutically acceptable salts thereof.

2. The compound according to claim 1, wherein A is O.

3. The compound according to claim 1, wherein $R^1$ is hydrogen or halogen.

4. The compound according to claim 1, wherein $R^2$ is selected from the group consisting of $C_{2-7}$-alkyl, $C_{2-7}$-alkenyl, halogen-$C_{1-7}$-alkyl and $C_{1-7}$-alkoxy-$C_{1-7}$-alkyl.

5. The compound according to claim 1, wherein $R^2$ is selected from the group consisting of ethyl, propyl, isopropyl, allyl, 2-fluoroethyl, 2,2,2-trifluoroethyl, butyl and isobutyl.

6. The compound according to claim 1, wherein $R^3$ is selected from the group consisting of hydrogen, $C_{1-7}$-alkyl, hydroxy, $C_{1-7}$-alkoxy, halogen, —$NR^6R^7$, wherein $R^6$ and $R^7$ independently from each other are hydrogen or $C_{1-7}$-alkyl, —O—$SO_2$—$R^8$, wherein $R^8$ is $C_{1-7}$-alkyl, and pyrrolyl.

7. The compound according to claim 1, wherein $R^3$ is hydrogen or halogen.

8. The compound according to claim 1, wherein $R^3$ is halogen.

9. The compound according to claim 1, wherein $R^4$ is selected from the group consisting of hydrogen, hydroxy, $C_{1-7}$-alkoxy, nitro, $C_{1-7}$-alkoxy-$C_{1-7}$-alkoxy, and —O-benzyl.

10. The compound according to claim 1, wherein $R^3$ and $R^4$ are bonded to each other to form a ring together with the carbon atoms they are attached to and $R^3$ and $R^4$ together are —O—$C(CH_3)_2$—CH=CH—.

11. The compound according to claim 1, wherein $R^5$ is hydrogen or halogen.

12. The compound according to claim 1, wherein G is

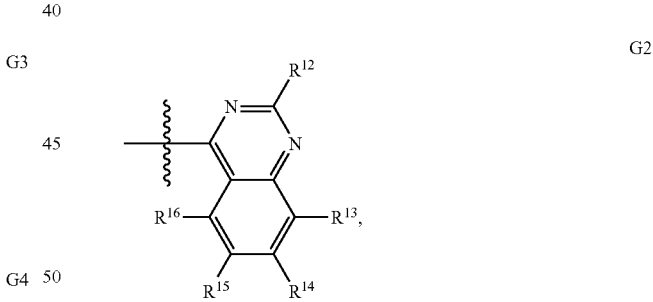

and wherein $R^{12}$ is selected from the group consisting of hydrogen, $C_{1-7}$-alkyl, halogen, halogen-$C_{1-7}$-alkyl, amino, phenyl, —$OR^{23}$, wherein $R^{23}$ is hydrogen or $C_{1-7}$-alkyl, and —C(O)—$OR^{24}$, wherein $R^{24}$ is hydrogen or $C_{1-7}$-alkyl;

$R^{13}$, $R^{14}$, $R^{15}$ and $R^{16}$ independently from each other are selected from the group consisting of hydrogen, $C_{1-7}$-alkyl, halogen, hydroxy, and $C_{1-7}$-alkoxy.

13. The compound according to claim 1, wherein $R^{12}$ is halogen.

14. The compound according to claim 1, wherein G is selected from the group consisting of

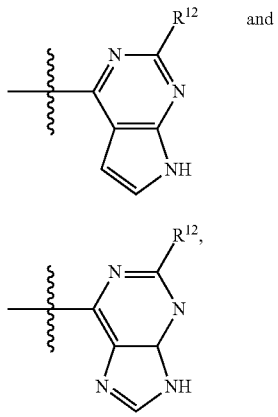

and wherein
$R^{12}$ is selected from the group consisting of hydrogen, $C_{1-7}$-alkyl,
halogen, halogen-$C_{1-7}$-alkyl,
amino, phenyl,
—$OR^{23}$, wherein $R^{23}$ is hydrogen or $C_{1-7}$-alkyl, and
—C(O)—$OR^{24}$, wherein $R^{24}$ is hydrogen or $C_{1-7}$-alkyl.

15. The compound according to claim 14, wherein $R^{12}$ is halogen.

16. The compound according to claim 1, selected from the group consisting of
[1-(4-chloro-3-ethoxy-benzyl)-piperidin-4-yl]-(7-chloro-quinazolin-4-yl)-amine,
and
(7-chloro-quinazolin-4-yl)-[1-(3,5-diisopropoxy-benzyl)-piperidin-4-yl]-amine,
and pharmaceutically acceptable salts thereof.

17. A pharmaceutical composition, comprising a therapeutically effective amount of a compound according to claim 1 as well as a pharmaceutically acceptable carrier and/or adjuvant.

18. A process for the manufacture of a compound according to claim 1, comprising the steps of:
a) reacting a compound of the general formula

G-X     II wherein G is as defined in claim 1 and X is halogen, with a compound of the formula

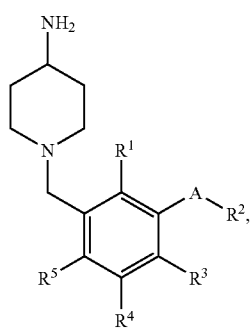

wherein A and $R^1$, $R^2$, $R^3$, $R^4$ and $R^5$ are as defined in claim 1, to obtain a compound of the formula

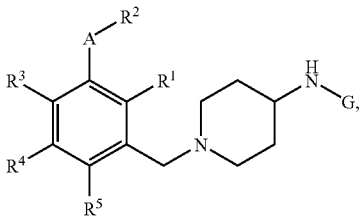

and, if desired, converting the compound of formula I into a pharmaceutically acceptable salt; or, alternatively,
b) reacting a compound of the formula

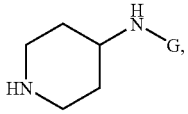

wherein G is as defined in claim 1,
with an aldehyde of the formula

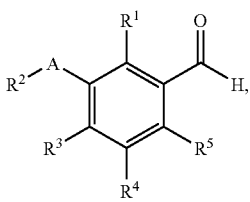

wherein A and $R^1$, $R^2$, $R^3$, $R^4$ and $R^5$ are as defined in claim 1,
by employing a reducing agent to obtain a compound of the formula

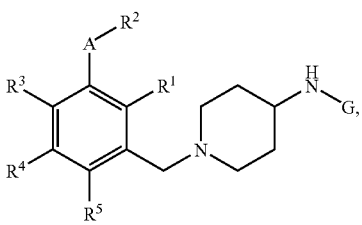

and, if desired, converting the compound of formula I into a pharmaceutically acceptable salt.

* * * * *